US012680100B2

(12) United States Patent
Khurana

(10) Patent No.: US 12,680,100 B2
(45) Date of Patent: Jul. 14, 2026

(54) TROPHIN GENOME EDITING FOR TREATING DUCHENNE MUSCULAR DYSTROPHY (DMD)

(71) Applicant: THE TRUSTEES OF THE UNIVERSITY OF PENNSYLVANIA, Philadelphia, PA (US)

(72) Inventor: Tejvir S. Khurana, Narberth, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 678 days.

(21) Appl. No.: 18/005,612

(22) PCT Filed: Jul. 26, 2021

(86) PCT No.: PCT/US2021/043185

§ 371 (c)(1), (2) Date: Jan. 16, 2023

(87) PCT Pub. No.: WO2022/020806

PCT Pub. Date: Jan. 27, 2022

(65) Prior Publication Data

US 2023/0313186 A1 Oct. 5, 2023

Related U.S. Application Data

(60) Provisional application No. 63/056,397, filed on Jul. 24, 2020.

(51) Int. Cl.

| | |
|---|---|
| ***C12N 15/113*** | (2010.01) |
| ***A61P 21/00*** | (2006.01) |
| ***C07K 14/47*** | (2006.01) |
| ***C12N 5/074*** | (2010.01) |
| ***C12N 15/86*** | (2006.01) |

(52) U.S. Cl.

CPC ............ *C12N 15/113* (2013.01); *A61P 21/00* (2018.01); *C07K 14/4708* (2013.01); *C12N 5/0696* (2013.01); *C12N 15/86* (2013.01); *C12N 2310/20* (2017.05); *C12N 2710/10041* (2013.01)

(58) Field of Classification Search

None

See application file for complete search history.

(56) References Cited

U.S. PATENT DOCUMENTS

| | | | | |
|---|---|---|---|---|
| 2009/0105467 | A1 | 4/2009 | Damba et al. | |
| 2011/0065653 | A1 | 3/2011 | Ervasti et al. | |
| 2012/0122953 | A1* | 5/2012 | Moorwood .......... | C12N 15/113 435/375 |
| 2015/0099790 | A1 | 4/2015 | Rutter et al. | |

FOREIGN PATENT DOCUMENTS

| | | | | |
|---|---|---|---|---|
| WO | WO-2014197748 A2 * | 12/2014 | .............. | C12N 9/22 |
| WO | WO 2019/060454 A2 | 3/2019 | | |

OTHER PUBLICATIONS

Sengupta, et al. (Utrophin Genome Editing for Duchene Muscular Dystophy (DMD). The Sixteenth Annual Biomedical Postdoctoral Research Symposium (online). University of Pennsylvania. 2017 (retrieved on Dec. 26, 2021) Retrieved from the Internet (URL: https:/Awww.med.upenn.edu/bprs/abstracts.html]).*

Chen et al. (Global microRNA depletion suppresses tumor angiogenesis. Genes Dev. May 15, 2014;28(10):1054-67).*

Denisov et al., "Solution structure of an arabinonucleic acid (ANA)/RNA duplex in a chimeric hairpin: comparison with 2'-fluoro-ANA/RNA and DNA/RNA hybrids." Nucleic Acids Research 29.21 (2001): 4284-4293.

International Preliminary Report on Patentability from PCT/US2021/043185 dated Feb. 2, 2023.

International Search Report from PCT/US2021/043185 dated Feb. 3, 2023.

Summerton et al., Morpholino Antisense Oligomers: Design Preparation and Properties. Antisense & Nucleic Acid Drug Development 7.3, 1997, 187-195.

Trempe et al., "NMR solution structure of an oligonucleotide hairpin with a 2 'F-ANA/RNA stem: implications for RNase H specificity toward DNA/RNA hybrid duplexes." Journal of the American Chemical Society 123.21 (2001): 4896-4903.

Vu et al., "Internucleotide phosphite sulfurization with tetraethylthiuram disulfide. Phosphorothioate oligonucleotide synthesis via phosphoramidite chemistry." Tetrahedron Letters 32.26 (1991): 3005-3008.(Abstract).

Wang et al., "Cyclohexene nucleic acids (CeNA): serum stable oligonucleotides that activate RNase H and increase duplex stability with complementary RNA." Journal of the American Chemical Society 122.36 (2000): 8595-8602. (Abstract).

Sengupta, K et al. Utrophin Genome Editing for Duchene Muscular Dystophy (DMD). The Sixteenth Annual Biomedical Postdoctoral Research Symposium (online). University of Pennsylvania. 2017 (retrieved on Dec. 26, 2021) Retrieved from the Internet (URL: https://www.med.upenn.edu/bprs/abstracts.html] pp. 1-4; p. 3, 1st, 2nd, 3rd and 4th paragraphs.

Koppanat, BM et al. Improvement of the mdx mouse dystophic phenotype by systemic in utero AAV8 delivery of a minidystrophin gene. Gene Therapy. Nov. 2010. Epub Jun. 10, 2010, vol. 17, No. 11; pp. 1355-1362; abstract; p. 1358, 2nd column, 2nd paragraph.

(Continued)

*Primary Examiner* — Christopher M Babic

(74) *Attorney, Agent, or Firm* — Mark S. Cohen; PEARL COHEN ZEDEK LATZER BARATZ LLP

(57) ABSTRACT

The invention relates to compositions and methods for improving a dystrophic phenotype in a human subject having myopathies, such as Duchenne Muscular Dystrophy (DMD). In one embodiment, the invention relates to compositions comprising an adenoviral vector targeting the let-7c miRNA binding sequence in 3'-UTR genome editing of the utrophin gene and methods of treatment comprising administration thereof.

28 Claims, 21 Drawing Sheets

Specification includes a Sequence Listing.

(56) References Cited

OTHER PUBLICATIONS

Hinton, VJ et al. Selective deficits in verbal working memory associated with a known genetic etiology: The neuropsychological profile of Duchenne muscular dystrophy. Journal of the International Neuropsychological Society. Jan. 2001, vol. 7, No. 1; pp. 1-2; abstract; p. 2, 5th paragraph.

Sato, T et al. Lin28a/let-7 pathway modulates the Hox code via Polycomb regulation during axial patteming in verterbrates. Elife. May 29, 2020, vol. 9, No. e53608; pp. 1-2; p. 2, 2nd paragraph.

Nance, ME et al. AAV9 Edits Muscle Stem Cells in Nomrla and Dystrophic Adult Mice. Molecular Therapy. Sep. 4, 2019, Epub Jul. 3, 2019, vol. 27, No. 9; pp. 1568-1585; entire document.

* cited by examiner

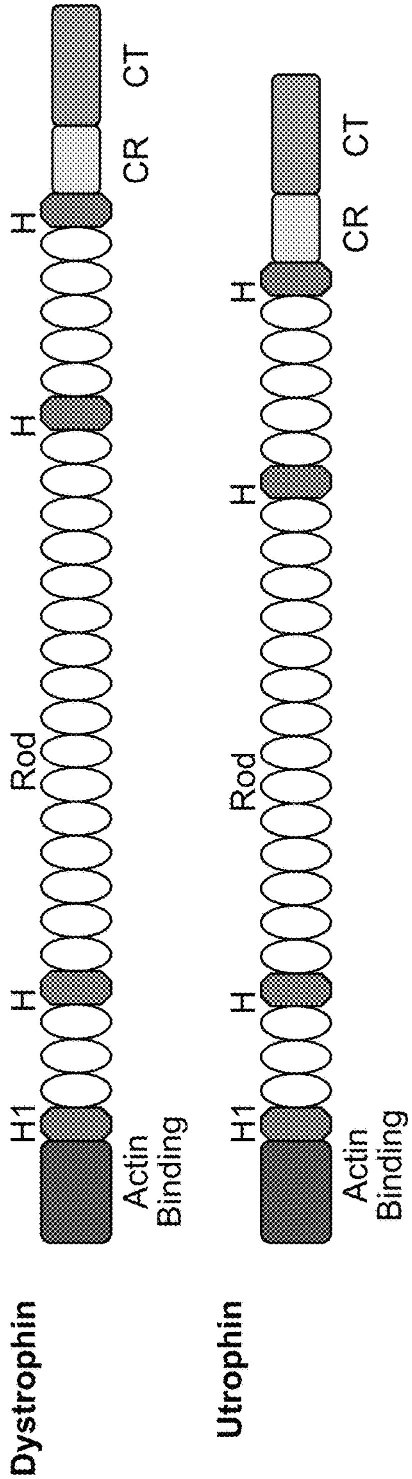
FIGURE 1
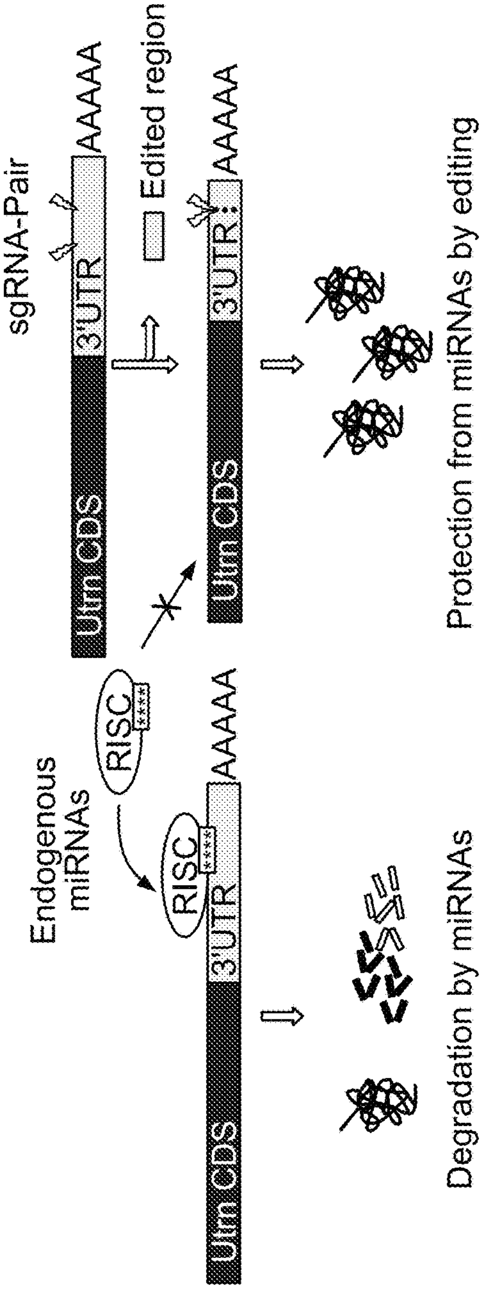
FIGURE 2A
FIGURE 2B

| Human PCR | | |
|---|---|---|
| ***Constructs*** | ***PCR Product size (bp)*** | ***Deletion (bp)*** |
| SaCas9 control | 811 | - |
| sgRNA 1 & sgRNA 4 | 398 | 413 |
| sgRNA 1 & sgRNA 5 | 278 | 533 |
| sgRNA 2 & sgRNA 4 | 445 | 366 |
| sgRNA 2 & sgRNA 5 | 325 | 486 |

Genome editing of Utrn 3'UTR Using pX601+sgRNA7 and pX601+sgRNA13 constructs

Line Intensity plot of α-sarcoglycan within individual myotubes

α-Sarcoglycan intensity normalized with DAPI

Percentage normalized α-sarcoglycan intensity of individual group

Statistical analysis by Kruskal-Wallis multiple comparison test

SEQUENCE LISTING

```
<160> NUMBER OF SEQ ID NOS: 108

<210> SEQ ID NO 1
<211> LENGTH: 22
<212> TYPE: RNA
<213> ORGANISM: Unknown
<220> FEATURE:
<223> OTHER INFORMATION: Description of Unknown:
      microRNA sequence

<400> SEQUENCE: 1

ugagguagua gguuguaugg uu                                              22


<210> SEQ ID NO 2
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2

aaccauacaa ccuacuaccu ca                                              22


<210> SEQ ID NO 3
<211> LENGTH: 22
<212> TYPE: RNA
<213> ORGANISM: Unknown
<220> FEATURE:
<223> OTHER INFORMATION: Description of Unknown:
      microRNA sequence
```

<400> SEQUENCE: 3
uuuggucccc uucaaccagc ua 22

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 4
uagcugguug aaggggacca a 21

<210> SEQ ID NO 5
<211> LENGTH: 22
<212> TYPE: RNA
<213> ORGANISM: Unknown
<220> FEATURE:
<223> OTHER INFORMATION: Description of Unknown:
microRNA sequence

<400> SEQUENCE: 5
ucucccaacc cuuguaccag ug 22

<210> SEQ ID NO 6
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 6
cacugguaca aggguuggga ga 22

<210> SEQ ID NO 7
<211> LENGTH: 22
<212> TYPE: RNA
<213> ORGANISM: Unknown
<220> FEATURE:
<223> OTHER INFORMATION: Description of Unknown:
microRNA sequence

<400> SEQUENCE: 7
uagguaguuu ccuguuguug gg 22

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 8
ccaacaacag gaaacuaccu a 21

<210> SEQ ID NO 9
<211> LENGTH: 22
<212> TYPE: RNA
<213> ORGANISM: Unknown
<220> FEATURE:
<223> OTHER INFORMATION: Description of Unknown:
microRNA sequence

<400> SEQUENCE: 9

-continued

```
uggaauguaa ggaagugugu gg                                              22


<210> SEQ ID NO 10
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10

ccacacacuu ccuuacauuc ca                                              22


<210> SEQ ID NO 11
<211> LENGTH: 21
<212> TYPE: RNA
<213> ORGANISM: Unknown
<220> FEATURE:
<223> OTHER INFORMATION: Description of Unknown:
      microRNA sequence

<400> SEQUENCE: 11

agggcccccc cucaauccug u                                               21


<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12

acaggauuga gggggggccc u                                               21


<210> SEQ ID NO 13
<211> LENGTH: 2391
<212> TYPE: DNA
<213> ORGANISM: Mus musculus

<400> SEQUENCE: 13

tgagcatcta tccagccagc caacatttcc cgaccttcag tattgccctc ttctgcaaat      60

gccaatccca agacccattc aaccccaaag ctccgtggct ccacgacaca agctgttgag     120

tgcttactgg gtgttctact gagggaacca aacactgact atccaaagag aaaaggatat     180

tttggttttc taataacgta tattattgtt ttcttctccc ctttctatgc aactgtaaat     240

taatgaacag agaagtattt ggaggtggta aagcatttgt cactgatttg tataatatat     300

acagccatgg gaaagtgggt gggggctttc taatatgaaa ctgtcttttt aataaccaag     360

agaaaaaatt gcataagaat tagaccactt tacattatta cattccttct gctgttcaca     420

ttaaccttgt acaataactt cacttattat ttgactgttt taccattatg ttttggttat     480

ttataaattt atcagccata caaacaaata gattctatgt atttgtttct ataatctggc     540

caaattccta agttcatata tttgaatcaa atattttaca tatgtggagt aggcaggcat     600

tctgaagata ctatttaact ttagttgacg tcacacacac catcctttag taaccactgg     660

atgactacac taaaaatcct gtggacttta acggcaagct gctggggtat ttttcctcct     720

gtttttattc cttttttgta agtagatctt gacgtcttta tttatttcat cttgcaatct     780

ctataataaa gaagactgta ttgtaatagt ctcaaaaaat tattttacca agggttacca     840

tttaagcata ttttcatttt gattcagaaa ccaaagttgg tacaacctct cctagtacat     900
```

-continued gcaaccttgg ttttcatgag aaaacacacg gcaggccttt gcccattgtg aggagagcac 960
acatcatgct cttcagtttc ctttgaatag acttttattg ttgtttttgt atttttcgag 1020
tcctgtgtaa gttttgaaag ctctggttgt ttcctttgtg aaagcaggca gatacttagt 1080
tggctgtctc atttgaagct ttggagcaga tagtcagatg tctcatgacc cctcacttgg 1140
ccagcagcac atccgagaag gatgtcactc acaagcctac accacggctt ctctagaatg 1200
aaatcagtgc tcggatgatt gtatccctgc ctctacttct gagtgtgttc aactaggtat 1260
tggcttcttt ttctttttct tttctttttt ttttaattta acacttaatt gccgatttta 1320
gagaaaccaa aaataaaggt gaaggtaata tgttttgatt caaacatata tgcttttaaa 1380
catcagacat gctaactttg gttctcttta ctggaatctg gcccagagga ggtgaaattt 1440
agaaatgtta ttctttagat gggtgggtgg gttgggggc caagggtgtc tattttccag 1500
cattagatat ttttgagacg aagaaaattg ttttatataa ggggagagcc atgatcacct 1560
ttctacctca gaaccacctt cctccattgt gttggacata gctttatatg ccgcagtgtg 1620
caaaacctag ggctgtagtc aggcctttcc atacccagga agcacctgtg taaagaagat 1680
caacagaaac tcccggaact cagaacccca agttgtagat ttggtgtcgt ccttgttctt 1740
gctttgagga gtcatgtatt cttttatttc ctgcctgtat ttgtatgcaa aatgatctct 1800
atctgctatt acagaaaaag ctacacaaaa cactacattg taaccttctg agtaataaat 1860
aagaggaaat atattacagt aaccatgatg agaaataagt gtattgttct tttgaaatat 1920
gtggttaatc gcagactgtc atctaatctg ttacataccg tatttttcat cctgaataaa 1980
agtaatttta acacaaaatg actttgatgt ttggctgtgt tcagctgatg aaatcagatc 2040
tctgaatgta tgtgatgaaa gctaactata agatgatcta tattctgata aatctaaata 2100
ttttctgaaa ctctctctta tacattaatc tagtctccat tcactcatta tctctctctc 2160
ctttcttgca tataaatatg attatatatt tttcaatttc ctgtacaaat cagagtctta 2220
ttactaggga aaatggatgt tataagtaca ttcctaaagc ccattgggcc ttcattttta 2280
taacttggag ctactgagat ttatcaggtt actctctcaa atccactttc atcactagac 2340
tcatagtttt ctatgtatct atattattat aactaaataa aaatatacat g 2391

<210> SEQ ID NO 14
<211> LENGTH: 23
<212> TYPE: DNA
<213> ORGANISM: Mus musculus

<400> SEQUENCE: 14
atgggaaagt gggtgggggc ttt 23

<210> SEQ ID NO 15
<211> LENGTH: 22
<212> TYPE: DNA
<213> ORGANISM: Mus musculus

<400> SEQUENCE: 15
ccactttaca ttattacatt cc 22

<210> SEQ ID NO 16
<211> LENGTH: 20
<212> TYPE: DNA
<213> ORGANISM: Mus musculus

<400> SEQUENCE: 16

-continued atgggtgggt gggttggggg 20

<210> SEQ ID NO 17
<211> LENGTH: 17
<212> TYPE: DNA
<213> ORGANISM: Mus musculus

<400> SEQUENCE: 17
gtgggttggg gggccaa 17

<210> SEQ ID NO 18
<211> LENGTH: 24
<212> TYPE: DNA
<213> ORGANISM: Mus musculus

<400> SEQUENCE: 18
agccatgatc acctttctac ctca 24

<210> SEQ ID NO 19
<211> LENGTH: 19
<212> TYPE: DNA
<213> ORGANISM: Mus musculus

<400> SEQUENCE: 19
ccatacccag gaagcacct 19

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23
<211> LENGTH: 21
<212> TYPE: DNA
<213> ORGANISM: Mus musculus

<400> SEQUENCE: 23
gggtgggtgg gttgggggc c 21

<210> SEQ ID NO 24
<211> LENGTH: 26
<212> TYPE: RNA
<213> ORGANISM: Mus musculus

<400> SEQUENCE: 24
cugagguaga aaggugauca uggcuc 26

<210> SEQ ID NO 25
<211> LENGTH: 26
<212> TYPE: RNA
<213> ORGANISM: Homo sapiens

<400> SEQUENCE: 25
cugagguaga aaggugguca uggcuu 26

<210> SEQ ID NO 26
<211> LENGTH: 27
<212> TYPE: RNA
<213> ORGANISM: Mus musculus

<400> SEQUENCE: 26
cugagguaga aaggugauca uggcucu 27

<210> SEQ ID NO 27
<211> LENGTH: 28
<212> TYPE: RNA
<213> ORGANISM: Mus musculus

<400> SEQUENCE: 27
cugagguaga aaggugauca uggcucuc 28

<210> SEQ ID NO 28
<211> LENGTH: 29
<212> TYPE: RNA
<213> ORGANISM: Mus musculus

<400> SEQUENCE: 28
cugagguaga aaggugauca uggcucucc 29

<210> SEQ ID NO 29
<211> LENGTH: 27
<212> TYPE: RNA
<213> ORGANISM: Mus musculus

<400> SEQUENCE: 29
ucugagguag aaaggugauc auggcuc 27

<210> SEQ ID NO 30
<211> LENGTH: 28
<212> TYPE: RNA
<213> ORGANISM: Mus musculus

<400> SEQUENCE: 30
uucugaggua gaaaggugau cauggcuc 28

<210> SEQ ID NO 31
<211> LENGTH: 29
<212> TYPE: RNA
<213> ORGANISM: Mus musculus

<400> SEQUENCE: 31
guucugaggu agaaagguga ucauggcuc 29

<210> SEQ ID NO 32
<211> LENGTH: 28
<212> TYPE: RNA
<213> ORGANISM: Mus musculus

<400> SEQUENCE: 32
ucugagguag aaaggugauc auggcucu 28

<210> SEQ ID NO 33
<211> LENGTH: 29
<212> TYPE: RNA
<213> ORGANISM: Mus musculus

<400> SEQUENCE: 33
uucugaggua gaaaggugau cauggcucu 29

<210> SEQ ID NO 34
<211> LENGTH: 30
<212> TYPE: RNA
<213> ORGANISM: Mus musculus

<400> SEQUENCE: 34
guucugaggu agaaagguga ucauggcucu 30

<210> SEQ ID NO 35
<211> LENGTH: 29
<212> TYPE: RNA
<213> ORGANISM: Mus musculus

<400> SEQUENCE: 35
ucugagguag aaaggugauc auggcucuc 29

<210> SEQ ID NO 36
<211> LENGTH: 30
<212> TYPE: RNA
<213> ORGANISM: Mus musculus

<400> SEQUENCE: 36
uucugaggua gaaaggugau cauggcucuc 30

<210> SEQ ID NO 37
<211> LENGTH: 31
<212> TYPE: RNA
<213> ORGANISM: Mus musculus

<400> SEQUENCE: 37
guucugaggu agaaagguga ucauggcucu c 31

<210> SEQ ID NO 38
<211> LENGTH: 30
<212> TYPE: RNA
<213> ORGANISM: Mus musculus

<400> SEQUENCE: 38
ucugagguag aaaggugauc auggcucucc 30

<210> SEQ ID NO 39
<211> LENGTH: 31
<212> TYPE: RNA
<213> ORGANISM: Mus musculus

<400> SEQUENCE: 39
uucugaggua gaaaggugau cauggcucuc c 31

<210> SEQ ID NO 40
<211> LENGTH: 32
<212> TYPE: RNA
<213> ORGANISM: Mus musculus

<400> SEQUENCE: 40
guucugaggu agaaagguga ucauggcucu cc 32

<210> SEQ ID NO 41
<211> LENGTH: 27
<212> TYPE: RNA

-continued

<213> ORGANISM: Homo sapiens

<400> SEQUENCE: 41
cugagguaga aaggugguca uggcuuu 27

<210> SEQ ID NO 42
<211> LENGTH: 28
<212> TYPE: RNA
<213> ORGANISM: Homo sapiens

<400> SEQUENCE: 42
cugagguaga aaggugguca uggcuuuc 28

<210> SEQ ID NO 43
<211> LENGTH: 29
<212> TYPE: RNA
<213> ORGANISM: Homo sapiens

<400> SEQUENCE: 43
cugagguaga aaggugguca uggcuuucc 29

<210> SEQ ID NO 44
<211> LENGTH: 27
<212> TYPE: RNA
<213> ORGANISM: Homo sapiens

<400> SEQUENCE: 44
ucugagguag aaaggugguc auggcuu 27

<210> SEQ ID NO 45
<211> LENGTH: 28
<212> TYPE: RNA
<213> ORGANISM: Homo sapiens

<400> SEQUENCE: 45
aucugaggua gaaagguggu cauggcuu 28

<210> SEQ ID NO 46
<211> LENGTH: 29
<212> TYPE: RNA
<213> ORGANISM: Homo sapiens

<400> SEQUENCE: 46
gaucugaggu agaaaggugg ucauggcuu 29

<210> SEQ ID NO 47
<211> LENGTH: 28
<212> TYPE: RNA
<213> ORGANISM: Homo sapiens

<400> SEQUENCE: 47
ucugagguag aaaggugguc auggcuuu 28

<210> SEQ ID NO 48
<211> LENGTH: 29
<212> TYPE: RNA
<213> ORGANISM: Homo sapiens

<400> SEQUENCE: 48
aucugaggua gaaagguggu cauggcuuu 29

<210> SEQ ID NO 49
<211> LENGTH: 30

```
<212> TYPE: RNA
<213> ORGANISM: Homo sapiens

<400> SEQUENCE: 49

gaucugaggu agaaaggugg ucauggcuuu                                        30


<210> SEQ ID NO 50
<211> LENGTH: 29
<212> TYPE: RNA
<213> ORGANISM: Homo sapiens

<400> SEQUENCE: 50

ucugagguag aaaggugguc auggcuuuc                                         29


<210> SEQ ID NO 51
<211> LENGTH: 30
<212> TYPE: RNA
<213> ORGANISM: Homo sapiens

<400> SEQUENCE: 51

aucugaggua gaaagguggu cauggcuuuc                                        30


<210> SEQ ID NO 52
<211> LENGTH: 31
<212> TYPE: RNA
<213> ORGANISM: Homo sapiens

<400> SEQUENCE: 52

gaucugaggu agaaaggugg ucauggcuuu c                                      31


<210> SEQ ID NO 53
<211> LENGTH: 30
<212> TYPE: RNA
<213> ORGANISM: Homo sapiens

<400> SEQUENCE: 53

ucugagguag aaaggugguc auggcuuucc                                        30


<210> SEQ ID NO 54
<211> LENGTH: 31
<212> TYPE: RNA
<213> ORGANISM: Homo sapiens

<400> SEQUENCE: 54

aucugaggua gaaagguggu cauggcuuuc c                                      31


<210> SEQ ID NO 55
<211> LENGTH: 32
<212> TYPE: RNA
<213> ORGANISM: Homo sapiens

<400> SEQUENCE: 55

gaucugaggu agaaaggugg ucauggcuuu cc                                     32


<210> SEQ ID NO 56
<211> LENGTH: 2045
<212> TYPE: DNA
<213> ORGANISM: Homo sapiens

<400> SEQUENCE: 56

tgaagtattc atccggccaa ccaatgtttc ctgacgtaca gtgttgccct tttcagcaaa      60

tgccaattcc aagttccatt aaatcagaag ctccatggct ccttggccca cgatgttgag     120
```

-continued

```
tgctgactgt gtgttctact gaaagagtaa aacactgact atccaaagag aaatggatat    180

tttgttttta taataaccat atattattgt tttcttcttc cctttctatg caagtgtaaa    240

ttaatgaaca gagaggtatt tggaaatggt aatacatttg tcacggattt gtataatgta    300

tacagcattg ggaaagtggg tgggggcttt ctaatatgat accgtctttt taataactat    360

gacaaagctt acataagaat tagaagacca ctttacattt ttacattcct tctgctgttc    420

atattaacct tgcacaatta cttcattttt tctttgactc ttttaccaca atgttttggt    480

tatttataat ttatcagcca tatgtttatc agccatataa ccaactagat cccaaataga    540

tccatgtatt tgtttccgtg atttggccac attaataaat tcataaattt caatcaaata    600

tcttatatat acacacatat ggtttaagct acagccctgt gtatgccgtt taactttatt    660

tgacgttgcc cacttacttc tttgctgacc acttggataa ccgtaataaa aatcctataa    720

gcctaaatgg catttctttt gggatatttt tcctgcattt tattcccttt ttatataagt    780

aggaattaat tatttatttt atgtcttaat ctatttgata aagaagacta cattataata    840

atctcaaaga tcatattacc aaaggttgcc cacttgagca tattttcatt ttgacacaga    900

aacaaaattt agtacaacct ttcctagttc ccatgtcttg attttcatca ttacatgcac    960

agcagacctt tacctattgt gataccagaa cacatcattg tctttggttc ccttcaaaga   1020

gaattttatt gttgttttgt attttcaagt ccttaatagt tcttgaaact cctagttgtt   1080

ttcttgttga aagcagacac acatttagtg cacggcttat tttacctttc gggtgaaaga   1140

tcagatgttt ttataccctt cacttgatca atatatttgg aaagaatgtt tatcaaaagt   1200

ctatgtcact gcttctacag aagaatgaaa ttaatgctta ggtgatggta cctccaccta   1260

catctttttg agtgcattca attatgtatt ttggtttagc ttctgattta acatttaatt   1320

gattcagttt aaacatgtta cttaattagc aaatgtagag gaaccaaaaa aaggtgaaaa   1380

taatatgttt tgattcaaac ctaaagacat aaaaacataa agacatttta actttgggtt   1440

ctctttagct gggatctggc cagaaggagg cttaaagtta gaaattgcta ttattttaga   1500

ataggttggg tgggttgggg ggcaagggtg tctatttgca gcagagatat tttgaaaaga   1560

agaaaattgt tttatataaa aaggaaagcc atgaccacct ttctacctca gatccatctt   1620

catccattgc attggaaact gctttatgct gctgcagtct gcaaagtcta gagcttttat   1680

caggccatgt catacccaag aaagcaccta tttaaagaaa aaacaattcc ctgagctctc   1740

aactccaagt tgtagatttg gtgtcttcct tgttcttact ttaaaaagtc atgtgttaat   1800

tttttttctg cctgtatttg tatgcaaaat gtcctctatc tgctattaaa gaaaagctac   1860

gtaaaacact acattgtaac cttctaagta ataataaata aaaagaaata tattgcagta   1920

acaatgggaa gtaagtatgt agttcttttg aaatatgtgg taaagaacta atcacagact   1980

atcatctaat ctggttacat attgtatttt tcatcctgaa taaaagtaat tttaacacaa   2040

aaaaa                                                               2045
```

<210> SEQ ID NO 57
<211> LENGTH: 23
<212> TYPE: DNA
<213> ORGANISM: Homo sapiens

<400> SEQUENCE: 57

```
ttgggaaagt gggtgggggc ttt                                             23
```

<210> SEQ ID NO 58
<211> LENGTH: 26

-continued

<212> TYPE: DNA
<213> ORGANISM: Homo sapiens

<400> SEQUENCE: 58
ataggttggg tgggttgggg ggcaag 26

<210> SEQ ID NO 59
<211> LENGTH: 25
<212> TYPE: DNA
<213> ORGANISM: Homo sapiens

<400> SEQUENCE: 59
gaccacttta catttttaca ttcct 25

<210> SEQ ID NO 60
<211> LENGTH: 22
<212> TYPE: DNA
<213> ORGANISM: Homo sapiens

<400> SEQUENCE: 60
ataggttggg tgggttgggg gg 22

<210> SEQ ID NO 61
<211> LENGTH: 24
<212> TYPE: DNA
<213> ORGANISM: Homo sapiens

<400> SEQUENCE: 61
aggttgggtg ggttgggggg caag 24

<210> SEQ ID NO 62
<211> LENGTH: 24
<212> TYPE: DNA
<213> ORGANISM: Homo sapiens

<400> SEQUENCE: 62
agccatgacc acctttctac ctca 24

<210> SEQ ID NO 63
<211> LENGTH: 24
<212> TYPE: DNA
<213> ORGANISM: Homo sapiens

<400> SEQUENCE: 63
atccattgca ttggaaactg cttt 24

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 64
cctttcgggt gaaagatcag 20

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 65
acttacttcc cattgttact gc 22

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 66
tctatgtcac tgcttctaca g 21

<210> SEQ ID NO 67
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 67
caccgtctat gtcactgctt ctacag 26

<210> SEQ ID NO 68
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 68
aaacctgtag aagcagtgac atagac 26

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 69
ggtacctcca cctacatctt t 21

<210> SEQ ID NO 70
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 70
caccgggtac ctccacctac atcttt 26

<210> SEQ ID NO 71
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 71
aaacaaagat gtaggtggag gtaccc 26

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 72
cataaagcag tttccaatgc a 21

<210> SEQ ID NO 73
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 73
caccgcataa agcagtttcc aatgca 26

<210> SEQ ID NO 74
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 74
aaactgcatt ggaaactgct ttatgc 26

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 75
gaagacacca aatctacaac t 21

<210> SEQ ID NO 76
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 76
caccggaaga caccaaatct acaact 26

<210> SEQ ID NO 77
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 77
aaacagttgt agatttggtg tcttcc                                      26

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
agtagcacct ctccccaggt                                             20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ctgaggcagg aagcttgaac                                             20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ttgcaattgt ttttggcatc                                             20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ctatgcccaa atagccaagg                                             20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
acaatgagcc cttacccaga                                             20

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gcatctcgtg tctcaacatc a                                           21

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 84
gccaggaagt ccaagatcag 20

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 85
gcaaacatcg ttttgtgaag g 21

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 86
tgcacacaag gtaagccaaa 20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 87
gaaccagggg agtgatctga 20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 88
ccctcatcac aggcagtttt 20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 89
ttcactcggt gtttctgacg 20

-continued

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 90
aaaaagaccc acccatcctt 20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 91
caacagcgca agactctgtc 20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 92
ctgatgccca cctgctaagt 20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 93
ggctgtggtg agccattatt 20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 94
tgcagtgagc tgagaccttg 20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 95
agggctagta gggagcgtgt 20

```
<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96

tacccaaggt ggagatcctg                                                20


<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97

atagatcatg ggcggttcag                                                20


<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98

caaaggcaaa caacccactt                                                20


<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99

tctgctggag gctgaggtat                                                20


<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100

cagtgccatc cagtacatcg                                                20


<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101

aggttgtggg catctgtagg                                                20


<210> SEQ ID NO 102
```

<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 102
cccaaggtgg agatcctg 18

<210> SEQ ID NO 103
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 103
ccgctgtagt ccatcatgc 19

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 104
gagtcaacgg atttggtcgt 20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 105
gacaagcttc ccgttctcag 20

<210> SEQ ID NO 106
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 106
tgttactgct tctacagaag aatgaa 26

<210> SEQ ID NO 107
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 107
actccaagtt gtagatttgg tgtctt 26

<210> SEQ ID NO 108
<211> LENGTH: 41

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108

agtctatgtc acwggcttct atgtagattt ggwgtcttcc t                     41
```

TROPHIN GENOME EDITING FOR TREATING DUCHENNE MUSCULAR DYSTROPHY (DMD)

CROSS-REFERENCE TO RELATED APPLICATIONS

This application is a National Phase Application of PCT International Application No. PCT/US2021/043185, International Filing Date Jul. 26, 2021, claiming the benefit of U.S. Patent Application(s) No(s). 63/056,397, filed Jul. 24, 2020, which is/are hereby incorporated by reference.

SEQUENCE LISTING

The instant application contains a Sequence Listing which has been submitted electronically in ASCII format and is hereby incorporated by reference in its entirety. Said ASCII copy, created on Sep. 17, 2021, is named P-580373-PC_SL.txt and is 25,940 bytes in size.

FIELD OF THE INVENTION

The present disclosure relates to methods and compositions for Utrophin genome editing for increasing utrophin protein production and for treating myopathies, such as Duchenne Muscular Dystrophy (DMD).

BACKGROUND OF THE INVENTION

Duchenne Muscular Dystrophy (DMD) is one of a group of muscular dystrophies characterized by the enlargement of muscles. DMD is one of the most prevalent types of muscular dystrophy and has rapid progression of muscle degeneration, which occurs early in life. DMD is a fatal, genetic disease affecting all world populations equally, and estimated to affect 1 in 3500 live-born males.

DMD is caused by genetic mutations in the DMI) gene leading to quantitative and qualitative disturbances in the expression of the dystrophin protein. The gene for DMD, found on the X chromosome, encodes a large protein-dystrophin. Dystrophin is required inside muscle cells for structural support: it is thought to strengthen muscle cells by anchoring elements of the internal cytoskeleton to the surface membrane and external structures. Without it, the muscle cannot produce force effectively and is susceptible to damage during contraction, eventually leading to muscle death and replacement by fatty and fibrous tissue. The accompanying immune response can add to the damage.

A mouse model for DMD exists, and is proving useful for furthering understanding both normal dystrophin function and the pathology of the disease. Specifically, experiments enhancing production of utrophin, a dystrophin relative, in order to compensate for dystrophin loss are promising, and may lead to effective therapies for this devastating disease.

Dystrophin is a member of the spectrin superfamily, which includes the spectrins, the a-actinins and three close relatives of dystrophin, the chromosome 6-encoded dystrophin related protein, Utrophin or DRP, the chromosome-X encoded, DRP 2 and the chromosome-18 encoded, dystrobrevin. A variety of animal models have been described that recapitulate the molecular lesions, of which the mouse and canine disease models (e.g. mdx mouse, GRMD dog) and are considered extremely valuable for preclinical studies and drug development. Utrophin is the autosomal homolog of dystrophin. Utrophins expression continues unabated in DMD muscle while dystrophin is severely reduced or absent.

MicroRNAs (miRNAs) are small RNA molecules encoded in plant and animal genomes. These highly conserved, ~21-mer RNAs regulate gene expression by binding to the 3' or 5'-untranslated regions (3'-UTR or 5'-UTR) of specific mRNAs.

Although miRNA was first described well over a decade ago, only recently has the breadth and diversity of this class of small, regulatory RNAs been appreciated. Much effort has gone into understanding how, when, and where miRNAs are produced and function in cells, tissues, and organisms. Each miRNA is thought to regulate multiple genes, and since hundreds of miRNA genes are predicted to be present in higher eukaryotes the potential regulatory circuitry afforded by miRNA is enormous.

MicroRNAs may act as key regulators of processes as diverse as early development, cell proliferation and cell death, apoptosis and fat metabolism, and cell differentiation. Studies of miRNA expression implicate them in brain development, chronic lymphocytic leukemia, colonic adenocarcinoma, Burkett's Lymphoma, and viral infection, suggesting possible links between miRNAs and viral disease, neurodevelopment, and cancer. miRNAs are differentially expressed in myopathies and have been implicated in heart disease. Accordingly, a need exists to determine the role of miRNAs in utrophin production to treat myopathies or utrophin mediated diseases.

Accordingly, there remains a need for effective therapeutic compositions and methods for treating myopathies, such as DMD, by enhancing or increasing utrophin protein production.

SUMMARY OF THE INVENTION

In one embodiment, the present disclosure provides methods and compositions for enhancing or upregulating utrophin expression in a subject by CRISPR-cas9 based genome editing of let-7c microRNA (miRNA) binding site and other miRNA binding sites in the 3' untranslated region (UTR) of the utrophin gene.

In one aspect, provided herein are methods for improving a dystrophic phenotype in a human subject having Duchenne Muscular Dystrophy (DMD), the method comprising: CRISPR-cas9 based genome editing a 3' untranslated region (UTR) of a utrophin gene to delete one or more microRNA (miRNA) binding sequences in the 3'-UTR, wherein the deletion of the one or more miRNA binding sequences alleviates miRNA-mediated repression and upregulates utrophin expression, thereby improving the dystrophic phenotype in the human subject. In some embodiments, the one or more miRNA binding sequences comprise a let-7c microRNA (miRNA) binding sequence.

Utrophin upregulation is a therapeutic strategy for DMD. Normally, Utrophin-A expression is repressed through the 5'- and 3'-UTRs by >98% at the translational level. The Utrophin 5'- and 3'-UTRs contain microRNA (miRNA) target sites. Utrophin 3'-UTR exhibits its inhibitory effect both on IRES and on cap-dependent translation. Provided herein is a method for CRISPR-cas9 based genome editing a let-7c microRNA (miRNA) binding sequence in a 3' untranslated region (UTR) of the utrophin gene to delete the let-7c miRNA binding site for therapeutic strategies for DMD (FIGS. 2, 3, 6 and 7).

In another aspect, provided herein are methods for treating Duchenne Muscular Dystrophy (DMD) in a human subject, the method comprising: CRISPR-cas9 based genome editing a 3' untranslated region (UTR) of a utrophin gene to delete one or more microRNA (miRNA) binding sequences in the 3'-UTR, wherein the deletion of the one or more miRNA binding sequences alleviates miRNA-mediated repression and upregulates utrophin expression, thereby improving the dystrophic phenotype in the human subject. In some embodiments, the one or more miRNA binding sequences comprise a let-7c microRNA (miRNA) binding sequence.

In another aspect, provided herein are pharmaceutical compositions provides a pharmaceutical composition comprising an adenoviral vector comprising a pair of short guide RNAs (sgRNAs), the pair of sgRNAs targeting for deletion one or more miRNA binding sequences in the 3'-UTR of a utrophin gene; and at least one pharmaceutically acceptable excipient. In some embodiments, the one or more miRNA binding sequences comprise a let-7c microRNA (miRNA) binding sequence.

Other features and advantages will become apparent from the following detailed description, examples, and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE FIGURES

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

FIG. 1 illustrates the high degree of similarity of organization and functional motifs between dystrophin and utrophin (from Moorwood & Khurana Expert Opinion Drug Discov. 2013).

FIGS. 2A-2B show a genome editing strategy for Utrophin upregulation. FIG. 2A illustrates how normally Utrophin protein is expressed to low levels as it is subject to miRNA mediated repression. FIG. 2B illustrates how CRISPR/Cas9-mediated editing (directed by a sgRNA pair) causes deletion of miRNA binding sites in the 3'UTR, resulting in utrophin upregulation.

FIG. 3A shows the locations of the miRNA's that bind the 3'UTR of human utrophin. FIG. 3B shows the locations of the miRNA's that bind the 3'UTR of mouse utrophin. Also shown (red bolts-numbered 1, 2, 4 and 5 in human utrophin gene and numbered 7, 12 and 13 in mouse utrophin gene) are sgRNAs, combinations of which will be used to edit the miRNA binding motifs.

FIG. 4A shows different human sgRNA-based CRISPR/Cas9 editing combinations and predicted post-editing (deletion) sizes. pX601-based constructs were transfected into HEK293T cells and DNA extracted 3 days post transfection. PCR was performed to validate editing success and determine efficiency. FIG. 4B shows PCR validation of successful utrophin gene editing with the sgRNA 1/5 combination with greatest efficiency.

FIG. 5A (top panel) shows wild type sequence with red bolts marking the sgRNA 7 & 13 positions of the area targeted for genome editing. miRNA binding sites are also marked. FIG. 5B (bottom panel) shows sequencing validation for editing of the mouse utrophin gene using the sgRNA 7 & 13 combination to delete a 435 bp region in the 3'UTR of the Utrophin gene using CRISPR/Cas9 editing.

FIG. 9A is a schematic diagram of (/TRN gene showing relative positions of five inhibitory miRNA target sites (miR-150, miR296-5p, miR-133b, let-7c and miR-196b) located in the 3'UTR. The iMTR is shown as a block. The SaCas9 sgRNA target sites shown as open arrows are designed flanking the iMTR. FIG. 9B shows a scheme of HEK 293T cell transfection with a plasmid construct (p-UTRNAiMTR) containing SaCas9 and dual sgRNAs (sg) followed by genomic DNA isolation and PCR screening for UTRNΔiMTR. FIG. 9C shows a scheme showing PCR strategy for identifying sgRNA pairs to efficiently achieve UTRNΔiMTR editing. The lightning bolts show SaCas9 cut sites. FIG. 9D is a DNA gel showing genomic PCR analysis from HEK 293T cells transfected with different combinations of sgRNA pairs. The larger PCR products (800 bp) are from unedited (JTRN and shorter PCR products (250-350 bp) are from UTRNΔiMTR gene.

FIG. 10A shows fluorescence and bright-field microscopy images of GFP expression in DMD-hiPSC cells transfected with SaCas9-GFP/sgRNA 1 & 4. Scale bar 200 μm. FIG. 10B shows FACS sorting of GFP positive DMD-hiPSC cells gated against mock transfected DMD-hiPSC cells. FIG. 10C shows genomic DNA PCR gel from clonally selected, genome edited, DMD-hiPSC cell lines with a 267 bp band from UTRNΔiMTR gene (UTRNΔiMTR clones a, b, c). FIG. 10D shows DNA sequencing of PCR product from UTRNΔiMTR clone having precise (533 bp) deletion of iMTR compared to sham edited clone. FIG. 10D discloses SEQ ID NOS 106-108, respectively, in order of appearance.

FIG. 10E shows representative western blot of utrophin in DMD-hiPSC sham edited and UTRNΔiMTR clones. α-Tubulin was used as loading control. FIG. 10F shows densitometric analysis of utrophin western blot to quantify utrophin upregulation. Bands were densitometrically quantified and utrophin normalized to α-Tubulin. Bars represent mean±SEM (n=4). Difference in utrophin expression between clones were statistically analyzed by the Mann- Whitney test (*P≤0.05). Significant increase in utrophin expression was observed in UTRNΔiMTR clones 2, 3 and 5 compared to sham edited clones with P value 0.028.

FIG. 12A is a schematic of myogenic differentiation of hiPSCs achieved by lentivirus mediated MyoD overexpression. FIG. 12B shows differentiated wild type, DMD and UTRNΔiMTR myotubes were stained with DAPI (blue) and MYHC (green). Scale bar=200 μm. FIG. 12C shows efficiency of myogenic differentiation determined as fusion index (percentage of MYHC-positive myotubes with more than 2 nuclei). A total of 85, 98 and 80 myotubes of wild type, DMD and UTRNΔiMTR respectively were counted. Average from three wells (three random fields from each well) with±SEM are shown. FIG. 12D shows gene expression analysis by qPCR of MyoD infected UTRNΔiMTR clones not treated with tamoxifen (day 0) or treated with tamoxifen for 4 or 8 days. Expression of pluripotency marker NANOG, skeletal muscle marker MyoD1, MyoG and endogenous MyoD1 are shown (n=3).

FIG. 13A shows wild type, DMD and UTRNΔiMTR differentiated myotubes were stained with DAPI (blue), MYHC (green) and a-sarcoglycan (red). Region highlighted by the white box was magnified (2.5×) and shown as inset. Scale bar=200 μm. FIG. 13B shows a-sarcoglycan quantification in wild type, DMD and UTRNΔiMTR differentiated myotubes. The a-sarcoglycan intensity shown as percentage expression mean±SEM was calculated as median of line intensity profile (n=20) in ImageJ and normalized with DAPI expression. Differences in a-sarcoglycan expression between individual groups were analyzed by the Kruskal-Wallis multiple comparison test. The P value is <0.0001. FIG. 13C shows Western blot of a-sarcoglycan expression in wild type, DMD and UTRNΔiMTR myotubes. Vinculin was used as loading control.

FIG. 17A shows representative western blot of utrophin expression in wild type, DMD and edited UTRNΔiMTR myotubes. «-Tubulin was used as loading control.

FIG. 17B shows densitometric analysis of the utrophin western blot to quantify utrophin expression in the myotubes. Bars represent mean±SEM (mean from three different experiments with three different wells each, n=9). Difference in utrophin expression between DMD and UTRNΔiMTR myotubes were statistically analyzed by Kruskal-Wallis test (*P=0.04).

DETAILED DESCRIPTION OF THE INVENTION

Figure 3A:
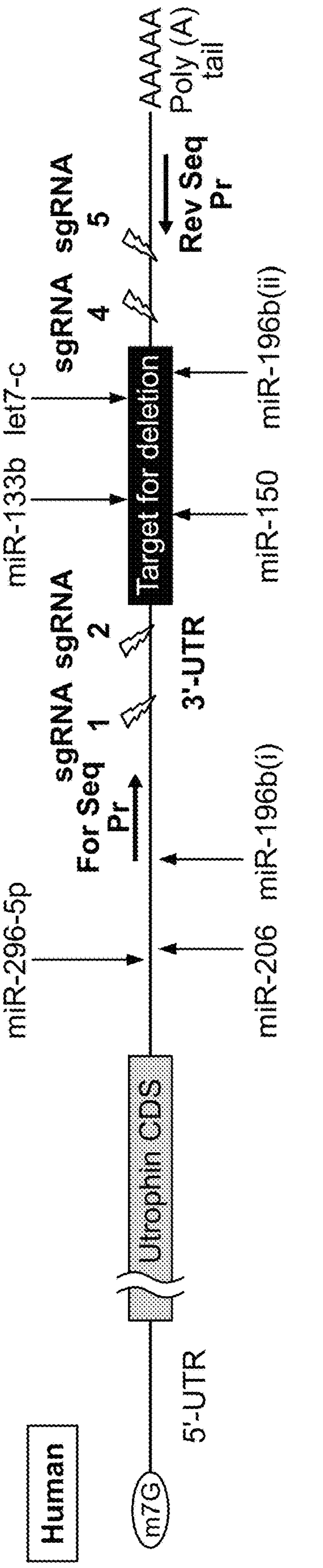
FIGS. 3A-3B show schematics of miRNA-binding sites and sgRNA positions for editing the Utrophin gene.

DMD is a fatal X-linked disease caused by mutations in the DMD gene causing an absence or severe reduction of the gene product, dystrophin. This orphan disease is characterized by muscle degeneration leading to progressive loss of mobility and death in the twenties, typically of respiratory or cardiac failure. These devastating consequences, for both patients and families, provides a great impetus for worldwide efforts toward identifying a cure for the disease. Currently, a number of dystrophin-based approaches such as gene therapy using Adeno-associated virus (AAV) based-dystrophin gene delivery, stem cells and dystrophin exon skipping using splice-skipping 20MePS and morpholino oligonucleotides (SSOs) are in various stages of preclinical and clinical development. An exciting development has been to use genome editing rather than SSOs to achieve exon skipping to circumvent the potential toxicity of SSOs. Irrespective of the methodology used, dystrophin-based approaches face a fundamental limitation in terms of the immune reactions that would be raised by the patient's immune system against dystrophin limiting their long-term efficacy.

An alternative approach to dystrophin-based DMD therapy, is by upregulating Utrophin, the autosomal homolog of dystrophin, expression. Utrophin upregulation (in contrast to dystrophin-based approaches) circumvents the immunological problems related to expressing dystrophin in DMD patients. Indeed, transgene, viral vector or promoter transactivator-based utrophin overexpression has been shown to improve the dystrophic phenotype of the mdx mouse model of DMD, without any overt toxicity. While promoter activation would certainly be predicted to increase utrophin expression, it has been demonstrated that utrophin is subject to significant repression at the translational level via multiple microRNAs (miRNAs). More recently it was shown that blocking let-7c miRNA binding sites in the Utrophin 3'-UTR using 20MePS oligonucleotides is sufficient to alleviate the repression, upregulate utrophin expression and, improve dystrophic pathophysiology in the mdx mouse model in vivo.

The advent of CRISPR-Cas9 based genome editing combined with AAV-based delivery and/or stem cell (SC)-based delivery offer an exciting approach to achieve therapeutic levels of utrophin upregulation in skeletal muscle, in vivo. CRISPR-Cas9 based genome editing has been utilized to target and edit out (delete) let-7c and other miRNA binding sites in the 3'-UTR of the Utrophin gene in both C2C12 mouse and HEK human cell lines. A major advantage of utrophin based gene editing approaches is that rather than a small subset of DMD patients that could benefit using exon-skipping by genome editing or SSO's, utrophin upregulation promises to benefit all DMD patients.

In one aspect, provided herein are methods of enhancing utrophin protein production in a cell, comprising the step of deleting one or more miRNA binding sequences in the 3'-UTR of a utrophin gene. In one embodiment, the one or more miRNA binding sequences comprise a let-7c microRNA (miRNA) binding sequence. In one embodiment, the cell is a stem cell or a muscle cell.

In one aspect, provided herein are methods for improving a dystrophic phenotype in a human subject having Duchenne Muscular Dystrophy (DMD), the method comprising: CRISPR-cas9 based genome editing a 3' untranslated region (UTR) of a utrophin gene to delete one or more microRNA (miRNA) binding sequences in the 3'-UTR, wherein the deletion of the one or more miRNA binding sequences alleviates miRNA-mediated repression and upregulates utrophin expression, thereby improving the dystrophic phenotype in the human subject. In some embodiments, the one or more miRNA binding sequences comprise a let-7c microRNA (miRNA) binding sequence.

In an embodiment, the CRISPR-cas9 based genome editing comprises:

(a) constructing an adenoviral vector comprising a pair of short guide RNAs (sgRNAs), the pair of sgRNAs targeting the let-7c miRNA binding sequence in 3'-UTR for deletion; and (b) administering the constructed adenoviral vector to the human subject.

In another embodiment, the pair of sgRNAs is sgRNA1 and sgRNA5, wherein the sgRNA1 and the sgRNA5 are each within 1-15 base pairs of the let-7c miRNA binding sequence.

In still another embodiment, the pair of sgRNAs is sgRNA1 and sgRNA4, wherein the sgRNA1 and the sgRNA4 are each within 1-15 base pairs of the let-7c miRNA binding sequence.

In a further embodiment, the pair of sgRNAs is sgRNA2 and sgRNA5, wherein the sgRNA2 and the sgRNA5 are each within 1-15 base pairs of the let-7c miRNA binding sequence.

In yet another embodiment, the pair of sgRNAs is sgRNA2 and sgRNA4 wherein the sgRNA2 and the sgRNA4 are each within 1-15 base pairs of the let-7c miRNA binding sequence.

As used herein the constructed adenoviral vector is also called an "editing construct". In a further embodiment, the method further comprises inserting an enhanced green fluorescent protein (EGFP) gene in the constructed adenoviral vector in step (a) to EGFP-tag the constructed adenoviral vector.

In an embodiment, the constructed adenoviral vector is transfected into human stem cells prior to administration to the human subject.

In another embodiment, the stem cells are human induced pluripotent stem cells (hiPSCs). CRISPR-Cas9 based genome editing of the miRNA-binding sites in the 3'UTR of the utrophin in DMD hiPSCs provided herein offers a novel strategy to "repress the repression" and achieve utrophin upregulation in DMD patients in vivo.

In a further embodiment, the stem cells are human muscle stem cells.

In still other embodiments, the let-7c microRNA binding sequence is either SEQ ID NO: 62 or SEQ ID NO: 18.

In further embodiments, the one or more microRNA binding sequences is selected from the group consisting of miR-133b, miR-150, miR-196b, miR-206, and miR-296-5p binding sequences. In further embodiments, the one or more microRNA binding sequences is the let-7c miRNA binding sequence and one or more miRNA binding sequences selected from the group consisting of miR-133b, miR-150, miR-196b, miR-206, and miR-296-5p binding sequences.

In an embodiment, the constructed adenoviral vector is administered to the human subject in vivo.

In another embodiment, the constructed adenoviral vector is administered to the human subject in utero.

In various embodiments, the administered constructed adenoviral vector may be the constructed adenoviral vector, e.g., the editing construct constructed in step (a). The editing construct may be untagged. In other embodiments, the administered constructed adenoviral vector may be the EGFP-tagged constructed adenoviral vector.

In a further embodiment, the improved dystrophic phenotype is selected from the group consisting of skeletal or cardiac muscle degeneration, skeletal or cardiac muscle weakness, skeletal muscle cramps or pain, respiratory impairment, cardiomyopathy and dystrophin abnormalities in the brain.

In another embodiment, the dystrophin abnormalities in the brain are attention focusing, verbal learning and memory and emotional interaction.

In another aspect, provided herein are methods for treating Duchenne Muscular Dystrophy (DMD) in a human subject, the method comprising: CRISPR-cas9 based genome editing a 3' untranslated region (UTR) of a utrophin gene to delete one or more microRNA (miRNA) binding sequences in the 3'-UTR, wherein the deletion of the one or more miRNA binding sequences alleviates miRNA-mediated repression and upregulates utrophin expression, thereby improving the dystrophic phenotype in the human subject. In some embodiments, the one or more miRNA binding sequences comprise a let-7c microRNA (miRNA) binding sequence.

In an embodiment, the CRISPR-cas9 based genome editing comprises:

(a) constructing an adenoviral vector comprising a pair of short guide RNAs (sgRNAs), the pair of sgRNAs targeting the let-7c miRNA binding sequence in 3'-UTR for deletion; and (b) administering the constructed adenoviral vector to the human subject.

In another embodiment, the pair of sgRNAs is sgRNA1 and sgRNA5, wherein the sgRNA1 and the sgRNA5 are each within 1-15 base pairs of the let-7c miRNA binding sequence.

In still another embodiment, the pair of sgRNAs is sgRNA1 and sgRNA4, wherein the sgRNA1 and the sgRNA4 are each within 1-15 base pairs of the let-7c miRNA binding sequence.

In a further embodiment, the pair of sgRNAs is sgRNA2 and sgRNA5, wherein the sgRNA2 and the sgRNA5 are each within 1-15 base pairs of the let-7c miRNA binding sequence.

In yet another embodiment, the pair of sgRNAs is sgRNA2 and sgRNA4 wherein the sgRNA2 and the sgRNA4 are each within 1-15 base pairs of the let-7c miRNA binding sequence.

In yet another embodiment, the method further comprises inserting an enhanced green fluorescent protein (EGFP) gene in the constructed adenoviral vector in step (a) to EGFP-tag the constructed adenoviral vector.

In an embodiment, the constructed adenoviral vector is transfected into human stem cells prior to administration to the human subject.

In another embodiment, the stem cells are human induced pluripotent stem cells (hiPSCs).

In a further embodiment, the stem cells are human muscle stem cells.

In still other embodiments, the let-7c microRNA binding sequence is either SEQ ID NO: 62 or SEQ ID NO: 18.

In further embodiments, the one or more microRNA binding sequences is selected from the group consisting of miR-133b, miR-150, miR-196b, miR-206, and miR-296-5p binding sequences. In further embodiments, the one or more microRNA binding sequences is the let-7c miRNA binding sequence and one or more miRNA binding sequences selected from the group consisting of miR-133b, miR-150, miR-196b, miR-206, and miR-296-5p binding sequences.

In an embodiment, the constructed adenoviral vector is administered to the human subject in vivo.

In another embodiment, the constructed adenoviral vector is administered to the human subject in utero.

In some embodiments, the administered constructed adenoviral vector may be the constructed adenoviral vector, e.g., the editing construct constructed in step (a). The editing construct may be untagged. In other embodiments, the administered constructed adenoviral vector may be the EGFP-tagged constructed adenoviral vector.

In a further embodiment, the treatment improves or alleviates skeletal or cardiac muscle degeneration, skeletal or cardiac muscle weakness, skeletal muscle cramps or pain, respiratory impairment, cardiomyopathy and dystrophin abnormalities in the brain.

In still further embodiments, the dystrophin abnormalities in the brain are attention focusing, verbal learning and memory and emotional interaction.

In another aspect, provided herein are pharmaceutical compositions provides a pharmaceutical composition comprising an adenoviral vector comprising a pair of short guide RNAs (sgRNAs), the pair of sgRNAs targeting for deletion one or more miRNA binding sequences in the 3'-UTR of a utrophin gene; and at least one pharmaceutically acceptable excipient. In some embodiments, the one or more miRNA binding sequences comprise a let-7c microRNA (miRNA) binding sequence.

In an embodiment, the adenoviral vector is transfected into human stem cells prior to administration to the human subject.

In still another embodiment, the stem cells are human induced pluripotent stem cells (hiPSCs).

In additional embodiments, the stem cells are human muscle stem cells. The human muscle stem cells may differentiate into skeletal muscle or into cardiac muscle.

In some embodiments, the expression of utrophin in a muscle cell is increased over basal levels by about 10%, 20%, 25%, 30%, 40%, 50%, 60%, 70%, 75%, 80%, 90% or more. In some embodiments, the expression of utrophin in a muscle cell is increased over basal levels by about 2-fold, 3-fold, 4-fold, 5-fold, 10-fold, 20-fold, 25-fold, 30-fold, 40-fold, 50-fold, 75-fold, 100-fold or more.

The wild-type mouse (*Mus musculus*) utrophin mRNA sequence can be found in GenBank (accession number AK035043.1). The mouse utrophin mRNA 3'-UTR has the following nucleotide sequence (the Let-7c microRNA binding sequence/binding site is in bold and underlined):

(SEQ ID NO: 13)
TGAGCATCTATCCAGCCAGCCAACATTTCCCGACCTTCAGTATTGCCCT
CTTCTGCAAATGCCAATCCCAAGACCCATTCAACCCCAAAGCTCCGTGG
CTCCACGACACAAGCTGTTGAGTGCTTACTGGGTGTTCTACTGAGGGAA

-continued

CCAAACACTGACTATCCAAAGAGAAAAGGATATTTTGGTTTTCTAATAA
CGTATATTATTGTTTTCTTCTCCCCTTTCTATGCAACTGTAAATTAATG
AACAGAGAAGTATTTGGAGGTGGTAAAGCATTTGTCACTGATTTGTATA
ATATATACAGCCATGGGAAAGTGGGTGGGGGCTTTCTAATATGAAACTG
TCTTTTTAATAACCAAGAGAAAAAATTGCATAAGAATTAGACCACTTTA
CATTATTACATTCCTTCTGCTGTTCACATTAACCTTGTACAATAACTTC
ACTTATTATTTGACTGTTTTACCATTATGTTTTGGTTATTTATAAATTT
ATCAGCCATACAAACAAATAGATTCTATGTATTTGTTTCTATAATCTGG
CCAAATTCCTAAGTTCATATATTTGAATCAAATATTTTACATATGTGGA
GTAGGCAGGCATTCTGAAGATACTATTTAACTTTAGTTGACGTCACACA
CACCATCCTTTAGTAACCACTGGATGACTACACTAAAAATCCTGTGGAC
TTTAACGGCAAGCTGCTGGGGTATTTTTCCTCCTGTTTTTATTCCTTTT
TTGTAAGTAGATCTTGACGTCTTTATTTATTTCATCTTGCAATCTCTAT
AATAAAGAAGACTGTATTGTAATAGTCTCAAAAAATTATTTTACCAAGG
GTTACCATTTAAGCATATTTTCATTTTGATTCAGAAACCAAAGTTGGTA
CAACCTCTCCTAGTACATGCAACCTTGGTTTTCATGAGAAAACACACGG
CAGGCCTTTGCCCATTGTGAGGAGAGCACACATCATGCTCTTCAGTTTC
CTTTGAATAGACTTTTATTGTTGTTTTTGTATTTTTCGAGTCCTGTGTA
AGTTTTGAAAGCTCTGGTTGTTTCCTTTGTGAAAGCAGGCAGATACTTA
GTTGGCTGTCTCATTTGAAGCTTTGGAGCAGATAGTCAGATGTCTCATG
ACCCCTCACTTGGCCAGCAGCACATCCGAGAAGGATGTCACTCACAAGC
CTACACCACGGCTTCTCTAGAATGAAATCAGTGCTCGGATGATTGTATC
CCTGCCTCTACTTCTGAGTGTGTTCAACTAGGTATTGGCTTCTTTTTCT
TTTTCTTTTCTTTTTTTTTTAATTTAACACTTAATTGCCGATTTTAGAG
AAACCAAAAATAAAGGTGAAGGTAATATGTTTTGATTCAAACATATATG
CTTTTAAACATCAGACATGCTAACTTTGGTTCTCTTTACTGGAATCTGG
CCCAGAGGAGGTGAAATTTAGAAATGTTATTCTTTAGATGGGTGGGTGG
GTTGGGGGGCCAAGGGTGTCTATTTTCCAGCATTAGATATTTTTGAGAC
GAAGAAAATTGTTTTATATAAGGGGAGAGCCATGATCACCTTTCTACCT
CAGAACCACCTTCCTCCATTGTGTTGGACATAGCTTTATATGCCGCAGT
GTGCAAAACCTAGGGCTGTAGTCAGGCCTTTCCATACCCAGGAAGCACC
TGTGTAAAGAAGATCAACAGAAACTCCCGGAACTCAGAACCCCAAGTTG
TAGATTTGGTGTCGTCCTTGTTCTTGCTTTGAGGAGTCATGTATTCTTT
TATTTCCTGCCTGTATTTGTATGCAAAATGATCTCTATCTGCTATTACA
GAAAAAGCTACACAAAACACTACATTGTAACCTTCTGAGTAATAAATAA
GAGGAAATATATTACAGTAACCATGATGAGAAATAAGTGTATTGTTCTT
TTGAAATATGTGGTTAATCGCAGACTGTCATCTAATCTGTTACATACCG
TATTTTTCATCCTGAATAAAAGTAATTTTAACACAAAATGACTTTGATG
TTTGGCTGTGTTCAGCTGATGAAATCAGATCTCTGAATGTATGTGATGA
AAGCTAACTATAAGATGATCTATATTCTGATAAATCTAAATATTTTCTG

-continued

AAACTCTCTCTTATACATTAATCTAGTCTCCATTCACTCATTATCTCTC

TCTCCTTTCTTGCATATAAATATGATTATATATTTTTCAATTTCCTGTA

CAAATCAGAGTCTTATTACTAGGGAAAATGGATGTTATAAGTACATTCC

TAAAGCCCATTGGGCCTTCATTTTTATAACTTGGAGCTACTGAGATTTA

TCAGGTTACTCTCTCAAATCCACTTTCATCACTAGACTCATAGTTTTCT

ATGTATCTATATTATTATAACTAAATAAAAATATACATG.

The wild-type human (*Homo sapiens*) utrophin mRNA sequence can be found in GenBank (accession number NM_007124.2). The human utrophin mRNA 3'-UTR has the following nucleotide sequence (the Let-7c microRNA binding sequence/binding site is in bold and underlined):

(SEQ ID NO: 56)

TGAAGTATTCATCCGGCCAACCAATGTTTCCTGACGTACAGTGTTGCCC

TTTTCAGCAAATGCCAATTCCAAGTTCCATTAAATCAGAAGCTCCATGG

CTCCTTGGCCCACGATGTTGAGTGCTGACTGTGTGTTCTACTGAAAGAG

TAAAACACTGACTATCCAAAGAGAAATGGATATTTTGTTTTTATAATAA

CCATATATTATTGTTTTCTTCTTCCCTTTCTATGCAAGTGTAAATTAAT

GAACAGAGAGGTATTTGGAAATGGTAATACATTTGTCACGGATTTGTAT

AATGTATACAGCATTGGGAAAGTGGGTGGGGGCTTTCTAATATGATACC

GTCTTTTTAATAACTATGACAAAGCTTACATAAGAATTAGAAGACCACT

TTACATTTTTACATTCCTTCTGCTGTTCATATTAACCTTGCACAATTAC

TTCATTTTTTCTTTGACTCTTTTACCACAATGTTTTGGTTATTTATAAT

TTATCAGCCATATGTTTATCAGCCATATAACCAACTAGATCCCAAATAG

ATCCATGTATTTGTTTCCGTGATTTGGCCACATTAATAAATTCATAAAT

TTCAATCAAATATCTTATATATACACACATATGGTTTAAGCTACAGCCC

TGTGTATGCCGTTTAACTTTATTTGACGTTGCCCACTTACTTCTTTGCT

GACCACTTGGATAACCGTAATAAAAATCCTATAAGCCTAAATGGCATTT

CTTTTGGGATATTTTTCCTGCATTTTATTCCCTTTTTATATAAGTAGGA

ATTAATTATTTATTTTATGTCTTAATCTATTTGATAAAGAAGACTACAT

TATAATAATCTCAAAGATCATATTACCAAAGGTTGCCCACTTGAGCATA

TTTTCATTTTGACACAGAAACAAAATTTAGTACAACCTTTCCTAGTTCC

CATGTCTTGATTTTCATCATTACATGCACAGCAGACCTTTACCTATTGT

GATACCAGAACACATCATTGTCTTTGGTTCCCTTCAAAGAGAATTTTAT

TGTTGTTTTGTATTTTCAAGTCCTTAATAGTTCTTGAAACTCCTAGTTG

TTTTCTTGTTGAAAGCAGACACACATTTAGTGCACGGCTTATTTTACCT

TTCGGGTGAAAGATCAGATGTTTTTATACCCTTCACTTGATCAATATAT

TTGGAAAGAATGTTTATCAAAAGTCTATGTCACTGCTTCTACAGAAGAA

TGAAATTAATGCTTAGGTGATGGTACCTCCACCTACATCTTTTTGAGTG

CATTCAATTATGTATTTTGGTTTAGCTTCTGATTTAACATTTAATTGAT

TCAGTTTAAACATGTTACTTAATTAGCAAATGTAGAGGAACCAAAAAAA

GGTGAAAATAATATGTTTTGATTCAAACCTAAAGACATAAAAACATAAA

GACATTTTAACTTTGGGTTCTCTTTAGCTGGGATCTGGCCAGAAGGAGG

-continued

CTTAAAGTTAGAAATTGCTATTATTTTAGAATAGGTTGGGTGGGTTGGG

GGGCAAGGGTGTCTATTTGCAGCAGAGATATTTTGAAAAGAAGAAAATT

GTTTTATATAAAAAGGAA<u>AGCCATGACCACCTTTCTACCTCA</u>GATCCAT

CTTCATCCATTGCATTGGAAACTGCTTTATGCTGCTGCAGTCTGCAAAG

TCTAGAGCTTTTATCAGGCCATGTCATACCCAAGAAAGCACCTATTTAA

AGAAAAAACAATTCCCTGAGCTCTCAACTCCAAGTTGTAGATTTGGTGT

CTTCCTTGTTCTTACTTTAAAAAGTCATGTGTTAATTTTTTTCTGCCT

GTATTTGTATGCAAAATGTCCTCTATCTGCTATTAAAGAAAAGCTACGT

AAAACACTACATTGTAACCTTCTAAGTAATAATAAATAAAAAGAAATAT

ATTGCAGTAACAATGGGAAGTAAGTATGTAGTTCTTTTGAAATATGTGG

TAAAGAACTAATCACAGACTATCATCTAATCTGGTTACATATTGTATTT

TTCATCCTGAATAAAAGTAATTTTAACACAAAAAAA.

In some embodiments, the utrophin mRNA 3'-UTR nucleic acid sequence is a homologue, variant, or functional fragment of SEQ ID NO: 13. In other embodiments, the utrophin mRNA 3'-UTR nucleic acid sequence is a homologue, variant, or functional fragment of SEQ ID NO: 56.

In mouse utrophin mRNA, the 3'-UTR has the following two miR-296-5p binding sequences: 5'-ATGGGAAAGTGGGTGGGGGCTTT-3' (SEQ ID NO: 14) and 5'-GGGTGGGTGGGTTGGGGGGCC-3' (SEQ ID NO: 23. In the mouse utrophin mRNA 3'-UTR, the miR-206 binding sequence: 5'-CCACTTTACATTATTACATTCC-3' (SEQ ID NO: 15). In the mouse utrophin mRNA 3'-UTR, the miR-150 binding sequence is: 5'-ATGGGTGGGTGGGTTGGGGG-3' (SEQ ID NO: 16). In the 3'-UTR of mouse utrophin mRNA, the miR-133b binding sequence is: 5'-GTGGGTTGGGGGGCCAA-3' (SEQ ID NO: 17). In the mouse utrophin mRNA 3'-UTR, the miR-196b binding sequence is: 5'-CCATACCCAGGAAGCACCT-3' (SEQ ID NO: 19). In of mouse utrophin mRNA 3'-UTR, the let-7c binding sequence is: 5'-AGCCATGATCACCTTTCTACCTCA-3' (SEQ ID NO: 18).

In human utrophin mRNA, the 3'-UTR has the following two miR-296-5p binding sequences: 5'-TTGGGAAAGTGGGTGGGGGCTTT-3' (SEQ ID NO: 57) and 5'-ATAGGTTGGGTGGGTTGGGGGGCAAG-3' (SEQ ID NO: 58). In the human utrophin mRNA 3'-UTR, the miR-206 binding sequence is: 5'-GACCACTTTACATTTTTACATTCCT-3' (SEQ ID NO: 59). In the human utrophin mRNA 3'-UTR, the miR-150 binding sequence is: 5'-ATAGGTTGGGTGGGTTGGGGGG-3' (SEQ ID NO: 60). In the human utrophin mRNA 3'-UTR, the miR-133b binding sequence is: 5'-AGGTTGGGTGGGTTGGGGGGCAAG-3' (SEQ ID NO: 61). In the human utrophin mRNA 3'-UTR, the miR-196b binding sequence is: 5'-ATCCATTGCATTGGAAACTGCTTT-3' (SEQ ID NO: 63). In the human utrophin mRNA 3'-UTR, the let-7c binding sequence is: 5'-AGCCATGACCACCTTTCTACCTCA-3' (SEQ ID NO: 62).

In some embodiments, the muscle cell is a skeletal muscle cell, a smooth muscle cell, a satellite muscle cell, or a cardiac muscle cell.

In some embodiments, the microRNA molecule is a muscle cell specific microRNA molecule. In some embodiments, the microRNA molecule binds to utrophin mRNA. In some embodiments, the microRNA molecule is complementary to a utrophin mRNA sequence. In some embodiments, the microRNA molecule is complementary to a utrophin 5'-UTR mRNA sequence. In other embodiments, the microRNA molecule is complementary to a utrophin 3'-UTR mRNA sequence. In some embodiments, the microRNA molecule decreases utrophin protein levels. In some embodiments, the microRNA molecule decreases utrophin protein levels without decreasing utrophin mRNA levels. In some embodiments, the microRNA molecule targets utrophin-A IRES. In some embodiments, the microRNA molecule targets utrophin-A IRES in a muscle cell. In some embodiments, the microRNA molecule represses utrophin-A IRES activity.

In some embodiments, the microRNA molecule is let-7c. In some embodiments, the microRNA molecule is selected from miR-206, miR-196b, miR-133b, miR-150, or miR-296-5p.

The let-7c microRNA (mouse sequence and human) is: 5'-UGAGGUAGUAGGUUGUAUGGUU-3' (SEQ ID NO: 1). In one embodiment, a let-7c microRNA antisense sequence or anti-Let-7c is: 5'-AACCAUACAACCUACUACCUCA-3' (SEQ ID NO: 2).

The miR-133b microRNA sequence (mouse and human) is: 5'-UUUGGUCCCCUUCAACCAGCUA-3' (SEQ ID NO: 3). In one embodiment, a miR-133b microRNA antisense sequence or anti-miR-133b is: 5'-UAGCUGGUUGAAGGGGACCAA-3' (SEQ ID NO: 4). The miR-150 microRNA sequence (mouse and human) is: 5'-UCUCCCAACCCUUGUACCAGUG-3' (SEQ ID NO: 5). In one embodiment, a miR-150 microRNA antisense sequence or anti-miR-150 is: 5'-CACUGGUACAAGGGUUGGGAGA-3' (SEQ ID NO: 6). The miR-196b microRNA sequence (mouse and human) is: 5'-UAGGUAGUUUCCUGUUGUUGGG-3' (SEQ ID NO: 7). In one embodiment, a miR-196b microRNA antisense sequence or anti-miR-196b is: 5'-CCAACAACAGGAAACUACCUA-3' (SEQ ID NO: 8). The miR-206 microRNA sequence (mouse and human) is: 5'-UGGAAUGUAAGGAAGUGUGUGG-3' (SEQ ID NO: 9). In one embodiment, a miR-206 microRNA antisense sequence or anti-miR-206 is: 5'-CCACACACUUCCUUACAUUCCA-3' (SEQ ID NO: 10). The miR-296-5p microRNA sequence (mouse and human) is: 5'-AGGGCCCCCCCUCAAUCCUGU-3' (SEQ ID NO: 11). In one embodiment a miR-296-5p microRNA antisense sequence or anti-miR-296-5p is: 5'-ACAGGAUUGAGGGGGGGCCCU-3' (SEQ ID NO: 12).

In some embodiments, the microRNA molecule let-7c comprises the sequence of miRbase (www.mirbase.org) accession number MI0000064, MI0000559, MI0000560, MI0000830, MI0000831, MI0001174, MI0001866, MI0001867, MI0002445, MI0004886, MI0005124, MI0005454, MI0007138, MI0007152, MI0007183, MI0007184, MI0007574, or MI0008076.

In some embodiments, the microRNA molecule miR-206 comprises the sequence of miRBase accession number MI0000249, MI0000490, MI0000948, MI0001207, MI0002045, MI0002046, MI0002619, MI0002620, MI0004863, MI0005317, MI0007667, or MI0008002. In some embodiments, the microRNA molecule miR-196b comprises the sequence of miRBase accession number MI0001150, MI0001151, MI0001152, MI0002036, MI0003365, MI0003366, MI0004943, MI0005313, MI0007660, or MI0008016. In some embodiments, the microRNA molecule miR-133b comprises the sequence of miRBase accession number MI0000821, MI0000822, MI0001206, MI0001994, MI0003490, MI0004837, or MI0007622. In some embodiments, the microRNA molecule miR-150 comprises the sequence of miRBase accession number MI0000172, MI0000479, MI0000920, MI0002016, MI0004846, MI0005058, MI0007122, MI0007123, MI0007124, MI0007125, MI0007126, MI0007127, MI0007128, MI0007641, or MI0007998. In some embodiments, the microRNA molecule miR-296-5p comprises the sequence of miRBase accession number MI0000394, MI0000747, or MI0007681.

In some embodiments, inhibiting let-7c, miR-196b, miR-133b, miR-150, miR-296-5p, miR-206, or a combination thereof leads to utrophin upregulation. In some embodiments, an inhibitor of let-7c, miR-196b, miR-133b, miR-150, miR-296-5p, miR-296, or a combination thereof is used as a Duchenne muscular dystrophy therapeutic agent.

In some embodiments, inhibiting a microRNA molecule comprises contacting a microRNA binding sequence in an mRNA with a complementary antisense oligonucleotide sequence, thereby blocking the interaction between the microRNA and its binding sequence within the mRNA. In some embodiments, inhibiting a utrophin microRNA molecule comprises contacting a microRNA binding sequence in a utrophin mRNA with a utrophin mRNA antisense molecule, thereby blocking the interaction between the microRNA and its binding sequence within the utrophin mRNA. In some embodiments, inhibiting a utrophin microRNA molecule comprises contacting a microRNA binding sequence in a utrophin mRNA with an antisense molecule that specifically binds to or hybridizes with the microRNA binding sequence, thereby blocking the interaction between the microRNA and its binding sequence within the utrophin mRNA.

In some embodiments, inhibiting a microRNA molecule comprises contacting a microRNA binding sequence within the 5'-UTR of an mRNA with a complementary antisense oligonucleotide sequence, thereby blocking the interaction between the microRNA and its binding sequence within the 5'-UTR of the mRNA. In some embodiments, inhibiting a utrophin microRNA molecule comprises contacting a microRNA binding sequence in the 5'-UTR of utrophin mRNA with an antisense molecule, thereby blocking the interaction between the microRNA and its binding sequence within the 5'-UTR of utrophin mRNA. In some embodiments, inhibiting a utrophin microRNA molecule comprises contacting the microRNA binding sequence in the 5'-UTR of utrophin mRNA with an antisense molecule that specifically binds to or hybridizes with the microRNA binding sequence, thereby blocking the interaction between the microRNA and its binding sequence within the 5'-UTR of utrophin mRNA.

In some embodiments, inhibiting a microRNA molecule comprises contacting a microRNA binding sequence within the 3'-UTR of an mRNA with a complementary antisense oligonucleotide sequence, thereby blocking the interaction between the microRNA and its binding sequence within the 3'-UTR of the mRNA. In some embodiments, inhibiting a utrophin microRNA molecule comprises contacting a microRNA binding sequence in the 3'-UTR of utrophin mRNA with an antisense molecule, thereby blocking the interaction between the microRNA and its binding sequence within the 3'-UTR of utrophin mRNA. In some embodiments, inhibiting a utrophin microRNA molecule comprises contacting the microRNA binding sequence in the 3'-UTR of utrophin mRNA with an antisense molecule that specifically binds to or hybridizes with the microRNA binding sequence, thereby blocking the interaction between the microRNA and its binding sequence within the 3'-UTR of utrophin mRNA.

In some embodiments, inhibiting interaction of a microRNA with its binding sequence in utrophin mRNA leads to utrophin upregulation. In some embodiments, inhibiting interaction of a microRNA with its binding sequence in utrophin mRNA leads to utrophin mRNA stabilization. In some embodiments, an inhibitor of the interaction of a microRNA with its binding sequence in utrophin mRNA is used as a Duchenne muscular dystrophy therapeutic agent.

In some embodiments, antisense oligonucleotides described herein contain a sequence that is complementary (in certain embodiments partially complementary, and in other embodiments exactly complementary) to a "target RNA." "Hybridization" as used herein refers to hydrogen bonding between complementary nucleotides. An oligonucleotide "specifically hybridizes" to a target polynucleotide if it hybridizes to the target under physiological conditions, with a $T_m$ substantially greater than 45° C., preferably at least 50° C., and typically 60° C.-80° C. or higher. Such hybridization preferably corresponds to stringent hybridization conditions. At a given ionic strength and pH, the $T_m$ is the temperature at which 50% of a target sequence hybridizes to a complementary polynucleotide. The degree of complementarity between an antisense oligonucleotide and its target sequence may be variable. Such hybridization may occur with "near" or "substantial" complementary of the antisense oligomer to the target sequence, as well as with exact complementarity. In some embodiments, the antisense oligonucleotide is exactly complementary to its target sequence. It is understood that it is not required that an antisense oligonucleotide be exactly complementary to its target sequence to achieve sufficient specificity, i.e. to minimize non-specific binding of the oligonucleotide to non-target sequences under the particular binding conditions being used (e.g., in vivo physiological conditions or in vitro assay conditions). "Target RNA" refers to an RNA molecule of interest, such as utrophin mRNA, which is the target for hybridizing with/binding to an oligonucleotide described herein.

In some embodiments, an antisense oligonucleotide comprises at least 3, at least 4, at least 5, at least 7, at least 9, at least 11, at least 13, or more than 13 consecutive nucleotides which are complementary to a utrophin microRNA molecule, such as a muscle cell utrophin microRNA, or a fragment thereof. In some embodiments, an antisense oligonucleotide comprises at least 3, at least 4, at least 5, at least 7, at least 9, at least 11, at least 13, or more than 13 consecutive nucleotides that are complementary to a microRNA molecule represented by a miRBase accession number as described hereinabove or a fragment thereof.

In some embodiments, an antisense oligonucleotide comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, or more than 26 consecutive nucleotides derived from the 5'-UTR or the 3'-UTR of a utrophin RNA molecule. For example, an antisense oligonucleotide derived from the 5'-UTR or the 3'-UTR of utrophin mRNA encompasses sequences that are complementary to sequences in the 5'-UTR or the 3'-UTR.

In some embodiments, an antisense oligonucleotide comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, or more than 26 consecutive nucleotides that are complementary to a utrophin microRNA, such as a muscle cell utrophin microRNA, binding site within utrophin mRNA. In some embodiments, the utrophin microRNA molecule is a microRNA represented by a miRBase accession number as described hereinabove or a fragment thereof. In some embodiments, an antisense oligonucleotide comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, or more than 26 consecutive nucleotides complementary to the 5'-UTR or the 3'-UTR of utrophin mRNA.

A homologous complementary sequence is at least 60% homologous, at least 70% homologous, at least 80% homologous, at least 90% homologous, at least 95% homologous, at least 98% homologous, at least 99% homologous, or even 100% homologous.

In some embodiments, an antisense oligonucleotide comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, or more than 26 consecutive nucleotides complementary to let-7c (e.g., a sequence set forth in SEQ ID NO: 2).

In some embodiments, an antisense oligonucleotide comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, or more than 26 consecutive nucleotides complementary to miR-196b (e.g., a sequence set forth in SEQ ID NO: 8), to miR-133b (e.g., a sequence set forth in SEQ ID NO: 4) to miR-150 (e.g., a sequence set forth in SEQ ID NO: 6), to miR-296-5p (e.g., a sequence set forth in SEQ ID NO: 12), or to miR-206 (e.g., a sequence set forth in SEQ ID NO: 10).

In some embodiments, an antisense oligonucleotide comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, or more than 26 consecutive nucleotides complementary to a let-7c binding sequence within utrophin mRNA.

In some embodiments, an antisense oligonucleotide comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, or more than 26 consecutive nucleotides complementary to a miR-196b binding sequence, to a miR-133b binding sequence, to a miR-150 binding sequence, to a miR-296-5p binding sequence, or to a miR-206 binding sequence within a utrophin mRNA.

In some embodiments, an antisense molecule is a synthetic peptide nucleic acid (PNA) or locked nucleic acid (LNA).

In another aspect, antisense oligonucleotides are provided that inhibit binding of Let-7 microRNA to its corresponding binding site in the utrophin mRNA 3'-UTR. In some embodiments, the heteroduplex formed by the oligonucleotide and the binding sequence is resistant to cleavage by RNase H. In some embodiments, the antisense oligonucleotide has a nucleic acid sequence set forth in SEQ ID NO: 24, a fragment thereof, or a variant thereof. In some embodiments, the antisense oligonucleotide has a nucleic acid sequence set forth in SEQ ID NO: 25, a fragment thereof, or a variant thereof. In some embodiments, a variant antisense oligonucleotide of SEQ ID NO: 24 or SEQ ID NO: 25 includes oligonucleotides where one or more additional bases have been added to and/or deleted from the 3' and/or 5' end. Examples of such oligonucleotides include, for example, the nucleic acid sequences set forth in SEQ ID NOs: 26-55.

Examples of a variant antisense oligonucleotide of SEQ ID NO: 24 include, for example, the nucleic acid sequences set forth in SEQ ID NOs: 26-40. Examples of a variant antisense oligonucleotide of SEQ ID NO: 25 include, for example, nucleic acid sequences set forth in SEQ ID NOs: 41-55. The nucleic acid sequences of SEQ ID NOs: 24-55 are listed in the Table 1 below.

TABLE 1

| SEQ ID NO: | SEQUENCE | Organism |
|---|---|---|
| SEQ ID NO: 24 | 5'-CUG AGG UAG AAA GGU GAU CAU GGC UC-3' | Mouse |
| SEQ ID NO: 25 | 5'-CUG AGG UAG AAA GGU GGU CAU GGC UU-3' | Human |
| SEQ ID NO: 26 | 5'-CUG AGG UAG AAA GGU GAU CAU GGC UCU-3' | Mouse |
| SEQ ID NO: 27 | 5'-CUG AGG UAG AAA GGU GAU CAU GGC UCU C-3' | Mouse |
| SEQ ID NO: 28 | 5'-CUG AGG UAG AAA GGU GAU CAU GGC UCU CC-3' | Mouse |
| SEQ ID NO: 29 | 5'-U CUG AGG UAG AAA GGU GAU CAU GGC UC-3' | Mouse |
| SEQ ID NO: 30 | 5'-UU CUG AGG UAG AAA GGU GAU CAU GGC UC-3' | Mouse |
| SEQ ID NO: 31 | 5'-GUU CUG AGG UAG AAA GGU GAU CAU GGC UC-3' | Mouse |
| SEQ ID NO: 32 | 5'-U CUG AGG UAG AAA GGU GAU CAU GGC UCU-3' | Mouse |
| SEQ ID NO: 33 | 5'-UU CUG AGG UAG AAA GGU GAU CAU GGC UCU-3' | Mouse |
| SEQ ID NO: 34 | 5'-GUU CUG AGG UAG AAA GGU GAU CAU GGC UCU-3' | Mouse |
| SEQ ID NO: 35 | 5'-U CUG AGG UAG AAA GGU GAU CAU GGC UCU C-3' | Mouse |
| SEQ ID NO: 36 | 5'-UU CUG AGG UAG AAA GGU GAU CAU GGC UCU C-3' | Mouse |
| SEQ ID NO: 37 | 5'-GUU CUG AGG UAG AAA GGU GAU CAU GGC UCU C-3' | Mouse |
| SEQ ID NO: 38 | 5'-U CUG AGG UAG AAA GGU GAU CAU GGC UCU CC-3' | Mouse |
| SEQ ID NO: 39 | 5'-UU CUG AGG UAG AAA GGU GAU CAU GGC UCU CC-3' | Mouse |
| SEQ ID NO: 40 | 5'-GUU CUG AGG UAG AAA GGU GAU CAU GGC UCU CC-3' | Mouse |
| SEQ ID NO: 41 | 5'-CUG AGG UAG AAA GGU GGU CAU GGC UUU-3' | Human |
| SEQ ID NO: 42 | 5'-CUG AGG UAG AAA GGU GGU CAU GGC UUU C-3' | Human |
| SEQ ID NO: 43 | 5'-CUG AGG UAG AAA GGU GGU CAU GGC UUU CC-3' | Human |
| SEQ ID NO: 44 | 5'-U CUG AGG UAG AAA GGU GGU CAU GGC UU-3' | Human |
| SEQ ID NO: 45 | 5'-AU CUG AGG UAG AAA GGU GGU CAU GGC UU-3' | Human |
| SEQ ID NO: 46 | 5'-GAU CUG AGG UAG AAA GGU GGU CAU GGC UU-3' | Human |
| SEQ ID NO: 47 | 5'-U CUG AGG UAG AAA GGU GGU CAU GGC UUU-3' | Human |
| SEQ ID NO: 48 | 5'-AU CUG AGG UAG AAA GGU GGU CAU GGC UUU-3' | Human |
| SEQ ID NO: 49 | 5'-GAU CUG AGG UAG AAA GGU GGU CAU GGC UUU-3' | Human |
| SEQ ID NO: 50 | 5'-U CUG AGG UAG AAA GGU GGU CAU GGC UUU C-3' | Human |
| SEQ ID NO: 51 | 5'-AU CUG AGG UAG AAA GGU GGU CAU GGC UUU C-3' | Human |
| SEQ ID NO: 52 | 5'-GAU CUG AGG UAG AAA GGU GGU CAU GGC UUU C-3' | Human |
| SEQ ID NO: 53 | 5'-U CUG AGG UAG AAA GGU GGU CAU GGC UUU CC-3' | Human |
| SEQ ID NO: 54 | 5'-AU CUG AGG UAG AAA GGU GGU CAU GGC UUU CC-3' | Human |
| SEQ ID NO: 55 | 5'-GAU CUG AGG UAG AAA GGU GGU CAU GGC UUU CC-3' | Human |

In some embodiments, the antisense oligonucleotide comprises a sequence of at least 18, at least 19, at least 20, at least 21, at least 22, at least 23, at least 24, or at least 25 consecutive nucleotides of a nucleic acid sequence set forth in SEQ ID NOs: 24-55.

In another aspect, provided herein are compositions that comprise an antisense oligonucleotide described herein, wherein the oligonucleotide is present in an amount effective to inhibit the binding of Let-7 microRNA to its corresponding binding site in the 3'-UTR in utrophin mRNA. In some embodiments, these compositions further comprise at least one suitable excipient, for example, a pharmaceutically acceptable excipient, or an additive, known in the art.

"Nucleoside" refers to a base (e.g., a purine [e.g. A and G] or pyrimidine [e.g., C, 5-methyl-C, T and U]) combined with a sugar (e.g., [deoxy]ribose, arabinose and derivatives). "Nucleotide" refers to a nucleoside having a phosphate group attached to its sugar moiety. In embodiments these structures may include various modifications, e.g. either in the base, sugar and/or phosphate moieties. "Modified nucleotide/nucleoside" as used herein refers to a nucleotide/nucleoside that differs from the native form. "Oligonucleotide" as used herein refers to a sequence comprising a plurality of nucleotides joined together. An oligonucleotide may comprise modified structures in its backbone structure and/or in one or more of its component nucleotides. In some embodiments, the oligonucleotides are about 8 to 200 bases in length, in further embodiments from about 8 to about 50 bases, from about 8 to about 40 bases, from about 8 to about 32 bases and yet further embodiments, from about 12 to about 32 or from about 12 to about 25 bases in length. In some embodiments, the oligonucleotides are about 12 to about 50 bases in length, from about 12 to about 40 bases, and yet further embodiments, from about 12 to about 25 bases in length. In some embodiments, the oligonucleotides are about 14 to about 50 bases, from about 14 to about 40 bases, from about 14 to about 32, or from about 14 to about 25 bases in length. In some embodiments, the oligonucleotides are about 15 to about 50 bases, from about 15 to about 40 bases, from about 15 to about 32, or from about 15 to about 25 bases in length. In some embodiments, the oligonucleotides are about 16 to about 50 bases, from about 16 to about 40 bases, from about 16 to about 32, or from about 16 to about 25 bases in length. In some embodiments, the oligonucleotides are about 18 to about 50 bases, from about 18 to about 40 bases, from about 18 to about 32, or from about 18 to about 25 bases in length. In some embodiments, the oligonucleotides are about 20 to about 50 bases, from about 20 to about 40 bases, from about 20 to about 32, or from about 20 to about 25 bases in length. In some embodiments, the oligonucleotides are 18 bases in length. In some embodiments, the oligonucleotides are 19 bases in length. In some embodiments, the oligonucleotides are 20 bases in length. In some embodiments, the oligonucleotides are 21 bases in length. In some embodiments, the oligonucleotides are 22 bases in length. In some embodiments, the oligonucleotides are 23 bases in length. In some embodiments, the oligonucleotides are 24 bases in length. In some embodiments, the oligonucleotides are 25 bases in length. In some embodiments, the oligonucleotides are 26 bases in length. In some embodiments, the oligonucleotides are 27 bases in length. In some embodiments, the oligonucleotides are 28 bases in length.

"Alkyl" refers to straight and branched chain saturated hydrocarbon groups (e.g., methyl, ethyl, propyl, butyl, isopropyl, etc.). "Alkenyl" and "alkynyl" refer to hydrocarbon groups having at least one C—C double and one C—C triple bond, respectively. "Alkoxy" refers to an —O-alkyl structure. "Alkylamino" refers to —NH (alkyl) or —N(alkyl) 2 structures. "Aryl" refers to substituted and unsubstituted aromatic cyclic structures (e.g., phenyl, naphthyl, anthracyl, phenanthryl, pyrenyl, and xylyl groups). "Hetero" refers to an atom other than C; including but not limited to N, O, or S. In some embodiments, the above-mentioned groups may be substituted.

"Sugar-modified nucleoside" or "sugar-modified nucleotide" as used herein refers to a nucleoside or nucleotide, respectively, which has a different or modified sugar structure as compared to the sugar moiety of a native deoxyribonucleoside or deoxyribonucleotide, respectively, or ribonucleoside or ribonucleotide, respectively. Such modifications include but are not limited to changes in conformation of the sugar ring, substitution or addition of different ring structures, and the modification (substitution, deletion or addition) of any sugar ring substituents. A sugar-modified nucleoside or nucleotide may be capable of adopting a DNA-like conformation. A "DNA-like conformation" as used herein refers to the sugar structure of the nucleoside or nucleotide and refers to a conformation which resembles the conformation of a native 2'-deoxyribonucleoside or 2'-deoxyribonucleotide, i.e. one whose sugar residue is capable of adopting a C2'-endo (south pucker) and/or 04'-endo (east pucker) conformation. As arabinonucleotides may adopt such a C2'-endo (south pucker) and/or 04'-endo (east pucker) conformation, arabinonucleic acids and DNA exhibit similar conformational preferences (Venkateswarlu et al., *J. Am. Chem. Soc.* 1999, 121:5609; Trempe et al., *J. Am. Chem. Soc.* 2001, 123:4896; Denisov et al., *Nucleic Acids Res.* 2001, 29:4284). Other DNA-like nucleotides include, but are not limited to, alpha-L-LNA (Petersen et al., *J. Am. Chem. Soc.* 2001; 123:7431) and cyclohexene nucleic acids (Wang et al., *J. Am. Chem. Soc.,* 2000, 122:8595).

In some embodiments, the phosphate backbone modification comprises sugar-modified oligonucleotides. In some embodiments, sugar-modified oligonucleotides comprise β-D-arabinonucleotides (i.e., ANA oligomers) and 2'-deoxy-2'-fluoro-β-D-arabinonucleosides (i.e., 2'F-ANA oligomers). In a preferred embodiment, sugar-modified oligonucleotides comprise 2'F-ANA oligomers.

(I)

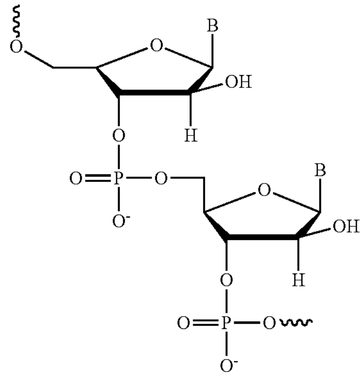

(ANA)

-continued (II)

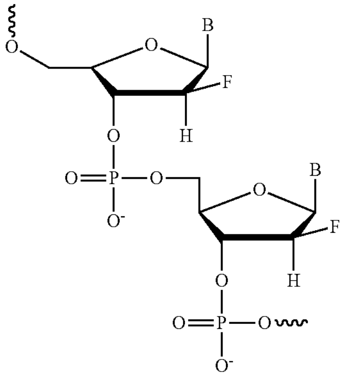

(2'F-ANA)

Without wishing to be bound by theory, it is believed that oligonucleotides that are sugar-modified with ANA and 2'-F ANA display increased resistance to action of degradative nucleases present in serum. When an antisense oligonucleotide forms a duplex with its target miRNA binding sequence in the 3'-UTR utrophin mRNA, for example with a Let-7 microRNA binding sequence, it blocks the binding of Let-7 microRNA with its corresponding binding sequence. This results in stabilization of utrophin mRNA, leading to enhanced utrophin production, and thereby treating Duchenne Muscular Dystrophy (DMD).

In some embodiments, the antisense oligonucleotide is a phosphorothioate molecule. In some embodiments, the antisense oligonucleotide is a 2'-O-methyl phosphorothioate oligoribonucleotide molecule. Phosphorothioate molecules are known in the art. These molecules include a phosphorothioate (PS) bond, which substitutes a sulfur atom for a non-bridging oxygen in the phosphate backbone of an oligo. This modification renders the internucleotide linkage resistant to nuclease degradation.

In some embodiments, the 2'-substituent, e.g., of the arabinose sugar in ANA residues, includes but is not limited to fluorine, hydroxyl, amino, cyano, azido, —CH—$CH_2$, —C≡CH, alkyl (e.g., lower alkyl [e.g., $C_1$-$C_9$ alkyl] e.g., methyl, ethyl, propyl, etc.), alkoxy (e.g., lower alkoxy, [e.g., $C_1$-$C_9$ alkoxy] e.g., methoxy, ethoxy, propoxy, etc.) and functionalized alkyl (e.g., functionalized lower alkyl, e.g. 2'—$CF_3$), alkoxy, and alkoxyalkyl (e.g. methoxyethyl, ethoxyethyl, etc.) groups. In an embodiment, the functionalized alkyl group is selected from the group consisting of methylamino, ethylamino and propylamino groups. In some embodiments, the functionalized alkoxy group is —$O(CH_2)_q$—R, wherein q=2, 3 or 4 and —R is selected from the group consisting of —$NH_2$, —$OCH_3$, and —$OCH_2CH_3$ groups.

In some embodiments, the 2' substituent of the arabinose sugar is fluorine, i.e., the arabinonucleotide is a 2'-fluoroarabinonucleotide (2'F-ANA; also abbreviated "FANA").

In some embodiments, the oligonucleoside comprises an internucleoside linkage comprising a phosphate, thereby being an oligonucleotide. In some embodiments, the sugar-modified nucleosides and/or 2'-deoxynucleosides comprise a phosphate, thereby being sugar-modified nucleotides and/or 2'-deoxynucleotides. In some embodiments, the oligonucleoside comprises an internucleoside linkage comprising a phosphorothioate. In some embodiments, the internucleoside is selected from linkage phosphorothioate, phosphorodithioate, methylphosphorothioate, Rp-phosphorothioate, Sp-phosphorothioate. In some embodiments, the oligonucleotide comprises one or more internucleotide linkages selected from the group consisting of: (a) phosphodiester; (b) phosphotriester; (c) phosphorothioate; (d) phosphorodithioate; (e) Rp-phosphorothioate; (f) Sp-phosphorothioate; (g) boranophosphate; (h) methylene (methylimino) (3'$CH_2$—$N(CH_3)$—$O_5$'); (i) 3'-thioformacetal (3'S—$CH_2$—$O_5$'); (j) amide (3'$CH_2$—C(O)NH-5'); (k) methylphosphonate; (l) phosphoramidate (3'-$OP(O_2)$—N5'); and (m) any combination of (a) to (l).

In one aspect, provided herein are oligonucleotides comprising alternating segments or units of sugar-modified nucleotides (e.g., arabinonucleotide analogues [e.g., FANA]) and 2'-deoxyribonucleotides (DNA). In some embodiments, the oligonucleotide comprises at least 2 of each of sugar-modified nucleotide and 2'-deoxynucleotide segments, thereby having at least 4 alternating segments overall. Each alternating segment or unit may independently contain 1 or a plurality of nucleotides. In some embodiments, each alternating segment or unit may independently contain 1 or 2 nucleotides. In some embodiments, the segments each comprise 1 nucleotide. In some embodiments, the segments each comprise 2 nucleotides. In some embodiments, the plurality of nucleotides may consist of 2, 3, 4, 5 or 6 nucleotides. The oligonucleotide may contain an odd or even number of alternating segments or units. The oligonucleotide may commence and/or terminate with a segment containing sugar-modified nucleotide residues or DNA residues. Accordingly, in some embodiments, the oligonucleotides may be represented as follows:

$$A_1\text{-}D_1\text{-}A_2\text{-}D_2\text{-}A_3\text{-}D_3 \ldots A_z\text{-}D_z$$

Where each of $A_1$, $A_2$, etc. represents a unit of one or more (e.g., 1 or 2) sugar-modified nucleotide residues (e.g., ANA or FANA) and each of $D_1$, $D_2$, etc. represents a unit of one or more (e.g., 1 or 2) DNA residues. The number of residues within each unit may be the same or variable from one unit to another. The oligonucleotide may have an odd or an even number of units. The oligonucleotide may start (i.e. at its 5' end) with either a sugar-modified nucleotide-containing unit (e.g., an ANA-containing unit or a FANA-containing unit) or a DNA-containing unit. The oligonucleotide may terminate (i.e. at its 3' end) with either a sugar-modified nucleotide-containing unit or a DNA-containing unit. The total number of units may be as few as 4 (i.e. at least 2 of each type).

In some embodiments, the oligonucleotides comprise alternating segments or units of arabinonucleotides and 2'-deoxynucleotides, wherein said segments or units each independently comprise at least one arabinonucleotide or 2'-deoxynucleotide, respectively. In some embodiments, the segments each independently comprise 1 to 2 arabinonucleotides or 2'-deoxynucleotides. In some embodiments, the segments each independently comprise 2 to 5 or 3 to 4 arabinonucleotides or 2'-deoxynucleotides. In some embodiments, the oligonucleotides comprise alternating segments or units of arabinonucleotides and 2'-deoxynucleotides, wherein said segments or units each comprise one arabinonucleotide or 2'-deoxynucleotide, respectively. In some embodiments, the segments each independently comprise about 3 arabinonucleotides or 2'-deoxynucleotides. In some embodiments, the oligonucleotides comprise alternating segments or units of arabinonucleotides and 2'-deoxynucleotides, wherein said segments or units each comprise one arabinonucleotide or 2'-deoxynucleotide, respectively. In some embodiments, the oligonucleotides comprise alternating segments or units of arabinonucleotides and 2'-deoxynucleotides, wherein said segments or units each comprise two arabinonucleotides or 2'-deoxynucleotides, respectively.

In some embodiments, the above-mentioned oligonucleotide has a structure selected from the group consisting of:

a) $(A_x\text{-}D_y)_n$ I b) $(D_y\text{-}A_x)_n$ II c) $(A_x\text{-}D_y)_m\text{-}A_x\text{-}D_y\text{-}A_x$ III d) $(D_y\text{-}A_x)_m\text{-}D_y\text{-}A_x\text{-}D_y$ IV wherein each of m, x and y are each independently an integer greater than or equal to 1, n is an integer greater than or equal to 2, A is a sugar-modified nucleotide and D is a 2'-deoxyribonucleotide.

For example, the above-mentioned oligonucleotide has structure I wherein x=1, y=1 and n=10, thereby having a structure:

A-D-A-D-A-D-A-D-A-D-A-D-A-D-A-D-A-D-A-D.

In another example, the above-mentioned oligonucleotide has structure II wherein x=1, y=1 and n=10, thereby having a structure:

D-A-D-A-D-A-D-A-D-A-D-A-D-A-D-A-D-A-D-A.

In another example, the above-mentioned oligonucleotide has structure III wherein x=1, y=1 and n=9, thereby having a structure:

A-D-A-D-A-D-A-D-A-D-A-D-A-D-A-D-A-D-A-D-A.

In another example, the above-mentioned oligonucleotide has structure IV wherein x=1, y=1 and n=9, thereby having a structure:

D-A-D-A-D-A-D-A-D-A-D-A-D-A-D-A-D-A-D-A-D.

In another example, the above-mentioned oligonucleotide has structure I wherein x=2, y=2 and n=5, thereby having a structure:

A-A-D-D-A-A-D-D-A-A-D-D-A-A-D-D-A-A-D-D.

In another example, the above-mentioned oligonucleotide has structure II wherein x=2, y=2 and n=5, thereby having a structure:

D-D-A-A-D-D-A-A-D-D-A-A-D-D-A-A-D-D-A-A.

In another example, the above-mentioned oligonucleotide has structure III wherein x=2, y=2 and m=4, thereby having a structure:

A-A-D-D-A-A-D-D-A-A-D-D-A-A-D-D-A-A-D-D-A-A.

In another example, the above-mentioned oligonucleotide has structure IV wherein x=2, y=2 and m=4, thereby having a structure:

D-D-A-A-D-D-A-A-D-D-A-A-D-D-A-A-D-D-A-A-D-D.

In some embodiments, the oligonucleoside further comprises a third segment comprising a modified nucleoside, wherein said third segment is adjacent to (a) the 5' end of said alternating segments, (b) the 3' end of said alternating segments, or (c) both (a) and (b). In some embodiments, the oligonucleotide further comprises a third segment comprising a modified nucleotide, wherein said third segment is adjacent to (a) the 5' end of said alternating segments, (b) the 3' end of said alternating segments, or (c) both (a) and (b). In some embodiments, the modified nucleotide is a modified ribonucleotide. In some embodiments, the modified ribonucleotide has a modification at its 2' position. For example, the 2' modification is selected from the group consisting of methoxy (2'-O-Me-RNA), methoxyethyl (2'-MOE-RNA), fluoro and propylamino groups.

In some embodiments, the antisense oligonucleotide is a morpholino or phosphorodiamidate morpholino oligonucleotide (PMO) or Vivo-morpholino molecule. Morpholinos and PMOs are known in the art and are synthetic molecules that are the product of a redesign of natural nucleic acid structure. See, e.g., Summerton et al., "Morpholino Antisense Oligomers: Design, Preparation and Properties". *Antisense & Nucleic Acid Drug Development* 7 (3): 187-95. PMOs can bind to complementary sequences by standard nucleic acid base-pairing. The structural difference between morpholinos and DNA is that, while morpholinos have standard nucleic acid bases, those bases are bound to morpholine rings instead of deoxyribose rings. In addition, PMOs are linked through phosphorodiamidate groups instead of phosphates. Replacement of the anionic phosphates with the uncharged phosphorodiamidate groups eliminates ionization in the usual physiological pH range, and thus morpholinos in organisms or cells are uncharged molecules. Vivo-Morpholinos are comprised of a Morpholino oligonucleotide with a unique covalently linked delivery moiety that is comprised of an octa-guanidine dendrimer.

The antisense oligonucleotide may be made by a suitable method known in the art. For example, the antisense oligonucleotide is produced by a chemical process, for example by the chemical phosphoamidite method comprising sulfuration with tetraethylthiuram disulfide in acetonitrile (*Tetrahedron Lett.*, 1991, 32, 3005-3008, see also US2009/0105467; each of which is herein incorporated by reference in its entirety). In some embodiments, the antisense nucleic acid is an oligoribonucleotide molecule, for example, B-D-arabinonucleotide molecule, a 2'-deoxy-2'-fluoro-β-D-arabinonucleoside molecule, or a 2'-O-methyl oligoribonucleotides molecule.

In some embodiments, the synthetic antisense oligonucleotide further comprises a backbone of stabilized internucleotide linkages. A "stabilized internucleotide linkage" means an internucleotide linkage that is relatively resistant to in vivo degradation (e.g., via an exo- or endo-nuclease), compared to a phosphodiester internucleotide linkage. Preferred stabilized internucleotide linkages include, without limitation, phosphorothioate, phosphorodithioate, methylphosphonate, methylphosphorothioate, phosphonoacetate, Rp-phosphorothioate, Sp-phosphorothioate, boranophosphate, or 3'-thioformacetal, or combinations thereof.

In embodiments, DNA residues may contain any of the bases selected amongst adenine (A), cytosine (C), guanine (G) or thymine (T) or versions comprising modifications of the nucleotide base or backbone structures. In embodiments, ANA residues may contain any of the bases selected amongst adenine (A), inosine (I), 2,6-diaminopurine (2,6-DAP), cytosine (C), 5-methylcytosine (5 meC), guanine (G) or thymine (T) or uracil (U).

Oligonucleotides may also include species which include at least one modified nucleotide base. Thus, purines and pyrimidines other than those normally found in nature may be used. As noted above, a nucleotide of the sugar-modified nucleotide segment (e.g. ANA segment) may comprise modifications on its pentofuranosyl portion. Examples of such modifications are 2'-O-alkyl- and 2'-halogen-substituted nucleotides. Some specific examples of modifications at the 2' position of sugar moieties which are useful in the present invention are OH, SH, $SCH_3$, F, OCN, $O(CH_2)_nNH_2$ or $O(CH_2)_nCH_3$where n is from 1 to about 10; $C_1$ to $C_{10}$ lower alkyl, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties.

One or more pentofuranosyl groups of the nucleotide of the sugar-modified nucleotide segment may be replaced by another sugar, by a sugar mimic such as cyclobutyl or by another moiety which takes the place of the sugar.

In some embodiments, provided herein are methods for treating a muscle disease in a subject, the methods comprising the step of administering to said subject a composition for inhibiting a utrophin microRNA molecule. In some embodiments, provided herein are methods for treating or reducing the signs and symptoms associated with muscular dystrophy in a subject, the methods comprising the step of administering to said subject a composition for inhibiting a utrophin microRNA molecule. In some embodiments, translation of utrophin in a muscle cell in the subject is increased over basal levels by about 10%, 20%, 25%, 30%, 40%, 50%, 60%, 70%, 75%, 80%, 90% or more. In some embodiments, translation of utrophin in a muscle cell in the subject is increased over basal levels by about 2-fold, 3-fold, 4-fold, 5-fold, 10-fold, 20-fold, 25-fold, 30-fold, 40-fold, 50-fold, 75-fold, 100-fold or more.

Muscular dystrophy may refer to any type of muscular dystrophy. For example, the muscular dystrophy is Duchenne Muscular Dystrophy (DMD). In another example, the muscular dystrophy is Becker Muscular Dystrophy (BMD).

In some embodiments, such compositions include an oligonucleotide described herein in a therapeutically or prophylactically effective amount sufficient to treat or prevent the muscle disease or muscular dystrophy, and a pharmaceutically acceptable carrier.

A "therapeutically effective amount" refers to an amount effective, at dosages and for periods of time necessary, to achieve the desired therapeutic result, such as a decrease in or a prevention of the expression or translation of a particular target nucleic acid, such as utrophin mRNA. A therapeutically effective amount of an oligonucleotide described herein may vary according to factors such as the disease state, age, sex, and weight of the individual, and the ability of the oligonucleotide to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as preventing or treating a disease. A prophylactically effective amount can be determined as described above for the therapeutically effective amount. For a particular subject, specific dosage regimens may be adjusted over time according to the individual need and the professional judgement of the person administering or supervising the administration of the compositions.

As used herein "pharmaceutically acceptable carrier" or "excipient" includes solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions described herein is contemplated. Supplementary active compounds can also be incorporated into the compositions.

Therapeutic compositions typically are sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, an oligonucleotide described herein can be administered in a time release formulation, for example in a composition which includes a slow release polymer. The oligonucleotide can be prepared with carriers that will protect it against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating an active compound, such as an oligonucleotide described herein, in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In some embodiments, an oligonucleotide described herein may be formulated with one or more additional compounds that enhance its solubility.

The terms "treatment" or "treating," as used herein, refers to any treatment of a disease in a mammal and includes: (1) preventing the disease from occurring in a mammal which may be predisposed to the disease but does not yet experience or display symptoms of the disease; e.g. prevention of the outbreak of the clinical symptoms; (2) inhibiting the disease, e.g., arresting its development; or (3) relieving the disease, e.g., causing regression of the symptoms of the disease.

The term "subject," as used herein, includes any human or non-human animal. The term "non-human animal" includes all vertebrates, e.g., mammals and non-mammals, such as non-human primates, sheep, dog, cow, chickens, amphibians, reptiles, etc. The method of treatment described herein can be used to treat a suitable mammal, preferably a human.

In another aspect, provided herein are methods of treating or reducing the signs and symptoms associated with Duchenne muscular dystrophy (DMD) in a subject, by administering to the subject a composition for inhibiting a utrophin microRNA molecule. In some embodiments, provided herein are methods of treating or reducing the signs and symptoms associated with Becker muscular dystrophy (BMD) in a subject, by administering to the subject a composition for inhibiting a utrophin microRNA molecule.

In another aspect, provided herein are compositions comprising an effective amount of an agent that inhibits utrophin microRNA molecule. In an exemplary embodiment, the agent comprises a let-7c miRNA antisense oligonucleotide (e.g., a sequence set forth in SEQ ID NO: 2), a miR-133b miRNA antisense oligonucleotide (e.g., a sequence set forth in SEQ ID NO: 4), a miR-150 miRNA antisense oligonucleotide (e.g., a sequence set forth in SEQ ID NO: 6), a miR-196b miRNA antisense oligonucleotide (e.g., a sequence set forth in SEQ ID NO: 8), a miR-206 miRNA antisense oligonucleotide (e.g., a sequence set forth in SEQ ID NO: 10), or a miR-296-5p miRNA antisense oligonucleotide (e.g., a sequence set forth in SEQ ID NO: 12).

In some embodiments, the methods comprise administering compositions where the active compound is the sole active ingredient in the composition. However, also contemplated are methods for treating diseases and disorders that comprise administering compositions comprising multiple active compounds.

In some embodiments, provided herein are compositions comprising an effective amount of an agent that blocks interaction or binding between a utrophin microRNA molecule and its binding sequence within utrophin mRNA. In an exemplary embodiment, the agent comprises a let-7c miRNA binding sequence antisense oligonucleotide (e.g., a sequence set forth in SEQ ID NOs: 24-55 or SEQ ID NOs: 64-75).

In one embodiment, an active ingredient of compositions described herein is a single let-7c miRNA binding sequence antisense oligonucleotide (e.g., an oligonucleotide with a sequence selected from SEQ ID NOs: 24-55 or SEQ ID NOs: 64-75). In some embodiments, the active ingredients of compositions described herein comprise more than one let-7c miRNA binding sequence antisense oligonucleotide (e.g., a set of oligonucleotides with sequences selected from SEQ ID NOs: 24-55 or SEQ ID NOs: 64-75). In some embodiments, the active ingredients of compositions described herein comprise two, three, four, or five let-7c miRNA binding sequence antisense oligonucleotides (e.g., two, three, four, or five oligonucleotides with sequences selected from SEQ ID NOs: 24-55 or SEQ ID NOs: 64-75). In some embodiments, the active ingredients of compositions described herein comprise more than five let-7c miRNA binding sequence antisense oligonucleotides (e.g., a set of oligonucleotides with sequences selected from SEQ ID NOs: 24-55 and SEQ ID NOs: 64-75).

In one embodiment, the active ingredients of compositions described herein comprise one or more let-7c miRNA binding sequence antisense oligonucleotides (e.g., oligonucleotides with sequences selected from SEQ ID NOs: 24-55 or SEQ ID NOs: 64-75) and at least one additional miRNA antisense oligonucleotide, e.g., a miR-133b antisense oligonucleotide (e.g., a sequence set forth in SEQ ID NO: 4), a miR-150 antisense oligonucleotide (e.g., a sequence set forth in SEQ ID NO: 6), a miR-196b antisense oligonucleotide (e.g., a sequence set forth in SEQ ID NO: 8), a miR-206 antisense oligonucleotide (e.g., a sequence set forth in SEQ ID NO: 10), or a miR-296-5p antisense oligonucleotide (e.g., a sequence set forth in SEQ ID NO: 12).

In some embodiments, the active ingredients of compositions described herein comprise one or more let-7c miRNA binding sequence antisense oligonucleotides (e.g., oligonucleotides with sequences selected from SEQ ID NOs: 24-55 or SEQ ID NOs: 64-75) and one additional miRNA antisense molecule. In some embodiments, the active ingredients of compositions described herein comprise one or more let-7c miRNA binding sequence antisense molecules (e.g., oligonucleotides with sequences selected from SEQ ID NOs: 24-55 or SEQ ID NOs: 64-75) and two, three, four, or five additional miRNA antisense molecules. In some embodiments, the active ingredients of compositions described herein comprise one or more let-7c miRNA binding sequence antisense molecules (e.g., oligonucleotides with sequences selected from SEQ ID NOs: 24-55 or SEQ ID NOs: 64-75) and more than five additional miRNA antisense molecules.

In one embodiment, at least one miRNA binding sequence antisense oligonucleotide in the compositions described herein comprises one or more arabinonucleotides. In some embodiments, at least one miRNA binding sequence antisense oligonucleotides in the compositions described herein comprises 2'F-ANA. In a preferred embodiment, the let-7c miRNA binding sequence antisense oligonucleotide in the compositions described herein comprise ANA or 2'F-ANA. In some embodiments, all the miRNA binding sequence antisense oligonucleotides in the compositions described herein comprise ANA or 2'F-ANA.

In one embodiment, one or more let-7c miRNA binding sequence antisense oligonucleotides in the compositions described herein comprise ANA or 2'F-ANA, while at least one of the remaining let-7c miRNA binding sequence antisense oligonucleotides are 2'-O-methyl phosphorothioate oligoribonucleotides, morpholino oligoribonucleotides, phosphorodiamidate morpholino oligoribonucleotides or a combination thereof. In some embodiments, one or more let-7c miRNA binding sequence antisense oligonucleotides in the compositions described herein comprise ANA or 2'F-ANA, while at least one of the additional miRNA antisense oligonucleotides (e.g., a miR-133b miRNA antisense oligonucleotide (e.g., a sequence set forth in SEQ ID NO: 4), a miR-150 miRNA antisense oligonucleotide (e.g., a sequence set forth in SEQ ID NO: 6), a miR-196b miRNA antisense oligonucleotide (e.g., a sequence set forth in SEQ ID NO: 8), a miR-206 miRNA antisense oligonucleotide (e.g., a sequence set forth in SEQ ID NO: 10), or a miR-296-5p miRNA antisense oligonucleotide (e.g., a sequence set forth in SEQ ID NO: 12)) comprise ANA, 2'F-ANA, 2'-O-methyl phosphorothioate, morpholino, phosphorodiamidate morpholino, or a combination thereof.

Also encompassed are methods for treating diseases and disorders that comprise administering an active compound described herein in combination with one or more other therapeutic agents appropriate for the disease or disorder that is being treated, as is known in the art. These agents include, but are not limited to, drugs for treating DMD or BMD.

In some embodiments, a composition for inhibiting a utrophin microRNA molecule also induces utrophin protein production. A utrophin microRNA molecule is a microRNA molecule which binds the 5' or 3'-UTR of utrophin mRNA and inhibits utrophin protein production.

In some embodiments, administering a composition for inhibiting a utrophin microRNA molecule comprises contacting the microRNA molecule with a utrophin microRNA antisense oligonucleotide. In some embodiments, a composition for inhibiting a utrophin microRNA molecule comprises a utrophin microRNA antisense oligonucleotide. In some embodiments, a composition for inhibiting a muscle cell specific microRNA molecule comprises a muscle cell specific utrophin microRNA antisense oligonucleotide.

In some embodiments, administering a composition for inhibiting a utrophin microRNA molecule comprises contacting utrophin mRNA with an oligonucleotide complementary to the microRNA binding sequence within utrophin mRNA. In some embodiments, a composition for inhibiting a utrophin microRNA molecule comprises an oligonucleotide complementary to the microRNA binding sequence within utrophin mRNA. In some embodiments, a composition for inhibiting a muscle cell specific microRNA molecule comprises an oligonucleotide complementary to a muscle cell specific microRNA binding sequence within utrophin mRNA.

In some embodiments, a composition for inhibiting a utrophin microRNA molecule is administered to a muscle cell in a subject. In some embodiments, a composition for inhibiting utrophin microRNA molecule is administered to a subject and is targeted to a muscle cell.

In some embodiments, methods described herein reduce signs and symptoms associated with Duchenne muscular dystrophy (DMD) or Becker muscular dystrophy (BMD). In some embodiments, methods described herein improve walking of a DMD or BMD patient. In some embodiments, methods described herein reduce or inhibit calves swelling with fibrous tissue. In some embodiments, methods described herein induce muscle growth. In some embodiments, methods described herein induce muscle regeneration. In some embodiments, methods described herein reduce or inhibit contractures. In some embodiments, methods described herein reduce or inhibit scoliosis. In some embodiments, methods described herein reduce or inhibit diaphragm weakening. In some embodiments, methods described herein reduce or inhibit a cardiac disease caused by or associated with lack of dystrophin.

The oligonucleotides described herein and pharmaceutical compositions comprising them can be administered to a subject by any suitable method known in the art. In some embodiments, administration is systemic. In some embodiments, administration is intramuscular. In some embodiments, administration of the nucleic acids described herein is gymnotic.

In some embodiments of methods and compositions described herein, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In some embodiments, the active ingredient is formulated in a capsule. In accordance with this embodiment, the compositions comprise, in addition to the active compound (e.g. the mimetic compound, peptide or nucleotide molecule) and the inert carrier or diluent, a hard gelatin capsule.

In some embodiments, the pharmaceutical compositions are administered by intravenous, intra-arterial, or intramuscular injection of a liquid preparation. Suitable liquid formulations include solutions, suspensions, dispersions, emulsions, oils and the like. In some embodiments, the pharmaceutical compositions are administered intravenously and are thus formulated in a form suitable for intravenous administration. In some embodiments, the pharmaceutical compositions are administered intra-arterially and are thus formulated in a form suitable for intra-arterial administration. In some embodiments, the pharmaceutical compositions are administered intra-muscularly and are thus formulated in a form suitable for intra-muscular administration.

In some embodiments, the pharmaceutical compositions are administered topically to body surfaces and are thus formulated in a form suitable for topical administration. Topical formulations include gels, ointments, creams, lotions, drops and the like.

In some embodiments, the pharmaceutical composition is administered as a suppository, for example a rectal suppository or a urethral suppository. In some embodiments, the pharmaceutical composition is administered by subcutaneous implantation of a pellet. In some embodiments, the pellet provides for controlled release of active agent over a period of time.

In some embodiments, the active compound is delivered in a vesicle, e.g., a liposome.

In other embodiments, carriers or diluents used in the compositions described herein include, but are not limited to, a gum, a starch (e.g., corn starch, pregeletanized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

In some embodiments, parenteral vehicles (for subcutaneous, intravenous, intra-arterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

In other embodiments, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic $F_{68}$, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

In some embodiments, the pharmaceutical compositions provided herein are controlled-release compositions, i.e. compositions in which the active compound is released over a period of time after administration. Controlled- or sustained-release compositions include formulation in lipophilic depots (e.g. fatty acids, waxes, oils). In some embodiments, the composition is an immediate-release composition, i.e. a composition in which of the active compound is released immediately after administration.

In some embodiments, the pharmaceutical composition is delivered in a controlled release system. For example, the agent may be administered using intravenous infusion, an implantable osmotic pump, a transdermal patch, liposomes, or other modes of administration. In one embodiment, a pump may be used. In some embodiments, polymeric materials are used; e.g. in microspheres in or an implant. In yet some embodiments, a controlled release system is placed in proximity to the target cell, thus requiring only a fraction of the systemic dose.

The compositions also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also included are particulate compositions coated with polymers (e.g. poloxamers or poloxamines) and the compound coupled to antibodies directed against tissue-specific receptors, ligands or antigens or coupled to ligands of tissue-specific receptors.

Also contemplated are compounds modified by covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. Modified compounds are known to exhibit substantially longer half-lives in blood following intravenous injection than do the corresponding unmodified compounds. Such modifications may also increase the compound's solubility in aqueous solution, eliminate aggregation, enhance the physical and chemical stability of the compound, and reduce the immunogenicity and reactivity of the compound. As a result, a desired in vivo biological activity may be achieved by administration of such polymer-compound abducts less frequently or in lower doses than with the unmodified compound.

In another aspect, provided herein are commercial packages comprising an oligonucleotide described herein. In some embodiments, the commercial package further comprises instructions for use of the oligonucleotide.

In another aspect, provided herein are uses of an oligonucleotide described herein for treating or reducing the signs and symptoms associated with a muscle disease, myopathy or muscular dystrophy (e.g., DMD or BMD) in a subject, or for enhancing or upregulating utrophin. In another aspect, provided herein are uses of an oligonucleotide described herein for the preparation of a medicament for treating or reducing the signs and symptoms associated with a muscle disease, myopathy or muscular dystrophy (e.g., DMD or BMD) in a subject, or for enhancing or upregulating utrophin in a subject.

The following examples are presented in order to more fully illustrate the preferred embodiments of the invention. They should in no way be construed, however, as limiting the broad scope of the invention.

Example 1

Utrophin Genomic Editing for Duchenne's Muscular Dystrophy Therapy

The aim of this Example is to develop Utrophin Genome editing as a novel therapeutic strategy for Duchenne Muscular Dystrophy (DMD).

Specific Aim 1: Design and optimize CRISPR-Cas9 based genome editing constructs for deleting miRNA binding sites in the 3'-UTR of the mouse and human utrophin gene. Test the ability to edit and upregulate utrophin in mouse and human cell lines as well as in human induced pluripotent and muscle stem cells (hiPSCs & hMuSCs) in vitro.

Specific Aim 2: Develop AAV-based vectors for CRISPR-Cas9 based genome editing in mouse and human utrophin cell lines. Test the ability of AAVs to edit the endogenous gene and upregulate utrophin in mouse and human cell lines as well as in hiPSCs and hMuSCs in vitro.

Specific Aim 3: Test the ability of the AAV CRISPR-Cas9 based Utrophin genome editing strategy to upregulate utrophin and rescue dystrophic pathophysiology in the mdx mouse model of DMD, in vivo.

Background & Disease Relevance:

Dystrophin and utrophin share functional properties and have similar affinities for binding F-actin at the amino terminal, as well as bind the D/SGC at the carboxyl terminal (FIG. 1 outlines similarities).

Utrophin is upregulated during the perinatal period and during regeneration. During these periods where there is lack of necrosis in dystrophin deficient muscle suggesting indirectly, a protective role played by elevated levels of utrophin. Utrophin cDNA delivered transgenically or by viral-vector based gene therapy have been shown to rescue the dystrophic phenotype providing more direct evidence for this role. Current strategies have focused on utrophin promoter trans-activation due to the potential ease of delivery using pharmacological methods, however, efficacy has been limited. While promising, none are currently clinically applicable, in part because it is increasingly evident that regulation of utrophin expression is more complex than previously appreciated and that promoter trans-activating molecules may not suffice as therapeutics by themselves. It has been shown that equally important miRNA based mechanisms repress utrophin expression in myofibres and a set of six miRNAs (miR-296-5p, miR-206, miR-150, miR-133b, let-7c and miR-196b) have been identified that regulate the vast majority (c. 99%) of utrophin message in cultured muscle cells. Further, it has recently been shown that preventing let-7c miRNA-binding to its binding site in the utrophin 3'-UTR using 20MePS site blocking oligonucleotide strategies can upregulate utrophin in vitro, as well as functionally rescue the dystrophic phenotype in the mdx mouse model of DMD in vivo. The alleviation of miRNA-based repression by genome editing to delete the miRNA-binding sites in the Utrophin 3'-UTR will be studied.

Genome Editing for DMD: The advent of Clustered Regularly Interspaced Short Palindromic Repeats (CRISPR) and CRISPR-associated protein 9 (Cas9) genome editing strategies are proving extremely valuable in terms of developing therapeutic strategies to treat genetic diseases. Indeed, the demonstration of a dual AAV-mediated gene correction using CRISPR-Cas9 for treating ornithine transcarbamylase (OTC) deficiency in neonatal mice offers a roadmap for developing therapeutic interventions for DMD patients. CRISPR/Cas9 systems are genome editing systems that in nature, provide bacteria with defense against foreign DNA (e.g. viruses). For genome editing purposes, short guide RNAs (sgRNAs) and RNA-guided DNA nucleases (e.g. SpCas9, SaCas9) are used to precisely create double-stranded DNA breaks (DSBs) at specific chromosomal positions of target cells/organisms adjacent to a protospacer adjacent motif (PAM) causing an error-prone non-homologous end-joining (NHEJ) and/or homologous recombination (HR) at the DSBs of the targeted genome. Recently, a number of investigators have described of CRISPR/Cas9 based genome editing strategies that used CRISPR/Cas9-mediated NHEJ to bypass the Exon 23 point mutation in the mdx mouse model of DMD. It has also been suggested that this strategy could be used to convert a subset of patients with DMD into the less severe allelic Becker Muscular Dystrophy (BMD) variant by expressing an internally deleted form of dystrophin; indeed, internally truncated dystrophin expression has been demonstrated by editing iPSCs generated from DMD patients.

As outlined herein, the inventor has designed a CRISPR-Cas9 based genome editing approach to delete the miRNA-binding sites in the 3'-UTR of the utrophin gene. By alleviating the miRNA-mediated repression, utrophin expression is upregulated. When combined with AAV-based delivery and/or SC-based delivery, this approach is a novel and exciting strategy to achieve therapeutic utrophin upregulation in skeletal muscle in vivo, that in principle would benefit all DMD patients. The overall strategy is outlined in FIGS. 2A-2B.

Preliminary Studies/Data: First, the inventor has identified a novel set of miRNAs that bind the 3'-UTR of utrophin and modulate its expression (FIGS. 3A-3B) and, has demonstrated Proof-of-Concept for the strategy that blocking the let-7c miRNA-utrophin 3'-UTR interaction using systemic delivery of 20MePS SBOs, upregulates utrophin and rescues the dystrophic phenotype of the mdx mice.

Figure 3B:
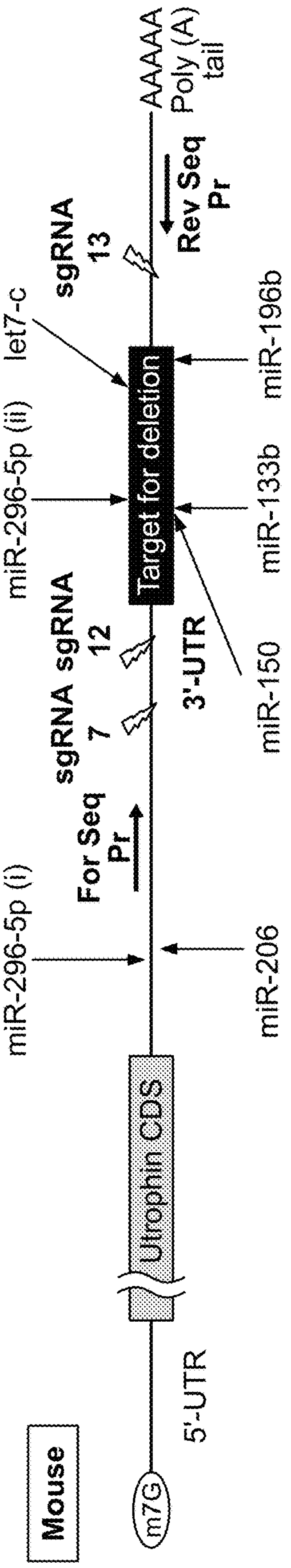
Figures 4A, 4B:
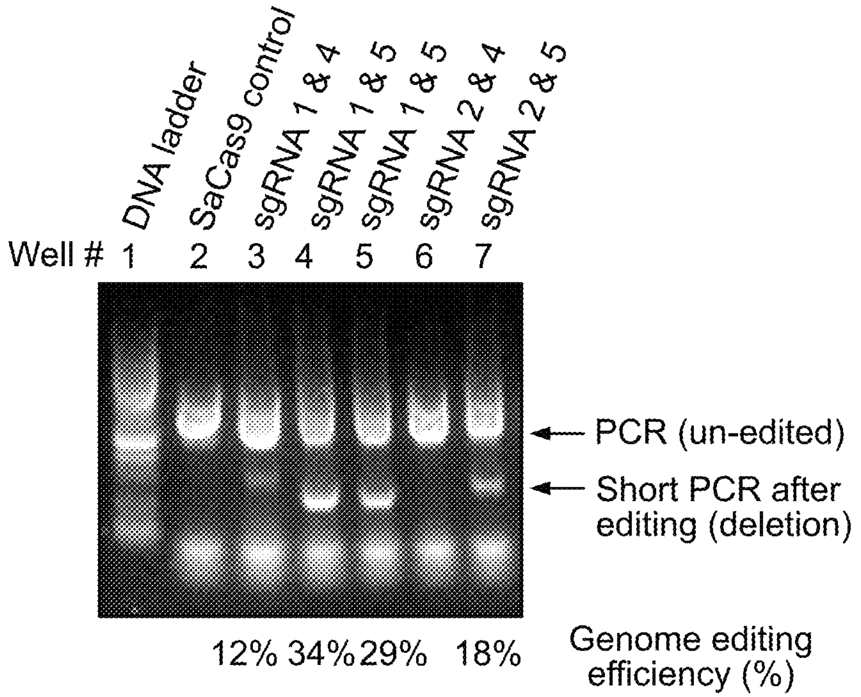
FIGS. 4A-4B illustrate targeted genome editing (deletion) of human utrophin gene: validation by PCR.
Figure 5A:
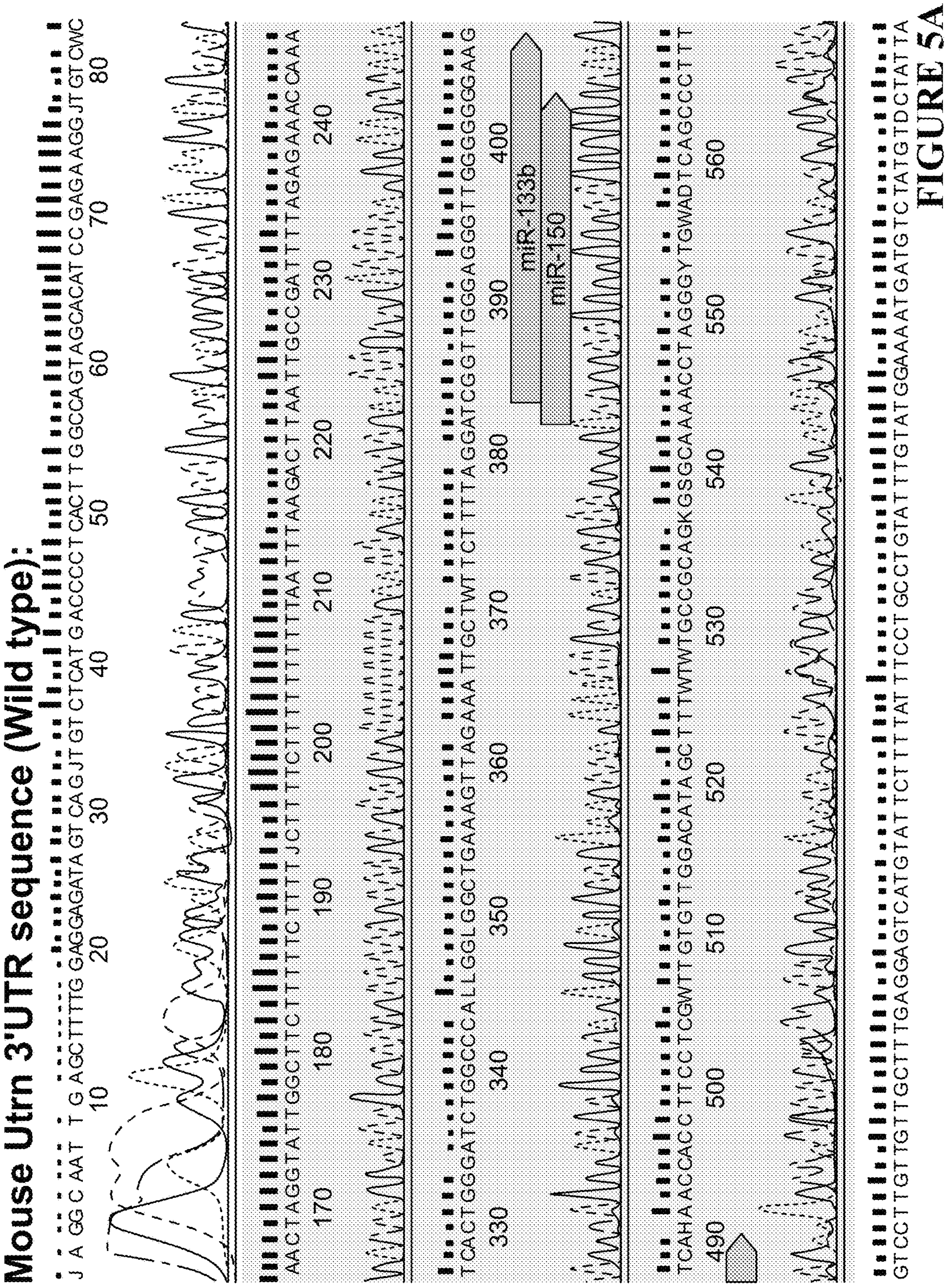
FIGS. 5A-5B illustrate targeted genome editing (deletion) of Mouse utrophin gene: validation by sequence.
Figure 5A:
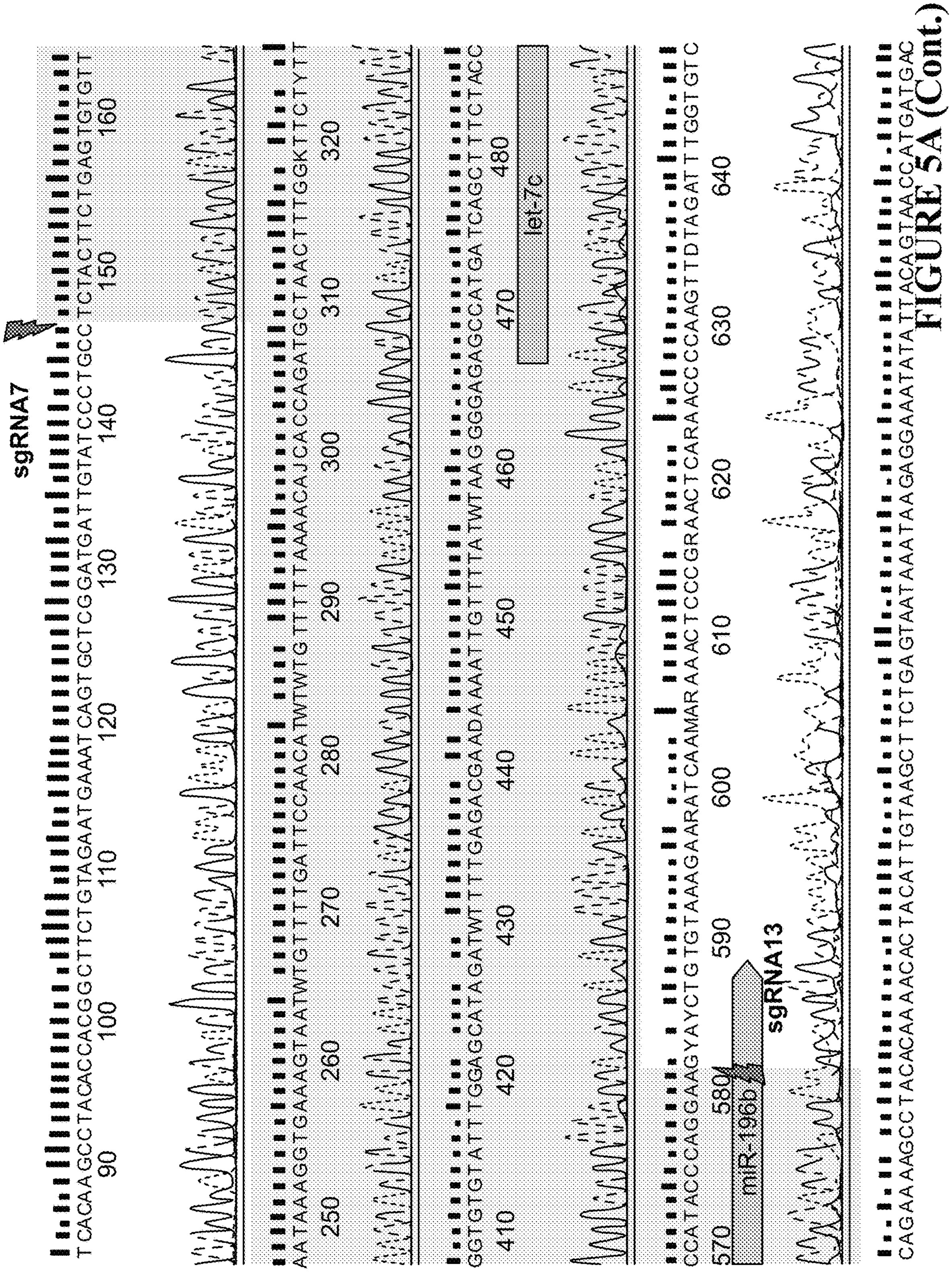
Figure 5B:
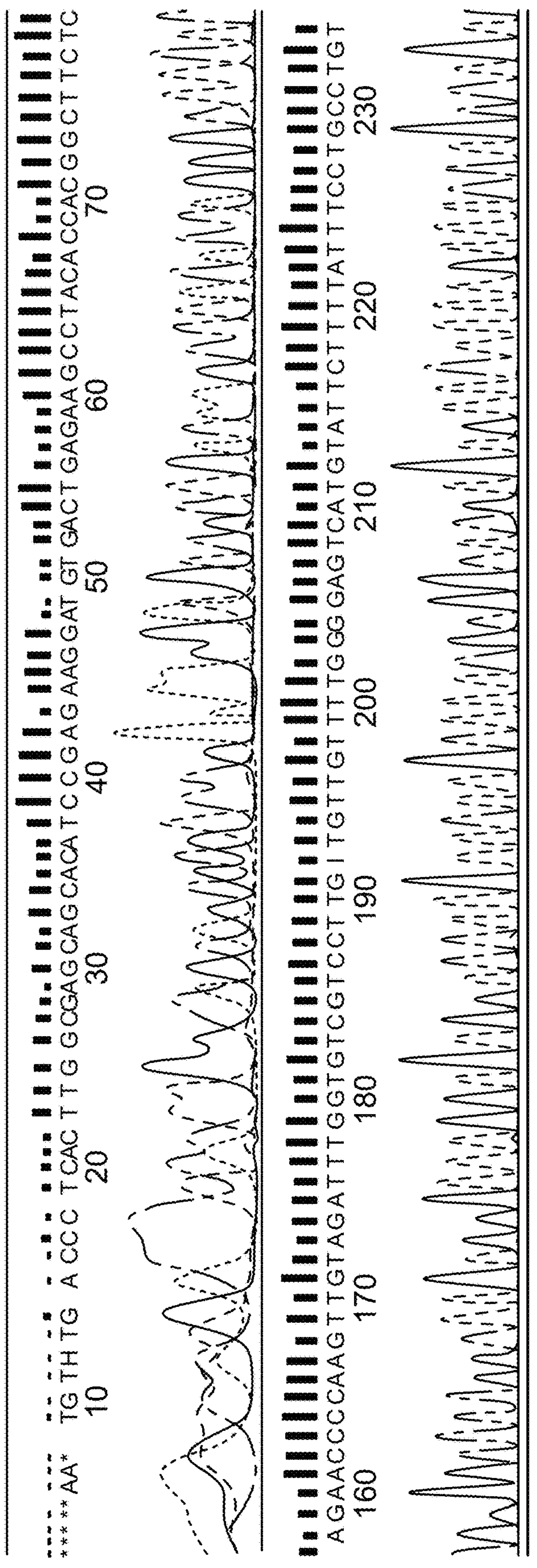
Figure 5B:
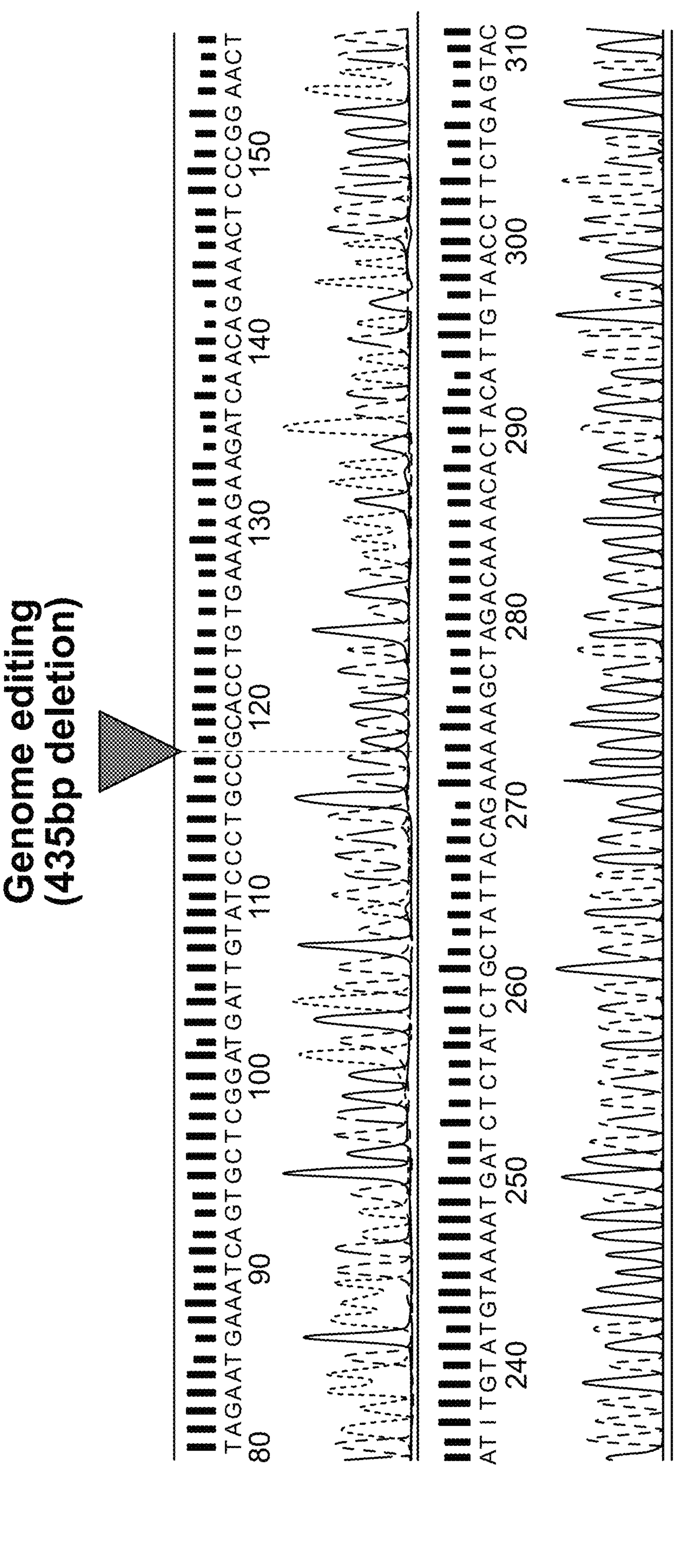
Figure 6:
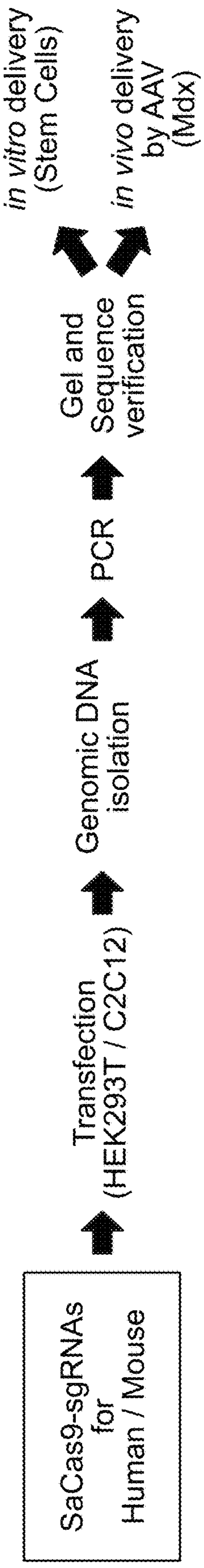
FIG. 6 is a schematic showing overview of Research Design/methods. The overall genome editing strategy is described in FIG. 2B. Location of sgRNA's and regions targeted are shown in FIG. 3.
Figure 7:
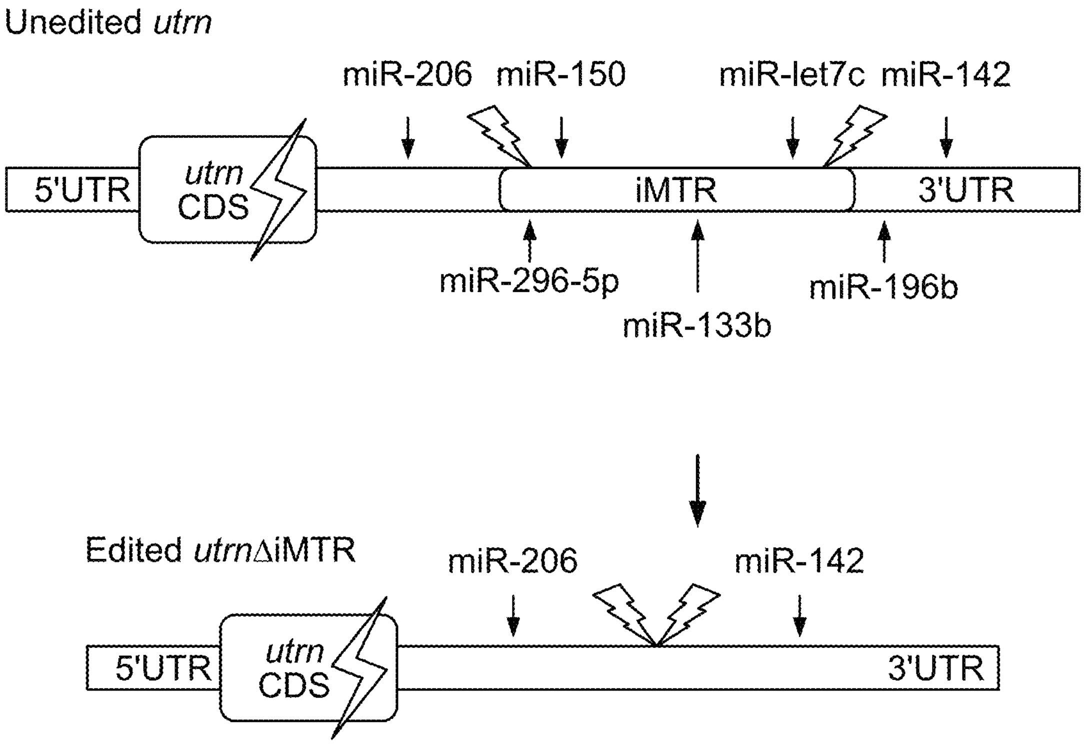
FIG. 7 shows schematics of the unedited and edited Utrophin gene. The miRNA-binding sites and sgRNA positions (shown as bolts) for editing the Utrophin gene and deleting the inhibitory miRNA target region ("iMTR") are depicted.

Second, the inventor has designed sgRNAs to target Cas9 editing and developed pX601 AAV vector-based constructs for editing the miRNA binding sites of the human and mouse Utrophin genes (FIGS. 3A-3B and Table 2). The constructs have been transfected into HEK293T (human) and C2C12 (mouse) cell lines to achieve gene editing (FIGS. 4A-4B) and deletion of the inhibitory miRNA target region ("iMTR") (FIG. 7) and editing and deletion have been verified by sequencing (FIGS. 5A-5B). The iMTR spans positions 211-1713 in the mouse 3'-UTR; the iMTR spans positions 215-1747 in the human 3'-UTR.

TABLE 2

| miRNA | Seed Sequence | Sites in Utrophin | Position in human 3'UTR | Position in mouse 3'UTR |
|---|---|---|---|---|
| miR133b | GGACCAA | 1 in 3'UTR | 1514 | 1479 |
| miR-let7c-5p | CTACCTC | 1 in 3'UTR | 1600-1607 | 1563-1570 |
| miR-150-5p | TTGGGAG | 1 in 3'UTR | 1636 | 1591 |
| miR-296-5p | GGGGCCC | 2 in 3' UTR<br>2 in CDS | 318, 1514 | 317, 1478 |
| miR-196b-5p | ACTACCT | 1 in 3'UTR | 1618-1642 | 1646-1668 |
| miR-206 | ACATTCC | 1 in 3'UTR | 400-406 | 397-403 |
| miR-142-3p | ACACTAC | 1 in 3'UTR | 1863-1870 | 1830-1837 |
| has-miR-135-5p | AAGCCAT | | 1583-1589 | |

Research Design/Methods

Briefly, guides targeting the human and mouse utrophin gene are designed using the Benchling online Tool. sgRNAs are ranked based on highest predicted activity and least potential off-target sites. Primers are annealed and cloned into the BsaI site of the pX601-AAV-CMV::NLS-SaCas9-NLS-3xHA-bGHpA;U6:: BsaI-sgRNA vector (i.e. the pX601 from Prof. Feng Zhang's lab. at MIT; obtained from Addgene). Plasmid with combinations of targeting guides (for example sgRNA1/2 with sgRNA 4/5 for human and sgRNA 7/12 with sgRNA13 for mouse) are transfected into HEK293T and C2C12 cells. Constructs will also be electroporated into hMuSCs and iPSCs using protocols routinely being used in the Musumuru and Mourkioti labs, since transfection is less efficient for SCs. DNA is extracted 3 days later for determination of efficiency and verification of editing by PCR gel electrophoresis and DNA sequencing. Endogenous utrophin protein levels is determined by western blotting. The pX601 plasmids which contain sgRNAs, SaCas9, regulatory elements and ITR for porting to AAV for gene delivery in vivo and are incorporated into infectious particles, using standard triple transfection protocols. The AAV2/9 serotype is used due to its excellent ability to transduce both skeletal and cardiac muscle.

Two AAVs (containing one sgRNA each) are used to achieve targeting in vivo. Differing doses of the AAVs are tested on cultured muscle cells for their ability to alleviate Utrophin repression using a) analysis of cells transfected with Utrophin reporter constructs combined with qPCR and also b) qPCR combined with western blotting analysis of endogenous utrophin expression.

For these studies a double-blind, randomized approach is used and 28 mice are used (14 control cohort and 14 treated cohort)/method based on power calculations. After the trial (s) mice are analyzed by undertaking a rigorous morphological, biochemical, molecular and physiological evaluation. Identity and treatment codes are broken after all analyses are completed. The sgRNA AAVs are a) injected into TA muscle in 1 month old mdx mice and mice analyzed after 2 months. The dose is c. $1\times10^{11}$ genome copies per muscle, which has been used successfully and b) injected systemically using c. $2.5\times10^{11}$ genome copies per animal i.p. in 3 day old mdx pups and analyzed after 3 months. This method results in extremely efficient body-wide delivery of AAV to muscles.

Evaluation of dytrophic muscle function: Evaluation of muscle in mdx mice for a) improvement of the dystrophic phenotype and b) lack of off-target editing and overt toxicity. To maximize the information content of the studies the evaluation includes anatomical, biochemical/molecular and physiological methods.

Morphological Methods: The methods used here are routine (e.g. H&E staining). The focus will on quantifying parameters such as the amount of necrosis in muscle, cross sectional area and fiber diameter (which are measures of hypertrophy). number of centrally nucleated fibers (which indicate past bouts of muscle regeneration) and tissue inflammation.

Biochemical/Molecular Methods: Here the increase in utrophin mRNA and protein will be quantified, as well as analysis of serum creatine kinase (CK) levels that are taken before, during and after the intervention. Declining levels of CK in the serum would be indicative of amelioration of the dystrophic phenotype. Additionally, hydroxyproline assays will be performed for collagen content (as a marker for fibrosis) on these muscles.

Physiological Methods: Physiological evaluation will be based on quantifying the impairment of mdx mouse muscle function due to a variety of mechanical defects in dystrophic muscle. Here the amount of force will be quantified that can be generated by muscle during twitch and tetanus (absolute force) as well as calculate the specific force (absolute force/cross sectional area). Also measured will be the ability of muscle to produce force after it has been subjected to Eccentric contractions (ECC) protocols where there is a forced lengthening of muscle during tetanic contraction. Comparisons of these parameters in treated and untreated mdx mice along with control (wild-type) mice will yield an objective index of physiological improvement of the dystrophic phenotype. Taken together, the anatomical, biochemical and physiological measurements described above should offer a comprehensive, objective test of the hypothesis that an increase of utrophin expression can ameliorate the dystrophic phenotype by functionally substituting for the missing dystrophin in skeletal muscle.

Monitoring of Off-target Editing and Toxicity: Given the novelty of the approach, monitoring of potential toxicities and off-target editing are planned. Primers targeting each sgRNA's top 10 off-target loci will be used to PCR amplify and sequence to determine off-target indels. While the resources in this RFA are insufficient to undertake a rigorous toxicity screen in itself, samples will be collected and monitored for the obvious potential toxicities (e.g. immune reactions to bacterial saCas9, to AAV capsids and carcinogenesis) that could all preclude translation of this type of approach. Overall health and parameters such as body weight, food/fluid intake, terminal organ weight) will be recorded and monitored in consultation with ULAR Vets. Also collected will be blood and serum samples, urine, skin, solid organs and pieces of GI tract for analysis of overt toxicity by histology. IFN-γ ELISPOT assay will be performed on whole blood to monitor T-cell activation. Serum chemistry (enzymes and markers) will be undertaken for renal, liver, muscle and cardiac function.

Additional targeting constructs will be generated, tested and rank ordered based on their ability to edit mouse and human cell lines as well as in SC's. The constructs will be ported into viral vectors and have AAV particles generated by Penn Vector core. The crossing of mdx mice (into SCID mice) to enable testing the ability of transplanted SC's in vivo in future experiments will be initiated. Further, the ability of the dual AAV system to edit mouse and human cell lines will be tested. as well as in SC's and b) preclinical studies in mdx mice using AAV-genome editing of the utrophin gene to test the translationally relevant hypothesis will be undertaken.

Example 2 pX601-Based Construct Containing SaCas9 and Guide RNAs Transfected into HEK293T Cells Deleted miRNA-Binding Sites from Utrophin 3'UTRs As discussed above, Utrophin is the autosomal homolog of dystrophin, the protein product of the Duchenne's muscular dystrophy (DMD) locus. When overexpressed, utrophin ameliorates the dystrophic phenotype, hence is considered a promising therapeutic strategy for DMD. A number of miRNAs post-transcriptionally repress utrophin levels by binding cognate sites in the 3'-UTR.

Recently, it was demonstrated that individual utrophin: miRNA repression can be alleviated using let-7c site blocking oligonucleotides (SBOs) to achieve utrophin upregulation and functional improvement of mdx mice. The advent of genome editing allows the possibility of targeting the miRNA: utrophin repression in vivo and offers an exciting therapeutic approach in DMD.

The inventor hypothesized that CRISPR-Cas9 based editing can be utilized to target and delete miRNA-binding sites in the utrophin 3'UTR to achieve utrophin upregulation in DMD patients, and utilized the following methods to target and edit out (delete) miRNA binding sites in the 3'UTR of the Utrophin gene in HEK human cell lines.

A pX601-based construct containing SaCas9 and guide RNAs was transfected into HEK293T cells to delete miRNA-sites from utrophin 3'UTRs. Edited clones were screened by PCR sizing (approximately 500 bp) and confirmed by sequencing. Western blots were performed to validate utrophin upregulation as a result of successful editing. An enhanced green fluorescent protein (EGFP) tagged editing construct was developed and electroporated into human induced pluripotent stem cells (hiPSCs). Cells were subjected to FACS followed by clonal selection. Clones were subjected to PCR sizing and sequencing of the 3'UTR region to verify genome editing of the miRNA-binding sites in the utrophin gene.

CRISPR-Cas9 based genome editing of the miRNA-binding sites in the 3'UTR of the utrophin in DMD hiPSCs provided herein offers a novel strategy to "repress the repression" and achieve utrophin upregulation in DMD patients in vivo. In principle this strategy would be applicable for all DMD patients, irrespective of individual mutation.

Example 3

Figure 9A:
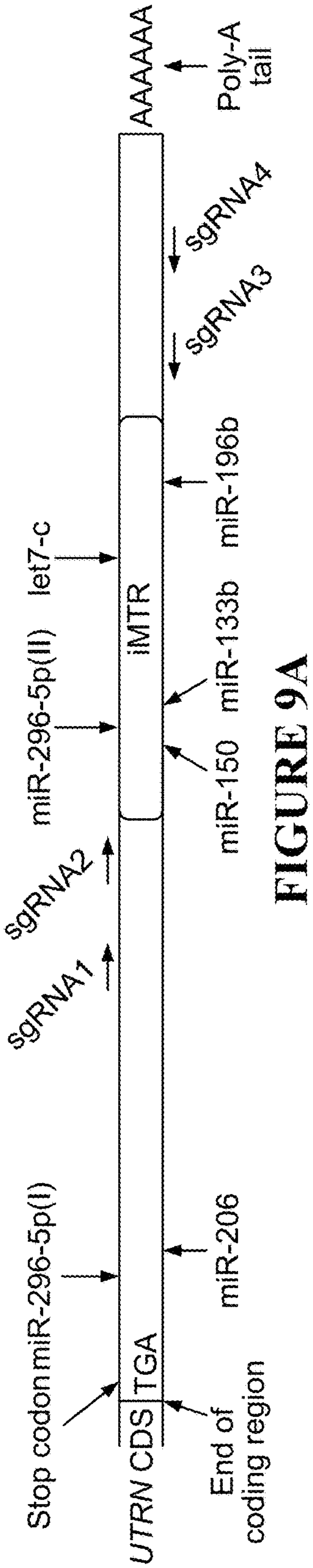
FIGS. 9A-9D present CRISPR/Cas9 genome editing targeting UTRN 3'UTR.
Figure 9B:
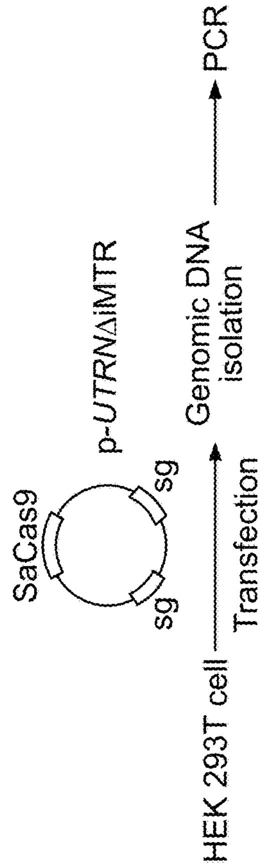
Figure 9C:
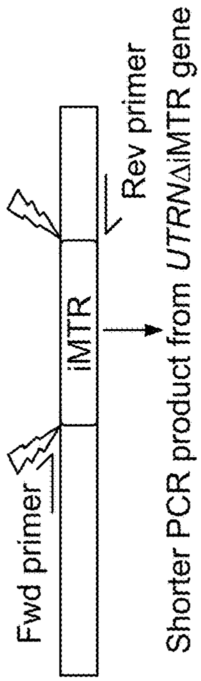
Figure 9D:
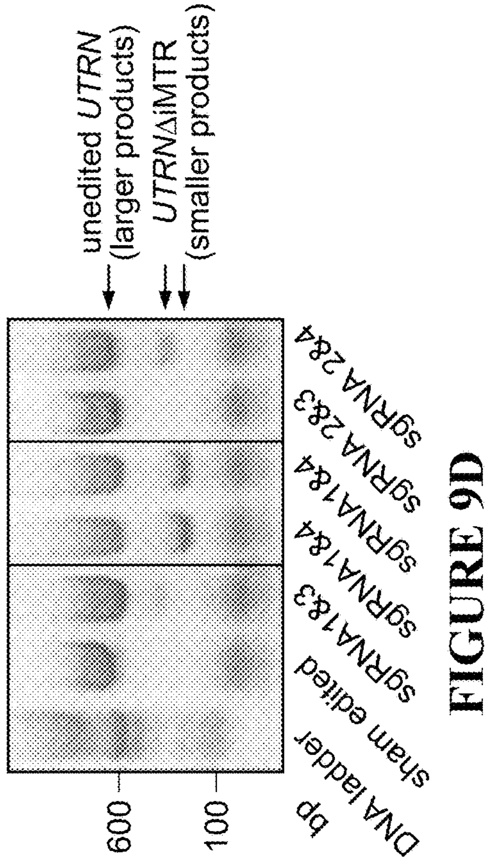
Figure 14:
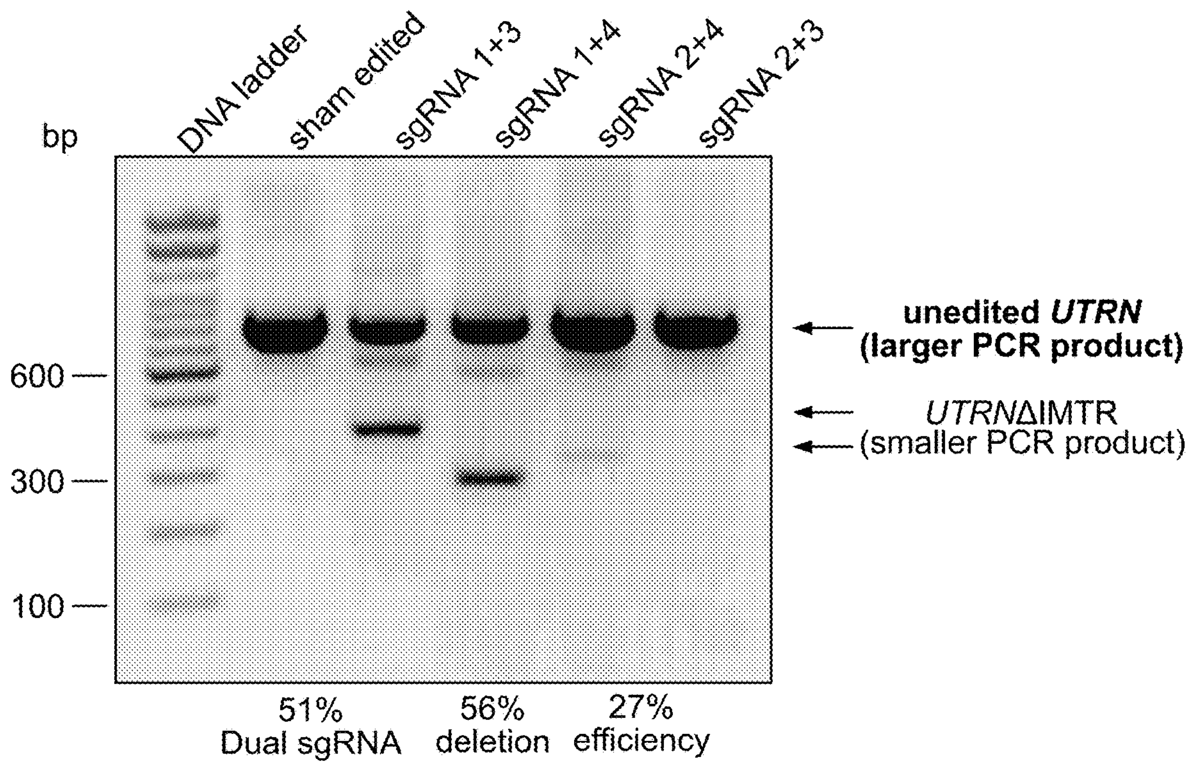
FIG. 14 shows UTRNiMTR deletion efficiency of sgRNA pairs. The DNA gel shows PCR product from unedited and UTRNΔiMTR edited genome in HEK 293T cells transfected with SaCas9 and different sgRNA pairs. The sgRNA pair 1&4 shows maximum deletion efficiency (56%).

Genome Editing-Mediated Utrophin Upregulation In Duchenne Muscular Dystrophy Stem Cells CRISPR/Cas9 Genome Editing Strategy To Delete The iMTR of UTRN It has been previously shown that UTRN gene expression is regulated by five inhibitory miRNAs targeting the 3'UTR (FIG. 9A). To delete these miRNA-binding sites clustered in the iMTR of the UTRN 3'UTR, four compatible short guide RNAs (sgRNAs 1-4) (Table 3) were designed to target the flanking region of iMTR in the human (ITRN gene. Both SaCas9 and the sgRNA pairs were cloned in the same vector (p-UTRNΔiMTR) and transfected in HEK293T cells to determine the deletion efficiency and validate the editing (FIG. 9B). A genomic PCR screening strategy was used to detect successful deletion of the target region using a primer pair flanking the iMTR for PCR screening (FIG. 9C). Gel electrophoresis of PCR products demonstrated that the sgRNA pair 1 & 4 deleted iMTR most efficiently (FIGS. 9D, 14). PCR products were also subjected to DNA sequencing to confirm precision of editing (not shown), prior to utilizing this strategy in hiPSCs.

Genome Edited UTRNΔiMTR DMD-hiPSC Lines Show Utrophin Protein Upregulation

Figure 10A:
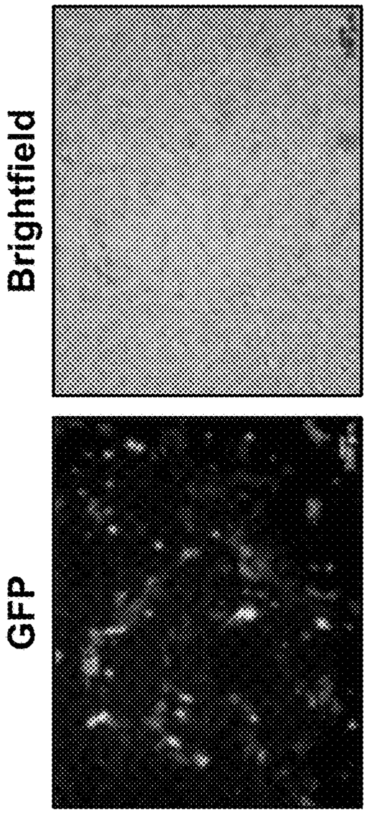
FIGS. 10A-10F show UTRNΔiMTR genome editing in DMD-hiPSCs and utrophin protein upregulation in UTRNΔiMTR clones.
Figure 10B:
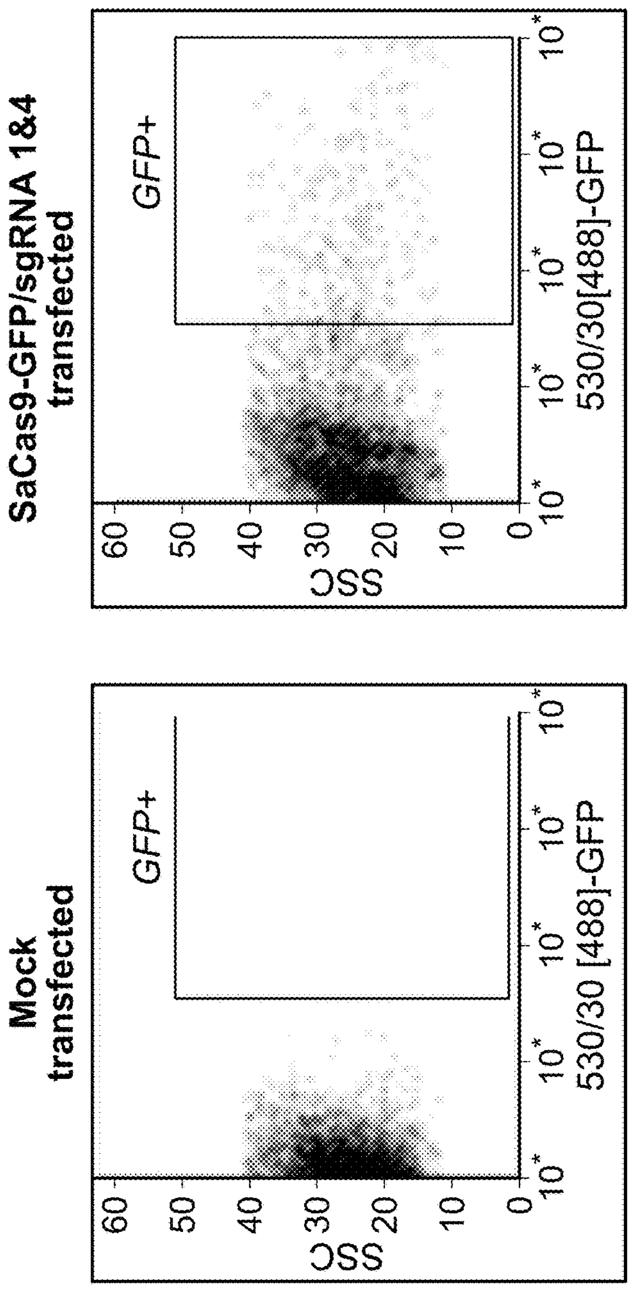
Figure 10C:
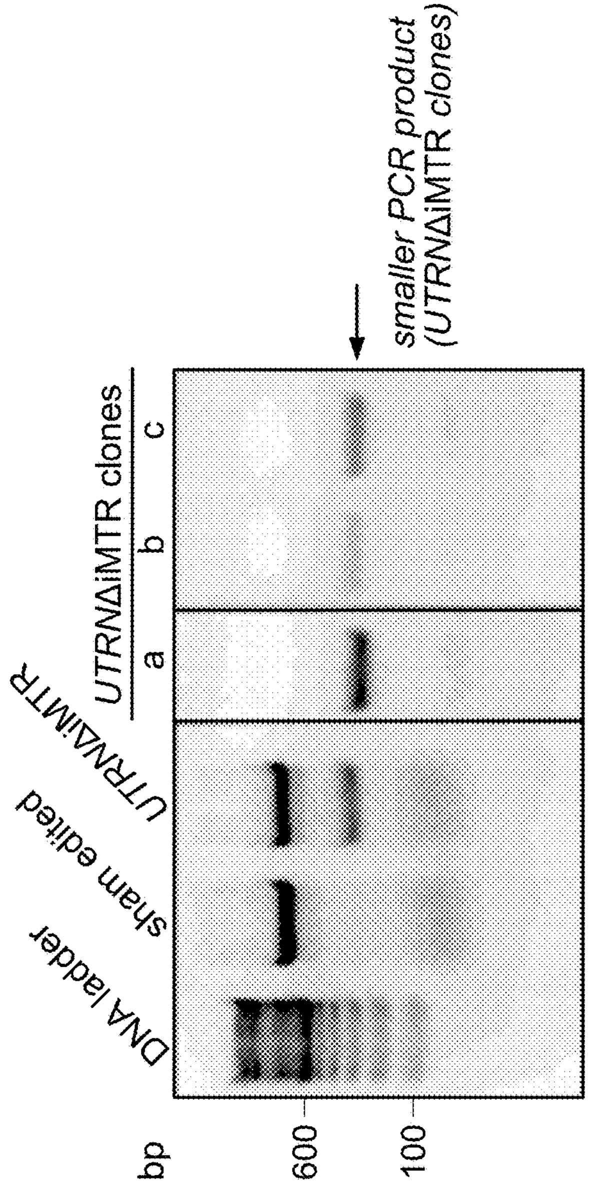
Figure 10D:
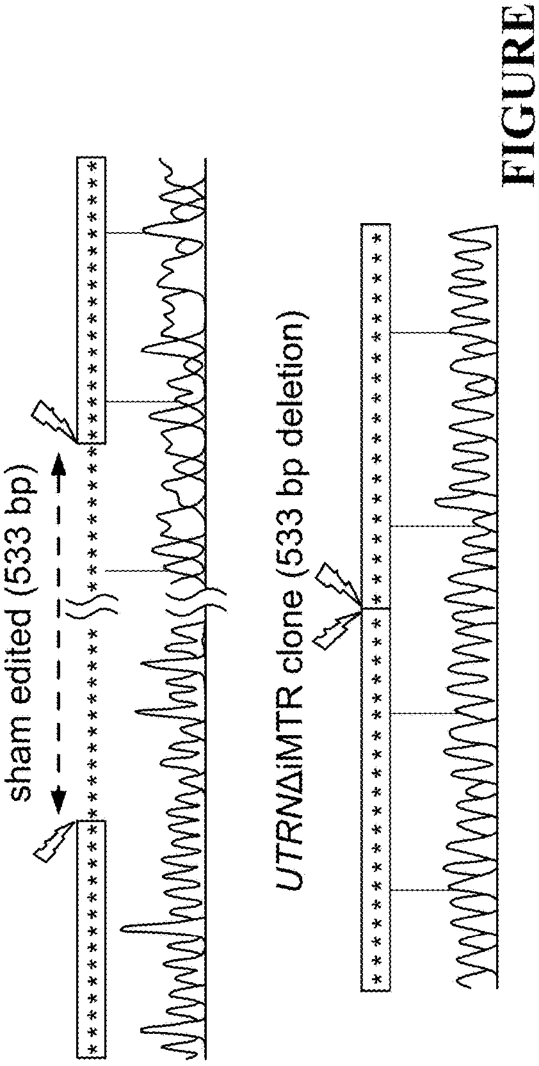
Figure 10E:
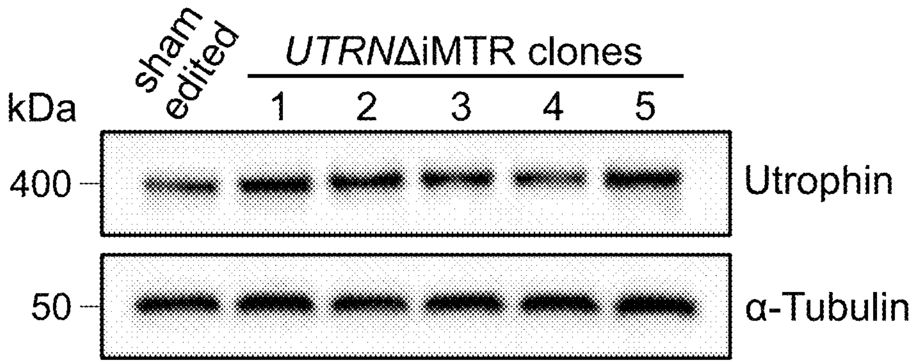
Figure 10F:
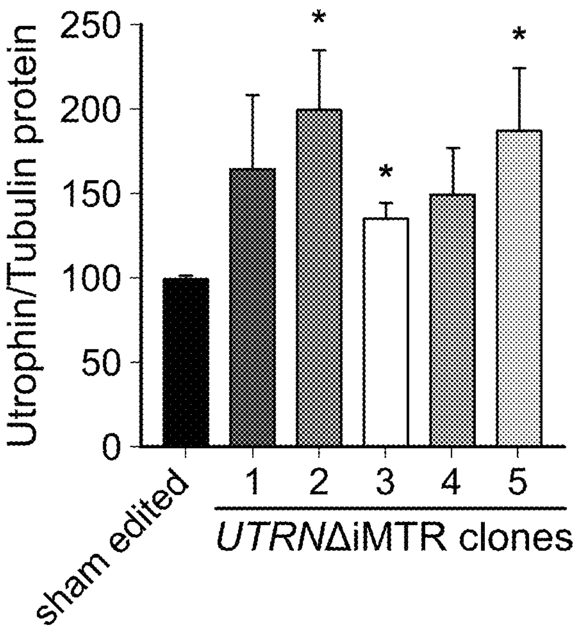

A DMD patient fibroblast-derived hiPSC cell line carrying a deletion of D) MI) exons 46-51 (DMD-hiPSC) was subjected to sgRNA 1 & 4 pair directed CRISPR/Cas9 mediated genome editing followed by FACS isolation of transfection positive population and clonal selection (FIGS. 10A-10B). Stably deleted DMD-hiPSC line clones were screened for homozygous iMTR deletion (UTRNΔiMTR) using the PCR strategy described herein (FIG. 10C). Deletions were confirmed by sequencing PCR products from the edited clones (FIG. 10D). Utrophin protein expression in UTRNΔiMTR and sham-edited DMD-hiPSC were compared by western blotting and UTRNΔiMTR clones showed up-to two-fold utrophin upregulation (FIGS. 10E-10F).

Validation of hiPSC Clones Post-Genome Editing

Figure 11:
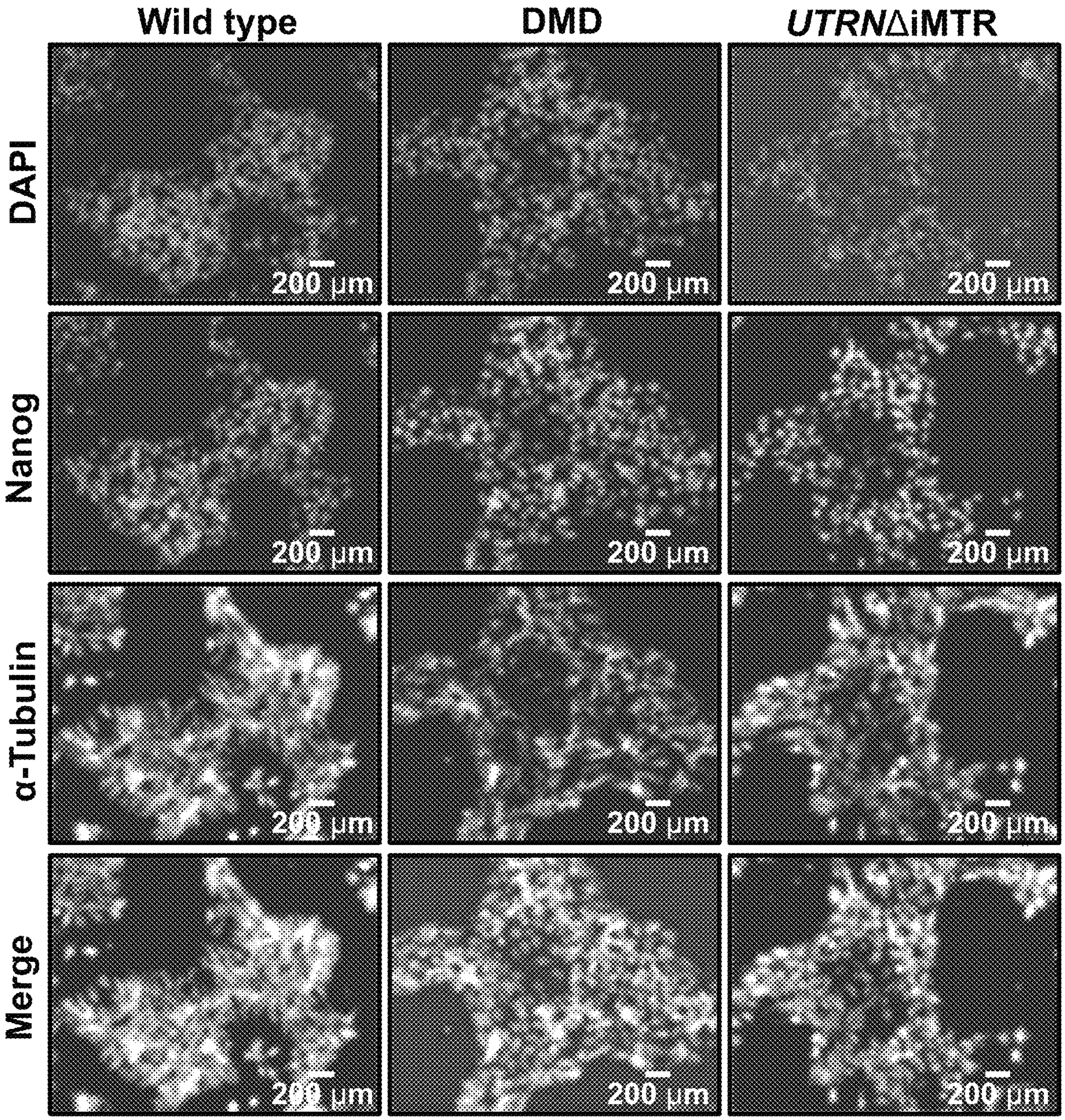
FIG. 11 shows pluripotency marker Nanog expression in wild type, DMD and UTRNΔiMTR hiPSC clones by immunostaining. Immunofluorescent staining images of wild type, DMD and UTRNΔiMTR hiPSC clones with DAPI (blue), Nanog (red) and «-Tubulin (green) staining for validation of pluripotency in post-genome edited lines. The merge panel at bottom shows nuclear localization of pluripotency marker Nanog in different clones. Magnification 20×, scale bar 200 μm.

Pluripotency of the wild type, DMD and edited UTRNΔiMTR hiPSC clones was confirmed by immunostaining for nuclear expression of the pluripotency marker Nanog (FIG. 11). The top five potent off-target sites of the sgRNA 1 & 4 used for genome editing were determined with the COSMID bioinformatics-based tool (Tables 4-5) and sequenced by PCR amplification of the loci. No off-target mutations were observed at these sites in the selected UTRNΔiMTR clones, thus demonstrating the precise nature of genome editing of the guide RNA pairs.

Figure 12A:
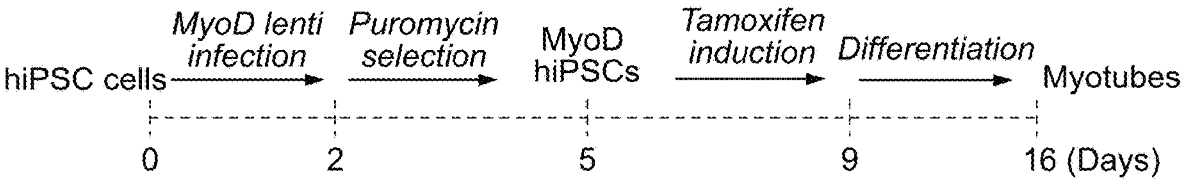
FIGS. 12A-12D show MyoD mediated direct differentiation of hiPSC clones to myogenic lineage.
Figure 12B:
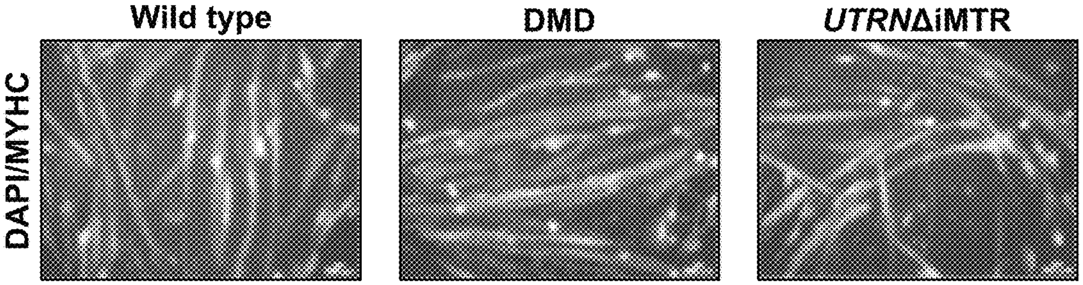
Figure 12C:
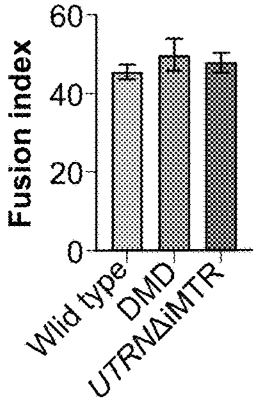
Figure 12D:
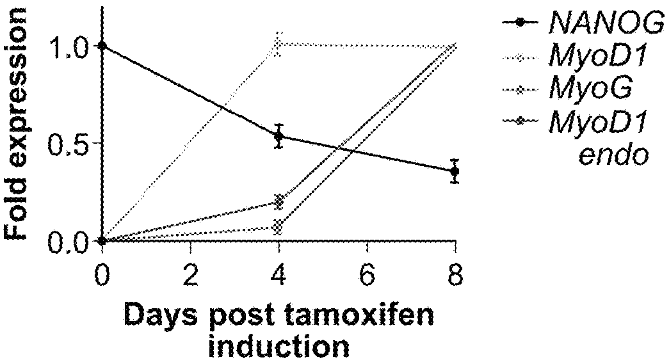
Figure 17B:
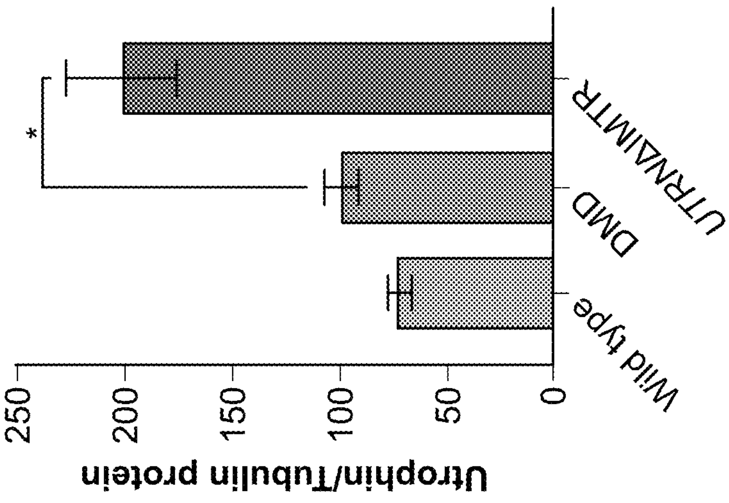
FIGS. 17A-17B shows utrophin protein expression in iPSC differentiated myotubes. Utrophin expression in wild type, DMD and UTRNΔiMTR iPSC cell line derived myotubes were checked by western blotting.
Figure 17A:
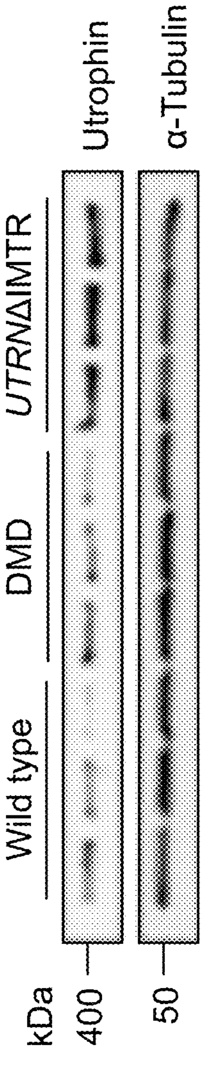

Characterization of hiPSCs Differentiated To Myogenic Lineage By MyoD Overexpression The wild type, DMD and selected UTRNΔiMTR hiPSC clones were differentiated using a tamoxifen inducible MyoD expressing lentivirus (FIG. 12A). The edited and unedited fused, multinucleated, myotubes showed positive myosin heavy chain (MYHC) expression by immunostaining upon differentiation (FIG. 12B). For all three differentiated lines, 40 to 50% of multinucleated myotubes were MYHC-positive myotubes (FIG. 12C). Expression of the myogenic genes (MyoD1, MyoG (Myogenin) and endogenous MyoD1) and the pluripotency marker Nanog was quantified in the UTRNΔiMTR cells by qPCR at day 0, day 4 and day 8 post-tamoxifen induction. The qPCR profile showed a sharp decline in Nanog expression and a concomitant increase in MyoD1, MyoG and endogenous Myol) I genes, supporting differentiation of the UTRNΔiMTR cells to a myogenic lineage (FIG. 12D). Utrophin expression in the differentiated myotubes were checked by Western blotting. UTRNΔiMTR myotubes showed higher utrophin expression compared to DMD myotubes (FIG. 17).

Figure 13A:
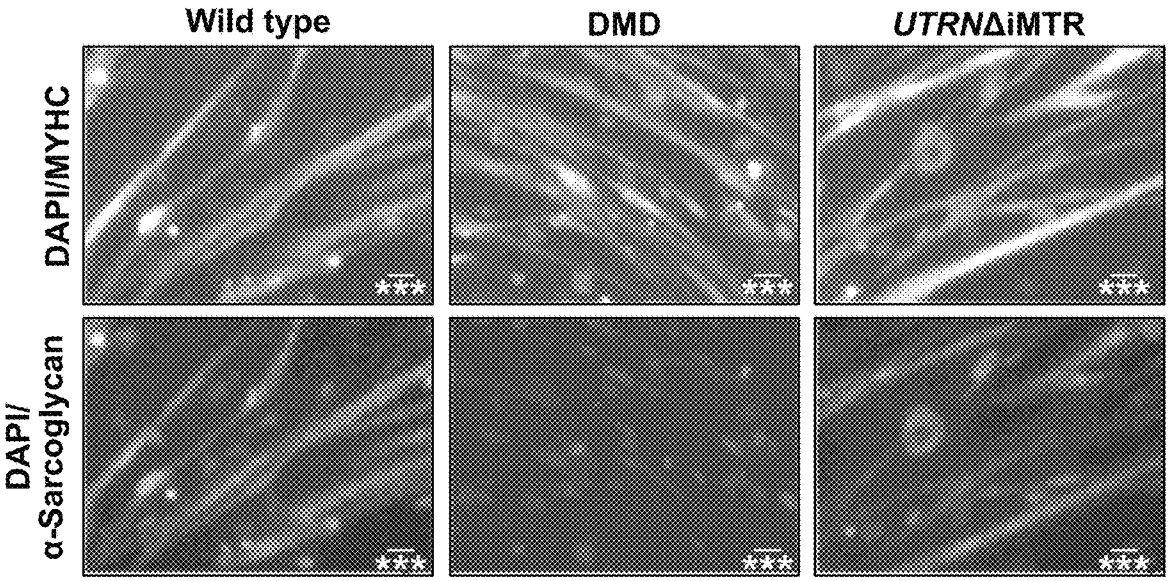
FIGS. 13A-13C show a-sarcoglycan expression in differentiated myotubes.
Figure 13B:
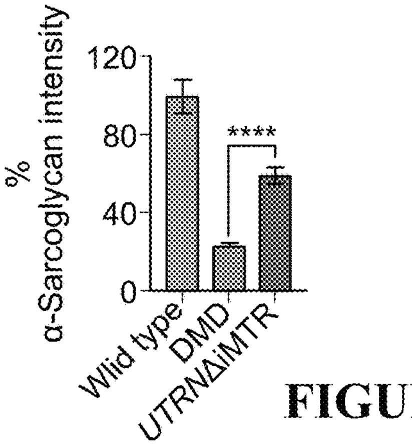
Figure 13C:
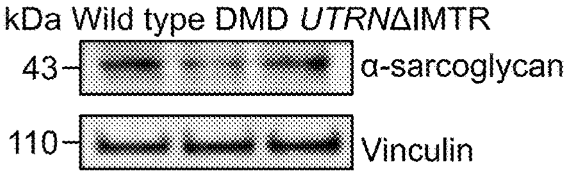
Figure 15:
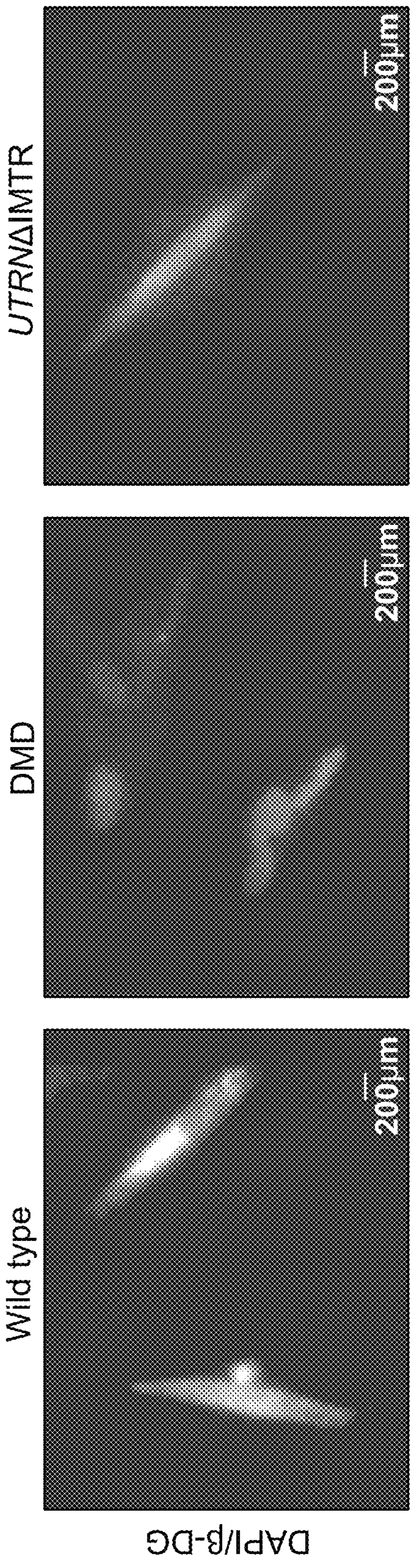
FIG. 15 shows expression of β-dystroglycan (B-DG) in differentiated myotubes. Wild type, DMD and UTRNΔiMTR myotubes were stained with mouse anti-DG (green) and DAPI (blue). Scale bar=200 μm. The wild type myotubes showed higher expression of cytoplasmic β-DG. In the absence of dystrophin, the DMD myotubes showed lack of β-DG staining. In contrast, UTRNΔiMTR myotubes showed restoration of β-DG expression compared with the DMD myotubes.

Utrophin Overexpression Increases Sarcolemmal a-Sarcoglycan Expression In UTRNΔiMTR hiPSC Derived Myotubes The absence of dystrophin protein in DMD muscles results in the disruption of the DGC and the lack of sarcolemmal staining for different components of the DGC, such as α-sarcoglycan. Restoration of individual DGC proteins expression at the sarcolemma suggests restoration of the DGC and is considered as a marker of improvement when evaluating dystrophin or utrophin-based therapeutic strategies. Whether upregulated utrophin could restore a-sarcoglycan expression in UTRNΔiMTR DMD-hiPSC-derived myotubes was therefore tested by immunostaining. The UTRNΔiMTR DMD-hiPSC-derived myotubes showed significantly higher «-sarcoglycan level compared to the DMD-hiPSC-derived myotubes, supporting the restoration of utrophin anchored DGC by genome editing in the DMD-hiPSCs (FIGS. 13A-13B). The increases noted on immunostaining was independently supported by western blot data showing overall higher expression of a-sarcoglycan in UTRNΔiMTR DMD-hiPSC-derived myotubes compared with DMD-hiPSC-derived myotubes (FIG. 13C). Consistent with the utrophin upregulation mediated restoration of the DGC, restoration of another DGC member, B-dystroglycan in UTRNΔiMTR DMD-hiPSC-derived myotubes was shown in FIG. 15.

DISCUSSION

Figure 8:
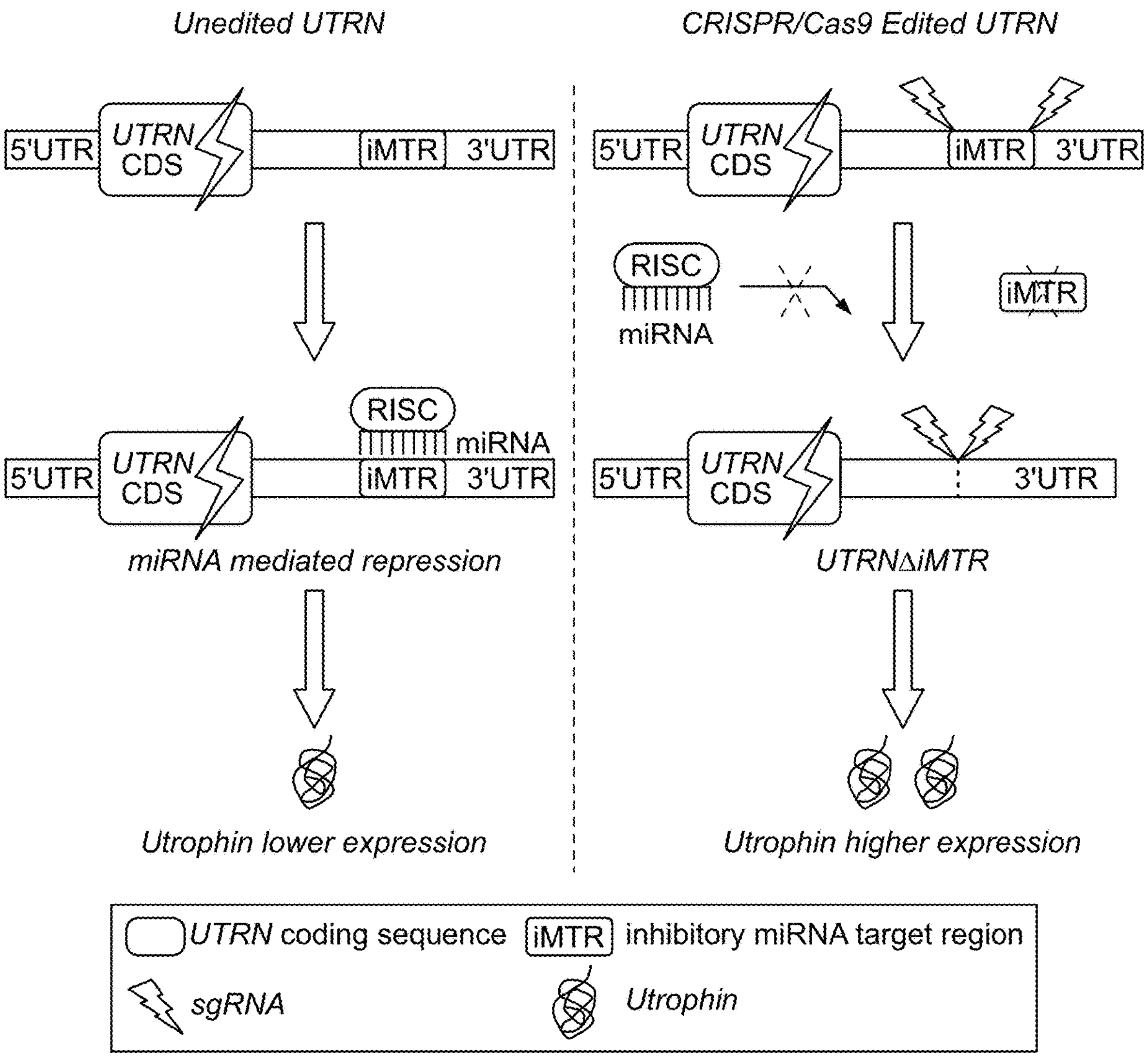
FIG. 8 shows a CRISPR/Cas9 strategy for relieving miRNA driven post transcriptional repression and increased expression of utrophin. The schematic summarizes one embodiment of CRISPR/Cas9 genome editing strategy to delete the iMTR from the UTRN 3'UTR with the rationale that the edited UTRN 3'UTR (UTRNΔiMTR) would reduce miRNA mediated post-transcriptional repression and lead to higher expression of utrophin.

The rapid developments in genome editing has generated enormous excitement and hope for treating devastating diseases such as DMD. In the present study, a CRISPR/Cas9 mediated genome editing approach was described for increasing utrophin expression as a therapeutic strategy for DMD (FIG. 8). This approach was used to delete a 500 bp iMTR containing five miRNA binding sites (i.e. miR-150, miR-296-5p, miR-133b, let-7c and miR-196b) within the UTRN 3' UTR in HEK 293T cells and select appropriate sgRNAs pairs (FIG. 9). To test the strategy, sgRNA pair 1 & 4 was used to delete the iMTR from DMD-hiPSCs (FIGS. 10A-10D) as well as validated the UTRNΔiMTR DMD-hiPSC clonal lines for utrophin upregulation by western blotting (FIGS. 10E-10F) and expression of the pluripotency marker Nanog by immunofluorescence (FIG. 11). Lentivirus driven MyoD mediated myogenic differentiation was utilized to drive the hiPSCs into myotubes and differentiation validated by monitoring the fusion index as well as reduced expression of pluripotency and increased levels of myogenic markers by qPCR (FIG. 12). Upon differentiation to myotubes higher a-sarcoglycan levels were noted in edited compared to unedited DMD myotubes, suggestive of functional improvement due the UTRN genome editing.

Previously described CRISPR/Cas9 mediated genome editing therapeutic strategies for DMD have largely focused on editing dystrophin and met with varying degrees of success in preclinical studies. In common, these approaches while extremely encouraging in vitro and in vivo mouse studies, have fundamental limitations in that they would not be applicable to all DMD patients, need to be custom-designed for specific mutations and would be predicted to be limited by immunity to the newly expressed dystrophin. Nevertheless, AAV mediated CRISPR genome editing in larger animal model of DMD to correct the dystrophin mutation and express a shorter form of dystrophin supports the efficacy and promise of using genome editing for DMD. Dystrophin-independent CRISPR/Cas9 editing approaches have also been described for leveraging myostatin and transcriptional activation of utrophin as potentially therapeutic approaches. The approach presented herein targets post-transcriptional mechanisms for increasing utrophin expression by deleting the miRNA target sites located in the iMTR of the UTRN 3' UTR. The advantages of the approach described herein include: other cellular targets of respective miRNAs remain unperturbed, this single editing strategy is applicable to all DMD patients and a predicted lack of immune issues since DMD patient are not utrophin naive as they express utrophin since before birth.

In vivo preclinical studies using these targets leveraged by genome editing have been achieved using iPSCs as well as AAV-mediated editing with varying degrees of success. AAV-based approaches have the advantage of enabling the same therapeutic viral vector(s) to be used in a number of patients and ease of delivery. However, the AAV-based approaches have limitations related to the cloning capacity, long-term expression of Cas9 and immune reactions against the capsid or cargo (i.e. Cas9, Dsytrophin). While the present study was restricted to genome editing of iPSCs in vitro, editing of autologous and/or allogenic iPSCs coupled with transplantation is a promising approach that has been used in vivo in a variety of disease models including DMD. The recent demonstration that AAV-9 mediated editing can transduce muscle satellite cells and stem cells exemplify the rapid pace of progress toward applying these strategies to develop therapies in DMD. Additionally, the UTRN genome editing strategy and proof-of-principle studies described herein could potentially be combined with full length utrophin, miniatured utrophin (uUtro) upregulation or utrophin-independent approaches for synergistic effects.

Materials & Methods

Cell Culture And Maintenance

Human embryonic kidney (HEK) 293T cells (ATCC) were maintained in standard growth condition in DMEM high glucose (Gibco) supplemented with 10% fetal bovine serum (Sigma-Aldrich) and 1% Pen/Strep (Gibco).

All hiPSCs were reprogrammed from skin fibroblast with STEMCCA cassette in Dr. April Pyle's laboratory, UCLA, as described in Karumbayaram et al, 2012. Two different hiPSC lines were used, one derived from a healthy individual (Wt 1002) and the other one derived from a DMD patient harboring exon 46-51 deletion (CDMD1003). All the hiPSCs were grown in hESC-qualified Matrigel (Corning), fed daily with mTeSR™1 media (STEMCELL Technologies) as previously described and passaged every 4-5 days.

sgRNA Design And Cloning

Figure 16:
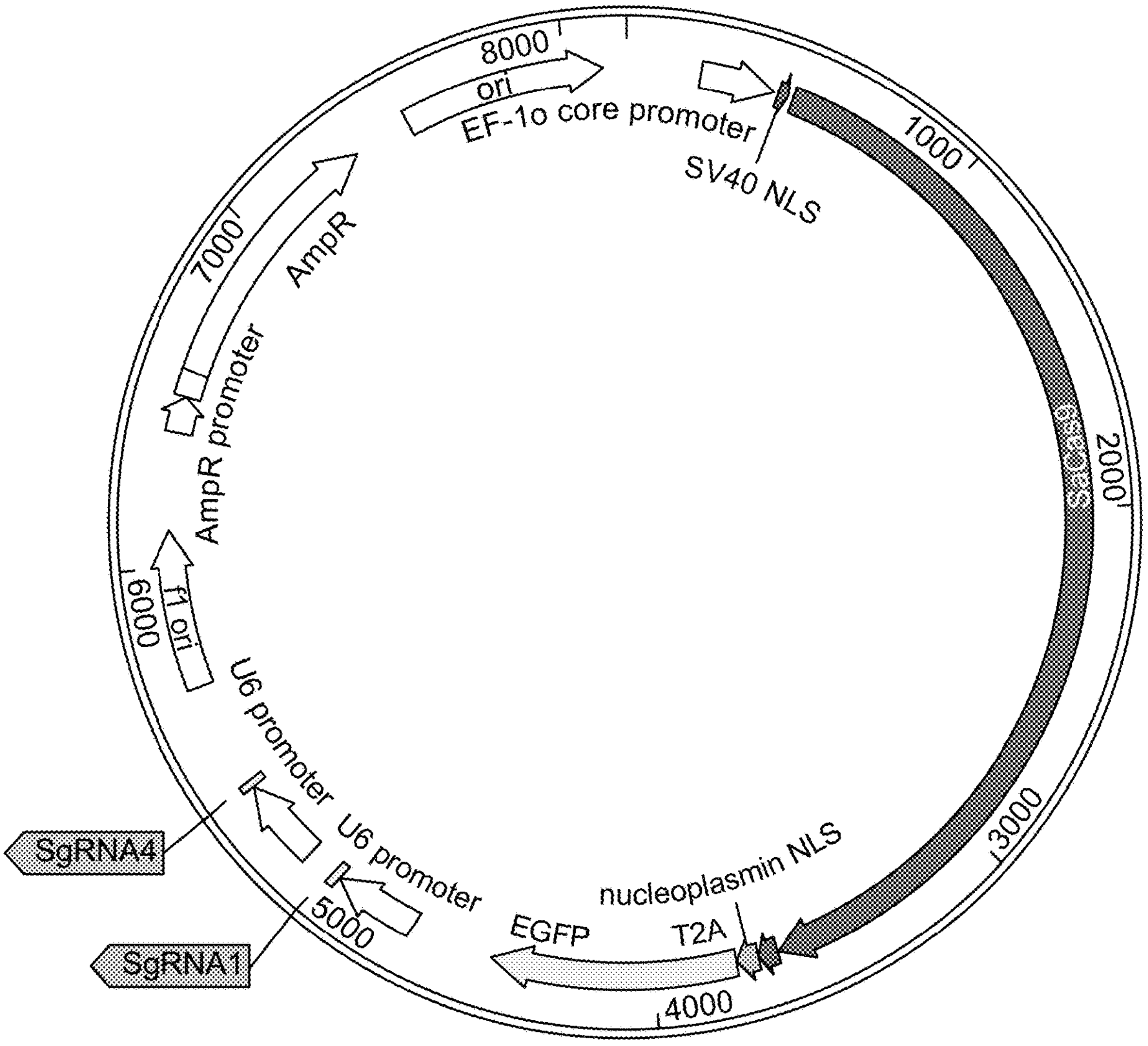
FIG. 16 shows the plasmid map for SaCas9-GFP-SgRNA1&4. The plasmid map shows expression cassette SaCas9 with C-terminal EGFP transgene under $EF_1$-promoter. The guide RNA pairs are cloned under U6 promoter.

All guide RNAs for generating the UTRN iMTR deletion (UTRNΔiMTR) were designed using the Benchling web tool for CRISPR design (Table 3). The CMV promoter of pX601 plasmid (Addgene plasmid #61591) was replaced with EF1α promoter for improved expression of SaCas9 and an EGFP cassette was cloned at C-terminal of SaCas9 (pX601-EF1α:: SaCas9-GFP). Individual sgRNA oligonucleotides were annealed and cloned in this modified pX601 plasmid at the BsaI restriction site before the sgRNA scaffold according to the protocols from the Zhang lab (pX601-EF1α:: SaCas9-GFPU6:: sgRNA). For expression of dual sgRNAs in the same plasmid, the second sgRNA under U6 promoter, were PCR amplified from the corresponding plasmid and subcloned at KpnI site of pX601-EF1α:: SaCas9-GFP-U6:: sgRNA. The cloned plasmids were confirmed by sequencing (FIG. 16).

Genome Editing Validation of sgRNAs

HEK 293T cells were transfected with plasmids containing SaCas9 and different pairs of sgRNAs using lipofectamine 3000 (Invitrogen). The cells were suspended in DirectPCR Lysis Reagent (Viagen Biotech) and incubated with proteinase K for 6 hrs at 55° C. and heat inactivated at 85° C. for 45 mins. One μl of gDNA extract were directly used for PCR screening of UTRN-iMTR deletion. In brief, UTRN forward primer (5'CCTTTCGGGTGAAAGATCAG3') (SEQ ID NO: 64) and UTRN reverse primer (5'ACTTACTTCCCATTGTTACTGC3') (SEQ ID NO: 65) were used to amplify a fragment spanning the iMTR with GoTaq Green Master Mix (Promega), using the following cycling conditions: 95° C. for 5 mins, 34 cycles at 95° C. for 30 s, 60° C. for 30 s, 72° C. for 1 min, and final extension at 72° C. for 10 mins. The PCR products and TrackIt 100 bp DNA ladder (Thermo Fisher Scientific) were electrophoresed on a 2% agarose gel. Gel images were captured using a G: Box imaging system (SYNGENE).

Electroporation of hiPSC Lines

Approximately $5\times10^6$ hiPSC cells were harvested using Accutase solution (Sigma-Aldrich) and washed in phosphate buffered saline (PBS, without $Ca^{2+}$ and $Mg^{2+}$. Harvested cells were suspended in 75 μl of Resuspension Buffer R (Neon Kit, Invitrogen) and mixed with 25 μg of plasmid DNA. Cells were electroporated with three 10 ms pulses at 1200 volts (Neon Transfection System, Thermo Fisher Scientific). Post-electroporation cells were plated on Matrigel coated plated in mTeSR™1 with 5 μM ROCK inhibitor (Y-27632, STEMCELL Technologies).

FACS of hiPSC Lines

Forty eight hours post-electroporation GFP positive hiPSCs were FACS sorted in BD FACS Jazz System (BD Biosciences) at the FACS core of The Children Hospital of Philadelphia. Cells were harvested and suspended as single cells in FACS buffer (PBS, 1% FBS, 1 mM EDTA, 5 μM Y-27632). GFP positive cells were gated with reference to mock electroporated GFP negative cell population. FACS sorted GFP positive hiPSCs were plated immediately in pre-warmed Matrigel coated 10 cm plate (5000-10000 cells/10 cm plate) with mTeSR™1 media supplemented with 10% CloneR™ (STEMCELL Technologies).

UTRNΔiMTR hiPSC Colony Screening

FACS sorted hiPSC cells formed visible colonies by 7 days in culture. Colonies were picked and split in 96-well Matrigel coated plate with mTeSR™1 media. After 3 days cells were split and half harvested for genomic DNA (gDNA) extraction with Direct PCR Lysis Reagent (Viagen Biotech). The gDNA was used for PCR screening of UTRN-iMTR deletion with the primer pairs flanking UTRN-iMTR as mentioned above. Positive homozygous colonies were selected for further expansion.

Western Blot

Cells were lysed in RIPA buffer (20 mM Tris-HCl [pH 7.5], 150 mM NaCl, 1 mM EDTA, 1 mM EGTA, 1% NP-40, 1% sodium deoxycholate, 2.5 mM sodium pyrophoshphate, 1 mM β-glycerophoshphate, 1 mM sodium orthovanadate) supplemented with complete protease inhibitor cocktail (Roche). Total protein was measured by Pierce BCA Protein assay kit (Thermo Scientific). Ten ug of total protein was resolved in 3-8% Tris-Acetate protein gel (NuPAGE, Thermo fisher Scientific) and transferred to nitrocellulose membrane using Trans-Blot Turbo Transfer System (Bio-Rad). For immune-blotting, membranes were first blocked with 5% non-fat dry milk in TBS with 1% Tween 20 for 1 hr at room temperature. After blocking, blots were incubated with the following primary antibodies: mouse monoclonal anti-utrophin (1:100, Mancho3 ($8A_4$), developed by Prof. Glenn E. Morris; DSHB, Iowa) and mouse anti-α-Tubulin (1:5000, T6199, Sigma-Aldrich) for overnight at 4° C. Next day, blots were washed; incubated with mouse IgGK binding protein (m-IgGK BP) conjugated to horseradish peroxidase (HRP) (1:2500, sc-516102, Santa Cruz Biotechnology); washed and developed using Immobilon Western Chemiluminescent HRP Substrate (Millipore) and imaged in LI-COR C-Digit Blot Scanner (LI-COR Biosciences-U.S.).

Immunostaining

Cells were grown in Matrigel coated slide chambers, fixed with freshly prepared 4% paraformaldehyde (PFA) for 15 mins, permeabilized with 0.25% TritonX-100 for 5 mins, blocked with 4% BSA for 1 hr and stained with primary antibody overnight at 4° C. The following primary antibody dilutions were used: rabbit monoclonal anti-Sox2 (1:200, #9092, Cell Signaling Technology), rabbit monoclonal anti-Nanog (1:200, #9092, Cell Signaling Technology), mouse monoclonal anti-α-Tubulin (1:200, T6199, Sigma-Aldrich), MF20c (1:50, DSHB) and goat polyclonal anti-«-sarcoglycan (1:50, sc-16165, Santa Cruz Biotechnology). Secondary antibody dilutions were goat anti-mouse AF488 (1:400, A11029, Thermo Fisher Scientific), donkey anti-goat AF594 (1:400, A11058, Thermo Fisher Scientific). Finally, cells were mounted with ProLong Gold antifade reagent with DAPI (Invitrogen). Images were obtained with the Invitrogen EVOS FL auto 2 Cell Imaging System. Quantification of a-sarcoglycan expression in differentiated myotubes were done in Image J software v2.0 using line intensity plot profile of individual myotubes and normalized with respective DAPI intensity. Percentage of a-sarcoglycan intensity for each group were plotted and statistical analysis was done by Kruskal Wallis multiple comparison test.

RNA Isolation And qPCR

Total RNA was extracted from hiPSC cells with TRIzol (Thermo Fisher Scientific). The yield and quality of purified RNA samples were determined using NanoDrop 2000 Spectrophotometer (Thermo Scientific). One ug of total RNA samples were treated with DNase I (Invitrogen) for 15 mins and then heat inactivated with 2.5 mM EDTA at 65° C. for 10 mins. DNase I treated total RNA was reverse transcribed with oligo dT primer using SuperScript III Reverse transcriptase (Thermo Fisher Scientific). Quantitative PCR was performed in triplicate with Power SYBR Green PCR master mix (Applied Biosystems) in Quant Studio 3 Real-Time PCR System for MyoD1, MyoG, Nanog and GAPDH. GAPDH was used as endogenous control. Relative expression levels were calculated by the cycle threshold method. Primer sequences used in qPCR are mentioned in Table 7.

Lentivirus Generation

For tamoxifen inducible MyoD expressing 3rd generation lentivirus production, HEK 293T cells were transfected at 80-90% confluency with psPAX2, pMD2.G and pCMVMyoD-(ERT) puro plasmids using Lipofectamine 3000 (Invitrogen). Lentiviral particles were harvested as supernatant after 48 hrs and 72 hrs of transfection. The psPAX2 and pMD2.G plasmids and the pCMVMyoD-(ERT) puro plasmid were a generous gift from Dr. Joseph A. Baur's laboratory, UPenn and Dr. M. Carrie Miceli's laboratory, UCLA respectively.

Directed Differentiation of hiPSC Lines hiPSCs were differentiated into skeletal muscle cells by overexpression of MyoD, as described in Young, et. al. hiPSCs were plated as single cells on Matrigel in SMC4 (basal media: DMEM/$F_{12}$ with 20% knock-out serum replacement (KOSR, Life Technologies), 1% Non-Essential Amino Acids Solution (NEAA, Life Technologies), 1% Glutamax (Life Technologies), 100 μM beta-mercaptoethanol, 10 ng/ml basic fibroblast growth factor (bFGF, Life Technologies); SMC4: basal media with daily addition of 5 μM ROCK inhibitor (Y27632, StemCell Technologies), 0.4 μM PD0325901 (Sigma-Aldrich), 1 μM CHIR99021 (Tocris Bioscience), 2 μM SB431542 (Tocris Bioscience)). When cells were 70-80% confluent they were infected with tamoxifen inducible MyoD-ERT lentivirus with 4 μg/ml protamine sulfate (Sigma-Aldrich) and spun inoculated at 1250 rpm for 90 mins at 32° C. Cells were selected 48 hrs post-transduction with 1 μg/ml puromycin in SMC4 for 3 days. Next day cells were split and plated on Matrigel in basal media without bFGF plus 5 μM ROCK inhibitor at approximately $1\times10^5$ cells/cm$^2$. The cells were treated with 5 μM tamoxifen in DMEM with 15% FBS for 4 days for MyoD induction and then differentiated in low glucose DMEM with 5% horse serum and 1 μM tamoxifen for 7 days with daily change of media.

Statistical Analysis

Data were analyzed using the GraphPad Prism v8 statistical software package. Values are presented as mean±standard error of mean (SEM). Statistical analysis was performed using Mann-Whitney test with statistical significance set at $P<0.05$. For image quantification statistical analysis was performed using Kruskal-Wallis test with statistical significance set at $P\leq0.05$.

Off-Targets Prediction And Validation

The COSMID off-target prediction analysis tool, which ranks order the off-target sites based on sequence similarity with the guide RNA provided, was used to determine the potential off target activity of guide RNAs. Top ranked homologous sites for each guide RNA were PCR amplified and sequenced to screen for any mutation in the genomic DNA of edited clonal cell lines.

Dual sgRNA Mediated UTRNIMTR Deletion Efficiency Quantification

To determine the cutting efficiency of the sgRNA pairs tested in this study, HEK 293T cells were transfected with plasmids expressing the SaCas9 and dual sgRNAs (sgRNA 1&3, sgRNA 1&4, sgRNA 2&4 and sgRNA 2&3). Three days later the transfected cells were lysed and PCR screened with UTRN forward and reverse primer mentioned before. Equal amount of PCR product and 5 μl of TrackIT 100 bp DNA ladder were run on 2% agarose gel. The gel image was captured using a G: Box imaging system (SYNGENE). Both unedited and UTRNΔiMTR edited PCR products in each lane were quantified using ImageJ software v2.0 in reference with the appropriate size DNA ladder band in the same gel. Deletion efficiency of each pair of sgRNA were shown as percentage of number of DNA copies in edited PCR product normalized with DNA copies in the total PCR product.

Utrophin Protein Expression in iPSC Differentiated Myotubes

The wild type, unedited DMD and the edited UTRNΔiMTR iPSC cell lines were differentiated by MyoD overexpression and total 10 μg protein were loaded for utrophin western blotting. α-Tubulin was used as loading control.

TABLE 3

Oligonucleotide Sequences For Guide RNAs Cloning

| Name | Guide RNA Sequence | Sense Oligo (5'-3') | Antisense oligo (5'-3') |
|---|---|---|---|
| sg1 | TCTATGTCACTGCTTCT ACAG (SEQ ID NO: 66) | CACCGTCTATGTCACTGCTTCT ACAG (SEQ ID NO: 67) | AAACCTGTAGAAGCAGTGACA TAGAC (SEQ ID NO: 68) |
| sg2 | GGTACCTCCACCTACAT CTTT (SEQ ID NO: 69) | CACCGGGTACCTCCACCTACA TCTTT (SEQ ID NO: 70) | AAACAAAGATGTAGGTGGAG GTACCC (SEQ ID NO: 71) |

TABLE 3-continued

Oligonucleotide Sequences For Guide RNAs Cloning

| Name | Guide RNA Sequence | Sense Oligo (5'-3') | Antisense oligo (5'-3') |
|---|---|---|---|
| sg3 | CATAAAGCAGTTTCCA ATGCA (SEQ ID NO: 72) | CACCGCATAAAGCAGTTTCCA ATGCA (SEQ ID NO: 73) | AAACTGCATTGGAAACTGCTT TATGC (SEQ ID NO: 74) |
| sg4 | GAAGACACCAAATCTA CAACT (SEQ ID NO: 75) | CACCGGAAGACACCAAATCTA CAACT (SEQ ID NO: 76) | AAACAGTTGTAGATTTGGTGT CTTCC (SEQ ID NO: 77) |

TABLE 4

Off-Target Sites of Guide RNA1

| | Chormosome position | Query type | Mismatch | Cut site | COSMID Score |
|---|---|---|---|---|---|
| 1 | Chr12:111687717-111687742 | Del 9 | 2 | 111687733 | 1.68 |
| 2 | Chr6:145581830-145581855 | Del 9 | 2 | 145581846 | 1.85 |
| 3 | Chr4:97683403-97683428 | Del 14 | 2 | 97683412 | 2.99 |
| 4 | Chr4:97683403-97683428 | Del 12 | 2 | 97683412 | 2.99 |
| 5 | Chr7:118654093-118654118 | Del 19 | 2 | 118654109 | 6.81 |

TABLE 5

Off-Target Sites of Guide RNA4

| | Chromosome position | Query type | Mismatch | Cut site | COSMID Score |
|---|---|---|---|---|---|
| 1 | Chr6:47204675-47204701 | No indel | 3 | 47204692 | 1.1 |
| 2 | Chr5:32834524-32834549 | Del 18 | 2 | 32834540 | 1.57 |
| 3 | Chr1:180279087-180279114 | Ins 18 | 2 | 180279105 | 2.14 |
| 4 | Chr5:26710353-26710380 | Ins 11 | 2 | 26710371 | 5.32 |
| 5 | Chr15:82779792-82779818 | No indel | 3 | 82779801 | 5.85 |

TABLE 6

Primer Sequences Used For Off-Target Sites PCR Amplification

| Target | Forward primer (5'-3') | Reverse primer (5'-3') |
|---|---|---|
| Off-target1/sgRNA1 | AGTAGCACCTCTCCCCAGGT (SEQ ID NO: 78) | CTGAGGCAGGAAGCTTGAAC (SEQ ID NO: 79) |
| Off-target2/sgRNA1 | TTGCAATTGTTTTTGGCATC (SEQ ID NO: 80) | CTATGCCCAAATAGCCAAGG (SEQ ID NO: 81) |
| Off-target3/4/sgRNA1 | ACAATGAGCCCTTACCCAGA (SEQ ID NO: 82) | GCATCTCGTGTCTCAACATCA (SEQ ID NO: 83) |
| Off-target5/sgRNA 1 | GCCAGGAAGTCCAAGATCAG (SEQ ID NO: 84) | GCAAACATCGTTTTGTGAAGG (SEQ ID NO: 85) |
| Off-target1/sgRNA 4 | TGCACACAAGGTAAGCCAAA (SEQ ID NO: 86) | GAACCAGGGGAGTGATCTGA (SEQ ID NO: 87) |
| Off-target2/sgRNA 4 | CCCTCATCACAGGCAGTTTT (SEQ ID NO: 88) | TTCACTCGGTGTTTCTGACG (SEQ ID NO: 89) |

TABLE 6-continued

Primer Sequences Used For Off-Target Sites PCR Amplification

| Target | Forward primer (5'-3') | Reverse primer (5'-3') |
|---|---|---|
| Off-target3/sgRNA 4 | AAAAAGACCCACCCATCCTT (SEQ ID NO: 90) | CAACAGCGCAAGACTCTGTC (SEQ ID NO: 91) |
| Off-target4/sgRNA 4 | CTGATGCCCACCTGCTAAGT (SEQ ID NO: 92) | GGCTGTGGTGAGCCATTATT (SEQ ID NO: 93) |
| Off-target5/sgRNA 4 | TGCAGTGAGCTGAGACCTTG (SEQ ID NO: 94) | AGGGCTAGTAGGGAGCGTGT (SEQ ID NO: 95) |

TABLE 7

Primer Sequences Used For qPCR.

| Target | Forward primer (5'-3') | Reverse primer (5'-3') |
|---|---|---|
| MyoD1 | TACCCAAGGTGGAGATCCTG (SEQ ID NO: 96) | ATAGATCATGGGCGGTTCAG (SEQ ID NO: 97) |
| NANOG | CAAAGGCAAACAACCCACTT (SEQ ID NO: 98) | TCTGCTGGAGGCTGAGGTAT (SEQ ID NO: 99) |
| MyoG | CAGTGCCATCCAGTACATCG (SEQ ID NO: 100) | AGGTTGTGGGCATCTGTAGG (SEQ ID NO: 101) |
| MyoD1endo | CCCAAGGTGGAGATCCTG (SEQ ID NO: 102) | CCGCTGTAGTCCATCATGC (SEQ ID NO: 103) |

TABLE 7-continued

Primer Sequences Used For qPCR.

| Target | Forward primer (5'-3') | Reverse primer (5'-3') |
|---|---|---|
| GAPDH | GAGTCAACGGATTTGGTCGT (SEQ ID NO: 104) | GACAAGCTTCCCGTTCTCAG (SEQ ID NO: 105) |

All references, including publications, patent applications, and patents, cited herein are hereby incorporated by reference in its entirety herein.

Having described preferred embodiments of the invention with reference to the accompanying drawings, it is to be understood that the invention is not limited to the precise embodiments, and that various changes and modifications may be affected therein by those skilled in the art without departing from the scope or spirit of the invention as defined in the appended claims.

The invention claimed is:

1. A method for improving a dystrophic phenotype in a human subject having Duchenne Muscular Dystrophy (DMD), the method comprising:

CRISPR-cas9 based genome editing a 3' untranslated region (UTR) of a utrophin gene to delete a let-7c microRNA (miRNA) binding sequence in it, wherein deletion of the let-7c miRNA binding sequence alleviates miRNA-mediated repression and upregulates utrophin expression, thereby improving the dystrophic phenotype in the human subject.

2. The method of claim 1, wherein the CRISPR-cas9 based genome editing comprises:

(a) constructing an adenoviral vector comprising a pair of short guide RNAs (sgRNAs), the pair of sgRNAs targeting the let-7c miRNA binding sequence in 3'-UTR for deletion; and (b) administering the constructed adenoviral vector to the human subject.

3. The method of claim 2, wherein the pair of sgRNAs is sgRNA1 and sgRNA4, wherein the sgRNA1 and the sgRNA4 are each within 1-15 base pairs of the let-7c miRNA binding sequence.

4. The method of claim 2, wherein the pair of sgRNAs is sgRNA2 and sgRNA4 wherein the sgRNA2 and the sgRNA4 are each within 1-15 base pairs of the let-7c miRNA binding sequence.

5. The method of claim 2, further comprising inserting an enhanced green fluorescent protein (EGFP) gene in the constructed adenoviral vector in step (a) to EGFP-tag the constructed adenoviral vector.

6. The method of claim 2 or 5, wherein the constructed adenoviral vector is transfected into human stem cells prior to administration to the human subject.

7. The method of claim 6, wherein the stem cells are human induced pluripotent stem cells (hiPSCs).

8. The method of claim 6, wherein the stem cells are human muscle stem cells.

9. The method of claim 1, wherein the let-7c microRNA binding sequence is either SEQ ID NO: 62 or SEQ ID NO: 18.

10. The method claim 1, wherein the CRISPR-cas9 based genome editing further comprises deleting one or more microRNAs selected from the group consisting of miR-133b, miR-150, miR-196b, miR-206, and miR-296-5p.

11. The method of claim 2 or 5, wherein the constructed adenoviral vector is administered to the human subject in vivo.

12. The method of claim 2 or 5, wherein the constructed adenoviral vector is administered to the human subject in utero.

13. The method of claim 1, wherein the dystrophic phenotype is selected from the group consisting of skeletal or cardiac muscle degeneration, skeletal or cardiac muscle weakness, skeletal muscle cramps or pain, respiratory impairment, cardiomyopathy and dystrophin abnormalities in the brain.

14. The method of claim 13, wherein the dystrophin abnormalities in the brain are selected from the group consisting of attention focusing, verbal learning and memory and emotional interaction.

15. A method for treating Duchenne Muscular Dystrophy (DMD) in a human subject, the method comprising:

CRISPR-cas9 based genome editing a 3' untranslated region (UTR) of a utrophin gene to delete a let-7c microRNA (miRNA) binding sequence in it, wherein deletion of the let-7c miRNA binding sequence alleviates miRNA-mediated repression and upregulates utrophin expression, thereby treating DMD in the human subject.

16. The method of claim 15, wherein the CRISPR-cas9 based genome editing comprises:

(a) constructing an adenoviral vector comprising a pair of short guide RNAs (sgRNAs), the pair of sgRNAs targeting the let-7c miRNA binding sequence in 3'-UTR for deletion; and (b) administering the constructed adenoviral vector to the human subject.

17. The method of claim 16, wherein the pair of sgRNAs is sgRNA1 and sgRNA4, wherein the sgRNA1 and the sgRNA4 are each within 1-15 base pairs of the let-7c miRNA binding sequence.

18. The method of claim 16, wherein the pair of sgRNAs is sgRNA2 and sgRNA4 wherein the sgRNA2 and the sgRNA4 are each within 1-15 base pairs of the let-7c miRNA binding sequence.

19. The method of claim 16, further comprising inserting an enhanced green fluorescent protein (EGFP) gene in the constructed adenoviral vector in step (a) to EGFP-tag the constructed adenoviral vector.

20. The method of claim 16 or 19, wherein the constructed adenoviral vector is transfected into human stem cells prior to administration to the human subject.

21. The method of claim 20, wherein the stem cells are human induced pluripotent stem cells (hiPSCs).

22. The method of claim 20, wherein the stem cells are human muscle stem cells.

23. The method of claim 15, wherein the let-7c microRNA binding sequence is either SEQ ID NO: 62 or SEQ ID NO: 18.

24. The method of claim 15, wherein the CRISPR-cas9 based genome editing further comprises deleting one or more microRNAs selected from the group consisting of miR-133b, miR-150, miR-196b, miR-206, and miR-296-5p.

25. The method of claim 16 or 19, wherein the constructed adenoviral vector is administered to the human subject in vivo.

26. The method of claim 16 or 19, wherein the constructed adenoviral vector is administered to the human subject in utero.

27. The method of claim 16, wherein the treatment improves or alleviates skeletal or cardiac muscle degeneration, skeletal or cardiac muscle weakness, skeletal muscle cramps or pain, respiratory impairment, cardiomyopathy and dystrophin abnormalities in the brain.

28. The method of claim 27, wherein the dystrophin abnormalities in the brain are selected from the group consisting of attention focusing, verbal learning and memory and emotional interaction.

* * * * *